US011551353B2

(12) United States Patent
Golden et al.

(10) Patent No.: US 11,551,353 B2
(45) Date of Patent: Jan. 10, 2023

(54) CONTENT BASED IMAGE RETRIEVAL FOR LESION ANALYSIS

(71) Applicant: ARTERYS INC., San Francisco, CA (US)

(72) Inventors: Daniel Irving Golden, Palo Alto, CA (US); Fabien Rafael David Beckers, San Francisco, CA (US); John Axerio-Cilies, Berkeley, CA (US); Matthieu Le, San Francisco, CA (US); Jesse Lieman-Sifry, San Francisco, CA (US); Anitha Priya Krishnan, Foster City, CA (US); Sean Patrick Sall, Indianapolis, IN (US); Hok Kan Lau, San Francisco, CA (US); Matthew Joseph Didonato, Redwood City, CA (US); Robert George Newton, Calgary (CA); Torin Arni Taerum, Calgary (CA); Shek Bun Law, Calgary (CA); Carla Rosa Leibowitz, San Carlos, CA (US); Angélique Sophie Calmon, Montauban (FR)

(73) Assignee: Arterys Inc., San Francisco, CA (US)

( * ) Notice: Subject to any disclaimer, the term of this patent is extended or adjusted under 35 U.S.C. 154(b) by 0 days.

(21) Appl. No.: 16/766,539

(22) PCT Filed: Nov. 15, 2018

(86) PCT No.: PCT/US2018/061352
§ 371 (c)(1),
(2) Date: May 22, 2020

(87) PCT Pub. No.: WO2019/103912
PCT Pub. Date: May 31, 2019

(65) Prior Publication Data
US 2020/0380675 A1    Dec. 3, 2020

Related U.S. Application Data

(60) Provisional application No. 62/589,805, filed on Nov. 22, 2017, provisional application No. 62/589,772, (Continued)

(51) Int. Cl.
G06K 9/00        (2022.01)
G06T 7/00        (2017.01)
(Continued)

(52) U.S. Cl.
CPC ............ G06T 7/0012 (2013.01); G06N 3/08 (2013.01); G06T 7/11 (2017.01); G06V 10/82 (2022.01);
(Continued)

(58) Field of Classification Search
CPC ..................................................... G16B 40/00
See application file for complete search history.

(56) References Cited

U.S. PATENT DOCUMENTS 5,115,812 A   5/1992  Sano et al.
6,018,728 A   1/2000  Spence et al.
(Continued)

FOREIGN PATENT DOCUMENTS

CN   105474219 A   4/2016
CN   105825509 A   8/2016
(Continued)

OTHER PUBLICATIONS

Abadi et al., "TensorFlow: Large-Scale Machine Learning on Heterogeneous Distributed Systems," The Computing Research Repository 1603.04467, 2016. (19 pages).
(Continued)

Primary Examiner — Hadi Akhavannik
(74) Attorney, Agent, or Firm — Seed IP Law Group LLP

(57) ABSTRACT

Computed Tomography (CT) and Magnetic Resonance Imaging (MRI) are commonly used to assess patients with
(Continued)

known or suspected pathologies of the lungs and liver. In particular, identification and quantification of possibly malignant regions identified in these high-resolution images is essential for accurate and timely diagnosis. However, careful quantitative assessment of lung and liver lesions is tedious and time consuming. This disclosure describes an automated end-to-end pipeline for accurate lesion detection and segmentation.

28 Claims, 51 Drawing Sheets

Related U.S. Application Data filed on Nov. 22, 2017, provisional application No. 62/589,872, filed on Nov. 22, 2017, provisional application No. 62/589,876, filed on Nov. 22, 2017, provisional application No. 62/589,833, filed on Nov. 22, 2017, provisional application No. 62/589,838, filed on Nov. 22, 2017.

(51) Int. Cl.
*G06T 7/11* (2017.01)
*G16H 10/60* (2018.01)
*G06N 3/08* (2006.01)
*G06V 10/82* (2022.01)

(52) U.S. Cl.
CPC ... *G16H 10/60* (2018.01); *G06T 2207/10081* (2013.01); *G06T 2207/20081* (2013.01); *G06T 2207/20084* (2013.01); *G06T 2207/30056* (2013.01); *G06T 2207/30064* (2013.01); *G06T 2207/30096* (2013.01)

(56) References Cited

U.S. PATENT DOCUMENTS

| | | |
|---|---|---|
| 6,324,532 B1 | 11/2001 | Spence et al. |
| 6,934,698 B2 | 8/2005 | Judd et al. |
| 7,139,417 B2 | 11/2006 | Nicolas et al. |
| 7,254,436 B2 | 8/2007 | Judd et al. |
| 7,457,656 B2 | 11/2008 | Judd et al. |
| 7,567,707 B2 | 7/2009 | Willamowski et al. |
| 7,668,835 B2 | 2/2010 | Judd et al. |
| 7,764,846 B2 | 7/2010 | Marchesotti et al. |
| 7,958,100 B2 | 6/2011 | Judd et al. |
| 8,055,636 B2 | 11/2011 | Judd et al. |
| 8,098,918 B2 | 1/2012 | Zheng et al. |
| 8,166,381 B2 | 4/2012 | Judd et al. |
| 8,369,590 B2 | 2/2013 | Wang et al. |
| 8,837,800 B1 | 9/2014 | Bammer et al. |
| 9,165,360 B1 | 10/2015 | Bates et al. |
| 9,430,828 B2 | 8/2016 | Wu et al. |
| 9,513,357 B2 | 12/2016 | Hsiao et al. |
| 9,569,736 B1 | 2/2017 | Ghesu et al. |
| 9,589,374 B1 | 3/2017 | Gao et al. |
| 9,607,373 B2 | 3/2017 | Buisseret et al. |
| 9,707,400 B2 | 7/2017 | Grenz et al. |
| 10,117,597 B2 | 11/2018 | Beckers et al. |
| 10,192,129 B2 | 1/2019 | Price et al. |
| 10,331,852 B2 | 6/2019 | Dormer et al. |
| 10,475,537 B2 | 11/2019 | Purdie et al. |
| 10,600,184 B2 | 2/2020 | Golden et al. |
| 10,646,156 B1 | 5/2020 | Schnorr |
| 10,869,608 B2 | 12/2020 | Dormer et al. |
| 10,871,536 B2 | 12/2020 | Golden et al. |
| 10,902,598 B2 | 1/2021 | Golden et al. |
| 2002/0146159 A1 | 10/2002 | Nolte |
| 2003/0072479 A1* | 4/2003 | Sofia Totterman ....... G06T 7/11 |
| | | 382/173 |
| 2003/0174872 A1 | 9/2003 | Chalana et al. |
| 2003/0234781 A1 | 12/2003 | Laidlaw et al. |
| 2005/0079511 A1* | 4/2005 | Mandema ............... G16H 50/50 |
| | | 435/6.11 |
| 2005/0238233 A1 | 10/2005 | Mulet Parada et al. |
| 2006/0106877 A1 | 5/2006 | Lee |
| 2006/0120608 A1 | 6/2006 | Luo et al. |
| 2006/0155187 A1 | 7/2006 | Zhao et al. |
| 2006/0241376 A1 | 10/2006 | Noble et al. |
| 2007/0061460 A1 | 3/2007 | Khan et al. |
| 2008/0054900 A1 | 3/2008 | Polzin |
| 2008/0130824 A1 | 6/2008 | Fujisawa |
| 2009/0105167 A1* | 4/2009 | Potti ........................ G16B 40/20 |
| | | 514/34 |
| 2009/0226064 A1 | 9/2009 | El Fakhri et al. |
| 2009/0234628 A1* | 9/2009 | Yu .......................... A61N 5/1031 |
| | | 703/11 |
| 2010/0085052 A1 | 4/2010 | Johnson et al. |
| 2010/0086948 A1* | 4/2010 | Gold ...................... G16B 40/20 |
| | | 702/19 |
| 2010/0094122 A1 | 4/2010 | Kiraly |
| 2010/0145194 A1 | 6/2010 | Joshi et al. |
| 2010/0158332 A1 | 6/2010 | Rico et al. |
| 2010/0280352 A1 | 11/2010 | Ionasec et al. |
| 2011/0040544 A1* | 2/2011 | Donovan ......... G01N 33/57415 |
| | | 703/11 |
| 2011/0064294 A1 | 3/2011 | Abe et al. |
| 2011/0122226 A1 | 5/2011 | Kamen et al. |
| 2011/0123253 A1 | 5/2011 | Matsui |
| 2011/0173029 A1* | 7/2011 | Hanov ................... G16H 70/20 |
| | | 705/3 |
| 2011/0182493 A1 | 7/2011 | Huber et al. |
| 2011/0230756 A1 | 9/2011 | Axel Odeen et al. |
| 2011/0244415 A1 | 10/2011 | Batesole |
| 2011/0311120 A1 | 12/2011 | Maizeroi-Eugene |
| 2012/0076380 A1 | 3/2012 | Guhring et al. |
| 2012/0114205 A1 | 5/2012 | Tang et al. |
| 2012/0184840 A1 | 7/2012 | Najarian et al. |
| 2012/0271156 A1 | 10/2012 | Bi et al. |
| 2013/0066229 A1 | 3/2013 | Wolff |
| 2013/0259351 A1 | 10/2013 | Wiemker, II |
| 2013/0343626 A1 | 12/2013 | Rico et al. |
| 2013/0345580 A1 | 12/2013 | Poree et al. |
| 2014/0086465 A1 | 3/2014 | Wu et al. |
| 2014/0112564 A1 | 4/2014 | Hsiao et al. |
| 2014/0200824 A1* | 7/2014 | Pancoska ............... G16B 20/20 |
| | | 702/19 |
| 2014/0313222 A1 | 10/2014 | Anderson et al. |
| 2015/0112182 A1 | 4/2015 | Sharma et al. |
| 2015/0117760 A1 | 4/2015 | Wang et al. |
| 2015/0139517 A1 | 5/2015 | Sigurdsson et al. |
| 2015/0178938 A1 | 6/2015 | Gorman, III et al. |
| 2015/0213302 A1 | 7/2015 | Madabhushi et al. |
| 2015/0238148 A1 | 8/2015 | Georgescu et al. |
| 2015/0324690 A1 | 11/2015 | Chilimbi et al. |
| 2015/0327806 A1* | 11/2015 | Kezirian ............... A61B 5/4818 |
| | | 600/533 |
| 2015/0374237 A1 | 12/2015 | Hu et al. |
| 2015/0374243 A1* | 12/2015 | Itu ........................... A61B 5/7275 |
| | | 703/2 |
| 2016/0092721 A1 | 3/2016 | Kanagasingam et al. |
| 2016/0140300 A1 | 5/2016 | Purdie et al. |
| 2016/0203263 A1 | 7/2016 | Maier et al. |
| 2016/0292856 A1 | 10/2016 | Niemeijer et al. |
| 2016/0328643 A1 | 11/2016 | Liu et al. |
| 2016/0338613 A1 | 11/2016 | Beckers et al. |
| 2017/0045600 A1 | 2/2017 | Hsiao et al. |
| 2017/0046616 A1 | 2/2017 | Socher et al. |
| 2017/0046839 A1 | 2/2017 | Paik et al. |
| 2017/0084028 A1 | 3/2017 | Vilsmeier |
| 2017/0103532 A1 | 4/2017 | Ghesu et al. |
| 2017/0116497 A1 | 4/2017 | Georgescu et al. |
| 2017/0175169 A1* | 6/2017 | Lee .................. G01N 33/54373 |
| 2017/0213101 A1 | 7/2017 | Rubens et al. |
| 2017/0220672 A1* | 8/2017 | Sainani ................... G06N 20/00 |
| 2017/0270663 A1 | 9/2017 | Hoffmann et al. |
| 2017/0270666 A1 | 9/2017 | Barnes et al. |
| 2017/0287134 A1 | 10/2017 | Abedini et al. |
| 2017/0372029 A1* | 12/2017 | Saliman ................. G16H 10/60 |

(56) References Cited

U.S. PATENT DOCUMENTS

| | | | |
|---|---|---|---|
| 2018/0005083 | A1 | 1/2018 | Georgescu et al. |
| 2018/0039731 | A1* | 2/2018 | Szeto ............... G16B 40/00 |
| 2018/0116620 | A1 | 5/2018 | Chen et al. |
| 2018/0130203 | A1 | 5/2018 | Abedini et al. |
| 2018/0218497 | A1 | 8/2018 | Golden et al. |
| 2018/0218502 | A1 | 8/2018 | Golden et al. |
| 2018/0240235 | A1 | 8/2018 | Mazo |
| 2018/0253837 | A1 | 9/2018 | Ghesu et al. |
| 2018/0256042 | A1 | 9/2018 | Beckers et al. |
| 2018/0259608 | A1 | 9/2018 | Golden et al. |
| 2018/0315193 | A1 | 11/2018 | Paschalakis et al. |
| 2018/0365824 | A1 | 12/2018 | Yuh et al. |
| 2019/0251688 | A1 | 8/2019 | Madabhushi et al. |
| 2019/0303760 | A1* | 10/2019 | Kumar ............... G06N 3/0454 |
| 2020/0035351 | A1 | 1/2020 | Kim |
| 2020/0052174 | A1 | 2/2020 | Sung |
| 2020/0077893 | A1 | 3/2020 | Shirai et al. |
| 2020/0085382 | A1 | 3/2020 | Taerum et al. |
| 2020/0193603 | A1 | 6/2020 | Golden et al. |

FOREIGN PATENT DOCUMENTS

| | | |
|---|---|---|
| CN | 105828870 A | 8/2016 |
| CN | 205665697 U | 10/2016 |
| CN | 106096616 A | 11/2016 |
| CN | 106096632 A | 11/2016 |
| CN | 106127725 A | 11/2016 |
| CN | 107341265 A | 11/2017 |
| JP | H02147048 A | 6/1990 |
| JP | H0584231 A | 4/1993 |
| JP | H0838444 A | 2/1996 |
| JP | H08140960 A | 6/1996 |
| JP | 2001149361 A | 6/2001 |
| JP | 2008510499 A | 4/2008 |
| JP | 2008526382 A | 7/2008 |
| JP | 2009261519 A | 11/2009 |
| JP | 2010082321 A | 4/2010 |
| JP | 2011523147 A | 8/2011 |
| JP | 2011527055 A | 10/2011 |
| JP | 2012512730 A | 6/2012 |
| JP | 2013223726 A | 10/2013 |
| JP | 2015131023 A | 7/2015 |
| JP | 2015154918 A | 8/2015 |
| KR | 10-2016-0010157 A | 1/2016 |
| WO | 0067185 A1 | 11/2000 |
| WO | 2009142167 A1 | 11/2009 |
| WO | 2010038138 A1 | 4/2010 |
| WO | 2012018560 A2 | 2/2012 |
| WO | 2013006709 A2 | 1/2013 |
| WO | 2015031641 A1 | 3/2015 |
| WO | 2015109254 A2 | 7/2015 |
| WO | 2016141214 A1 | 9/2016 |
| WO | 2017091833 A1 | 6/2017 |
| WO | 2017106645 A1 | 6/2017 |
| WO | 2018/140596 A2 | 8/2018 |
| WO | 2018140596 A2 | 8/2018 |
| WO | 2018/204698 A1 | 11/2018 |
| WO | 2018222755 A1 | 12/2018 |
| WO | 2019103912 A2 | 5/2019 |

OTHER PUBLICATIONS

Amendment, filed Aug. 21, 2018, for U.S. Appl. No. 15/339,475, Hsiao et al., "Comprehensive Cardiovascular Analysis With Volumetric Phase-Contrast MRI," 11 pages.
Amendment, filed Feb. 20, 2018, for U.S. Appl. No. 15/112,130, Beckers et al., "Apparatus, Methods and Articles for Four Dimensional (4D) Flow Magnetic Resonance Imaging," 10 pages.
Amendment, filed Jan. 18, 2016, for U.S. Appl. No. 14/118,964, Hsiao et al., "Comprehensive Cardiovascular Analysis With Volumetric Phase-Contrast MRI," 20 pages.
Amendment, filed Jun. 5, 2018, for U.S. Appl. No. 15/112,130, Beckers et al., "Apparatus, Methods and Articles for Four Dimensional (4D) Flow Magnetic Resonance Imaging," 15 pages.
Amendment, filed Jun. 6, 2016, for U.S. Appl. No. 14/118,964, Hsiao et al., "Comprehensive Cardiovascular Analysis With Volumetric Phase-Contrast MRI," 21 pages.
American College of Radiology, "Liver Reporting & Data System," URL=https://www.acr.org/Clinical-Resources/Reporting-and-Data-Systems/LI-RADS, download date Jun. 28, 2018, 4 pages.
American College of Radiology, "Lung CT Screening Reporting & Data System," URL=https://www.acr.org/Clinical-Resources/Reporting-and-Data-Systems/Lung-Rads, download date Jun. 28, 2018, 4 pages.
Armato, III et al., "The Lung Image Database Consortium (LIDC) and Image Database Resource Initiative (IDRI): A Completed Reference Database of Lung Nodules on CT Scans," Medical Physics 38(2):915-931, 2011.
Avendi et al., "A combined deep-learning and deformable-model approach to fully automatic segmentation of the left ventricle in cardiac MRI," Medical Image Analysis 30:108-119, 2016. (34 pages).
Baur et al., "MelanoGANs: High Resolution Skin Lesion Synthesis with GANs," arXiv:1804.04338v1 [cs.CV], Apr. 12, 2018, 8 pages.
Beckers et al., "Apparatus, Methods and Articles for Four Dimensional (4D) Flow Magnetic Resonance Imaging," U.S. Appl. No. 61/928,702, filed Jan. 17, 2014, 106 pages.
Berens et al., "ZNET—Lung Nodule Detection," Lung Nodule Analysis 2016, URL=https://luna16.grand-challenge.org/serve/public_html/.../ZNET_NDET_160831.pdf/, download date Jun. 28, 2018, 4 pages.
Bergstra et al., "Random Search for Hyper-Parameter Optimization," Journal of Machine Learning Research 13(Feb.):281-305, 2012.
Bock et al., "4D Phase Contrast MRI at 3 T: Effect of Standard and Blood-Pool Contrast Agents on SNR, PC-MRA, and Blood Flow Visualization," Magnetic Resonance in Medicine 63(2):330-338, 2010.
Bock et al., "Optimization pre-processing of time-resolved 2D and 3D Phase Contrast MRI data," 15th Annual Meeting and Exhibition of the International Society for Magnetic Resonance in Medicine, Berlin, Germany, May 19-25, 2007, p. 3138.
Cerqueira et al., "Standardization myocardial segmentation and nomenclature for tomographic imaging of the heart," Circulation 105.4:539-542, 2002.
Chen et al., "Automatic Detection of Cerebral Microbleeds via Deep Learning Based 3D Feature Representation," IEEE 12th International Symposium on Biomedical Imaging, New York City, New York, USA, Apr. 16-19, 2015, pp. 764-767.
Chen et al., "Iterative Multi-Domain Regularized Deep Learning for Anatomical Structure Detection and Segmentation from Ultrasound Images," arXiv, Jul. 7, 2016.
Chernobelsky et al., "Baseline Correction of Phase Contrast Images Improves Quantification of Blood Flow in the Great Vessels," Journal of Cardiovascular Magnetic Resonance 9(4):681-685, 2007.
Chinese Office Action and Search Report, dated Mar. 2, 2020, for Chinese Application No. 201680080450.3, 31 pages. (with English Translation).
Chinese Office Action, dated Jul. 30, 2018, for Chinese Application No. 201580008074.2, 10 pages. (with English Translation).
Chinese Office Action, dated Nov. 1, 2018, for Chinese Application No. 201610702833.1, 13 pages. (with English Machine Translation).
Chinese Office Action, dated Aug. 24, 2015, for Chinese Application No. 201280042949.7, 21 pages. (with English Translation).
Chinese Office Action, dated Jan. 21, 2016, for Chinese Application No. 201280042949.7, 8 pages. (with English Translation).
Chinese Office Action, dated Nov. 15, 2019, for Chinese Application No. 201580008074.2, 21 pages.
Christian et al., "Absolute myocardial perfusion in canines measured by using dual-bolus first-pass MR imaging," Radiology 232.3:677-684, 2004.
Chung et al., "Malignancy estimation of Lung-RADS criteria for subsolid nodules on CT: accuracy of low and high risk spectrum when using NLST nodules," European Radiology 27(11):4672-4679, 2017.

(56) References Cited

OTHER PUBLICATIONS

Dhuquicusma et al., "How to Fool Radiologists with Generative Adversarial Networks? A Visual Turing Test for Lung Cancer Diagnosis," arXiv:1710.09762v2 [cs.CV], Jan. 9, 2018, 5 pages.
Communication pursuant to Article 94(3), dated Feb. 25, 2020, for European Application No. 16869356.2-1218, 6 pages.
Costa et al., "Towards Adversarial Retinal Image Synthesis," arXiv:1701.08974v1 [cs.CV], Jan. 31, 2017, 11 pages.
Delles et al., "Quadratic phase offset error correction of velocity-encoded magnetic resonance imaging data," International Journal of Computer Assisted Radiology and Surgery 4(Supplemental 1):S10-S11, 2009.
Didonato et al., "Machine Learning-Based Automated Abnormality Detection in Medical Images and Presentation Thereof," U.S. Appl. No. 62/770,038, filed Nov. 20, 2018, 37 pages.
Dong et al., "Image Super-Resoultion Using Deep Convolutional Networks," IEEE Transactions on Pattern Anaylsis and Machine Intelligence 38(2):295-307, 2016. (14 pages).
Drozdzal et al., "The Importance of Skip Connections in Biomedical Image Segmentation," arXiv, Sep. 22, 2016. (9 pages).
Díaz et al., "Fast Noncontinous Path Phase-Unwrapping Algorithm Based on Gradients and Mask," 9th Iberoamerican Congresson Pattern Recognition, Puebla, Mexico, Oct. 26-29, 2004, pp. 116-123.
Esteva et al., "Dermatologist-level classification of skin cancer with deep neural networks," Nautre 542(7639):115-118, 2017. (12 pages).
European Office Action, dated Feb. 8, 2019, for European Application No. 15737417.4-1115, 6 pages.
European Office Action, dated May 29, 2018, for European Application No. 15737417.4-1115, 5 pages.
European Office Action, dated Nov. 29, 2018, for European Application No. 12807483.8-1022, 9 pages.
European Office Action, dated Oct. 1, 2020, for European Application No. 18745114.1-1203, 16 pages.
Extended European Search Report, dated Dec. 22, 2020, for European Application No. 18808993.2-1210, 11 pages.
Extended European Search Report, dated Jul. 14, 2017, for European Application No. 15737417.4-1657, 8 pages.
Extended European Search Report, dated Jul. 2, 2019, for European Application No. 16869356.2-1210 / 3380859, 10 pages.
Extended European Search Report, dated Jul. 7, 2015, for European Application No. 12807483.8-1560, 11 pages.
Firmino et al., "Computer-aided detection (CADe) and diagnosis (CADx) system for lung cancer with likelihood of malignancy," BioMedical Engineering OnLine 15:2, 2016. (17 pages).
Fluckiger et al., "Left Atrial Flow Velocity Distribution and Flow Coherence Using Four-Dimensional FLOW MRI: A Pilot Study Investigating the Impact of Age and Pre- and Postintervention Atrial Fibrillation on Atrial Hemodynamics," Journal of Magnetic Resonance Imaging 38(3):580-587, 2013.
Frid-Adar et al., "GAN-based Synthetic Medical Image Augmentation for increased CNN Performance in Liver Lesion Classification," arXiv:1803.01229v1 [cs.CV], Mar. 3, 2018, 10 pages.
Frydrychowicz et al., "Four-dimensional phase contrast magnetic resonance angiography: Potential clinical applications," European Journal of Radiology 80(1):24-35, 2011.
Gatehouse et al., "Flow measurement by cardiovascular magnetic resonance: a multi-centre multi-vendor study of background phase offset errors that can compromise the accuracy of derived regurgitant or shunt flow measurements," Journal of Cardiovascular Magnetic Resonance 12:5, 2010. (8 pages).
Japanese Office Action, dated Apr. 6, 2021, for Japanese Application No. 2018-527794, 7 pages. (with English Translation).
Office Action, dated Apr. 1, 2021, for U.S. Appl. No. 16/617,882, Taerum et al., "Automated Lesion Detection, Segmentation, and Longitudinal Idenueication," 14 pages.
Law et al., "Automated Three Dimensional Lesion Segmentation," U.S. Appl. No. 62/589,876, filed Nov. 22, 2017, 182 pages.
Lecun et al., "Gradient-Based Learning Applied to Document Recognition," Proceedings of the IEEE 86(11):2278-2324, 1998.

Liebowitz et al., "Systems and Methods for Interaction With Medical Image Data," U.S. Appl. No. 62/589,872, filed Nov. 22, 2017, 187 pages.
Lieman-Sifry et al., "Automated Lesion Detection, Segmentation, and Longitudinal Identification," U.S. Appl. No. 62/512,610, filed May 30, 2017, 87 pages.
Lieman-Sifry et al., "FastVentricle: Cardiac Segmentation with ENet," in: Wright, G., et al. (eds.), Functional Imaging and Modelling of the Heart, 9th International Conference, Toronto, ON, Canada, Jun. 11-13, FIMH 2017, Proceedings. (11 pages).
Lin et al., "Focal Loss for Dense Object Detection," arXiv:1708.02002v1 [cs.CV], Aug. 7, 2017, 10 pages.
Long et al., "Fully convolutional networks for semantic segmentation," IEEE Conference on Computer Vision and Pattern Recognition, Boston, Massachusetts, USA, Jun. 7-12, 2015, pp. 3431-3440.
Maier et al., "Classifiers for Ischemic Stroke Lesion Segmentation: A Comparison Study," PLoS ONE 10(12):e0145118, 2015. (16 pages).
Mao et al., "Least Squares Generative Adversarial Networks," arXiv:1611.04076v3 [cs.CV], Apr. 5, 2017, 16 pages.
Mariani et al., "BAGAN: Data Augmentation with Balancing GAN," arXiv:1803.09655v2 [cs.CV], Jun. 5, 2018, 9 pages.
Markl et al., "Comprehensive 4D velocity mapping of the heart and great vessels by cardiovascular magnetic resonance," Journal of Cardiovascular Magnetic Resonance 13(1):7, 2011. (22 pages).
Markl et al., "Generalized Modeling of Gradient Field Non-Linerities and Reconstruction of Phase Contrast MRI Measurements," 11th Annual Meeting and Exhibition of the International Soeciety for Magnetic Resonance in Medicine, Toronto, Canada, Jul. 10-16, 2003, p. 1027.
Markl et al., "Generalized Reconstruction of Phase Contrast MRI: Analysis and Correction of the Effect of Gradient Field Distortions," Magnetic Resonance in Medicine 50(4):791-801, 2003.
Mattias et al., "MRF-Based Deformable Registration and Ventilation Estimation of Lung CT" IEEE Transactions on Medical Imaging, IEEE Service Center, Piscataway, NJ, US, vol. 32, No. 7, pp. 1239-1248, Jul. 2013.
Mirza et al., "Conditional Generative Adversarial Nets," arXiv:1411.1784v1 [cs.LG], Nov. 6, 2014, 7 pages.
Mordvintesev et al., "Inceptionism: Going Deeper into Neural Networks," Jun. 17, 2015, URL=http://googleresearch.blogspot.co.uk/2015/06/inceptionism-going-deeper-into-neural.html, download date Jul. 18, 2017, 8 pages.
Muja et al., "Fast Approximate Nearest Neighbors with Automatic Algorithm Configuration," International Conference an Computer Vision Theory and Applications, Lisboa, Portugal, Feb. 5-8, 2009, pp. 331-340.
National Lung Screening Trial Research Team, "Reduced Lung-Cancer Mortality with Low-Dose Computed Tomographic Streaming," The New England Journal of Medicine 365(5):395-409, 2011.
Newton et al., "Three Dimensional Voxel Segmentation Tool," U.S. Appl. No. 62/589,772, filed Nov. 22, 2017, 180 pages.
Noh et al., "Learning Deconvolution Network for Semantic Segmentation," IEEE International Conference on Computer Vision, Santiago, Chile, Dec. 7-13, 2015, pp. 1520-1528.
Norman et al., "Deep Learning-Based Coregistration," U.S. Appl. No. 62/722,663, filed Aug. 24, 2018, 33 pages.
Notice of Allowance, dated Aug. 4, 2016, for U.S. Appl. No. 14/118,964, Hsiao et al., "Comprehensive, Cardiovascular Analysis With Volumetric Phase-Contrast MRI," 8 pages.
Notice of Allowance, dated Jun. 29, 2018, for U.S. Appl. No. 15/112,130, Beckers et al., "Apparatus, Methods and Articles for Four Dimensional (4D) Flow Magnetic Resonance Imaging," 8 pages.
Odena et al., "Conditional Image Synthesis with Auxiliary Classifier GANs," arXiv:1610.09585v4 [stat.ML], Jul. 20, 2017, 10 pages.
Office Action, dated Apr. 23, 2018, for U.S. Appl. No. 15/339,475, Hsiao et al., "Comprehensive Cardiovascular Analysis With Volumetric Phase-Contrast MRI," 14 pages.
Office Action, dated Dec. 31, 2018, for U.S. Appl. No. 16/181,038, Beckers et al., "Apparatus, Methods and Articles for Four Dimensional (4D) Flow Magnetic Resonance Imaging," 38 pages.

(56) References Cited

OTHER PUBLICATIONS

Office Action, dated Mar. 12, 2018, for U.S. Appl. No. 15/112,130, Beckers et al., "Apparatus, Methods and Articles for Four Dimensional (4D) Flow Magnetic Resonance Imaging," 24 pages.
Office Action, dated Mar. 3, 2016, for U.S. Appl. No. 14/118,964, Hsiao et al., "Comprehensive Cardiovascular Analysis With Volumetric Phase-Contrast MRI," 12 pages.
Office Action, dated Nov. 26, 2018, for U.S. Appl. No. 15/339,475, Hsiao et al., "Comprehensive Cardiovascular Analysis With Volumetric Phase-Contrast MRI," 15 pages.
Office Action, dated Oct. 20, 2015, for U.S. Appl. No. 14/118,964, Hsiao et al., "Comprehensive Cardiovascular Analysis With Volumetric Phase-Contrast MRI," 16 pages.
Parraguez, "Fast and Robust Methods for Non-rigid Registration of Medical Images", Nov. 2014, Retrieved from the Internet: <URL:https://spiral.imperial.ac.uk/bitstream/10044/1/25579/1/Pszczolkowski-S-2015-PhD-Thesis.pdf>.
Paszke et al., "ENet: A Deep Neural Network Architecture for Real-Time Semantic Segmentation," The Computing Research Repository 1606.02147, 2016. (10 pages).
Payer et al., "Regressing Heatmaps for Multiple Landmark Localization using CNNs," 19th International Conference on Medical Image Computing and Computer-Assisted Intervention, Athens, Greece, Oct. 17-21, 2016, pp. 230-238. (9 pages).
Peeters et al., "Analysis and Correction of Gradient Nonlinearity and B0 Inhomogeneity Related Scaling Errors in Two-Dimensional Phase Contrast Flow Measurements," Magnetic Resonance in Medicine 53(1):126-133, 2005.
Plassard et al., "Revealing Latent Value of Clinically Acquired CTs of Traumatic Brain Injury Through Multi-Atlas Segmentation in a Retrospective Study of 1,003 with External Cross-Validation," Proceedings of SPIE 9413:94130K, 2015. (13 pages).
Poudel et al., "Recurrent Fully Convolutional Neural Networks for Multi-slice MRI Cardiac Segmentation," Zuluaga et al., (eds.) Reconstruction, Segmentation, and Analysis of Medical Images, First International Workshops, RAMBO 2016 and HVSMR 2016, Held in Conjunction with MICCAI 2016, Athens, Greece, Oct. 17, 2016, Revised Selected Papers. (12 pages).
Preliminary Amendment, filed Jan. 8, 2014, for U.S. Appl. No. 14/118,964, Hsiao et al., "Comprehensive Cardiovascular Analysis With Volumetric Phase-Contrast MRI," 16 pages.
Preliminary Amendment, filed Jul. 15, 2016, for U.S. Appl. No. 15/112,130, Beckers et al., "Apparatus, Methods and Articles for Four Dimensional (4D) Flow Magnetic Resonance Imaging," 14 pages.
Preliminary Amendment, filed Nov. 13, 2018, for U.S. Appl. No. 15/782,005, Yuh et al., "Interpretation and Quantification of Emergency Features on Head Computed Tomography," 6 pages.
Preliminary Amendment, filed Nov. 2, 2016, for U.S. Appl. No. 15/339,475, Hsiao et al., "Comprehensive Cardiovascular Analysis With Volumetric Phase-Contrast MRI," 8 pages.
Preliminary Amendment, filed Nov. 20, 2013, for U.S. Appl. No. 14/118,964, Hsiao et al., "Comprehensive Cardiovascular Analysis With Volumetric Phase-Contrast MRI," 3 pages.
Preliminary Amendment, filed Oct. 5, 2018, for U.S. Appl. No. 15/779,448, Golden et al., "Automated Cardiac Volume Segmentation," 14 pages.
Radford et al., "Unsupervised Representation Learning with Deep Convolutional Generative Adversarial Networks," arXiv:1511.06434v2 [cs.LG], Jan. 7, 2016, 16 pages.
Restriction Requirement, dated Dec. 20, 2017, for U.S. Appl. No. 15/112,130, Beckers et al., "Apparatus, Methods and Articles for Four Dimensional (4D) Flow Magnetic Resonance Imaging," 7 pages.
Restriction Requirement, dated Sep. 9, 2015, for U.S. Appl. No. 14/118,964, Hsiao et al., "Comprehensive Cardiovascular Analysis With Volumetric Phase-Contrast MRI," 7 pages.
Ronneberger et al., "U-Net: Convolutional Networks for Biomedical Image Segmentation," 18th International Conference on Medical Image Computing and Computer-Assisted Intervention, Munich, Germany, Oct. 5-9, 2015, pp. 234-241.
Ronneberger et al., "U-Net: Convolutional Networks for Biomedical Image Segmentation," arXiv:1505.04597v1 [cs.CV], May 18, 2015, 8 pages.
Rosenfeld et al., "An Improved Method of Angle Detection on Digital Curves," IEEE Transactions on Computers C-24 (9):940-941, 1975.
Russakovsky et al., "ImageNet Large Scale Visual Recognition Challenge," International Journal of Computer Vision 115(3):211-252, 2015.
Salehinejad et al., "Generalization of Deep Neural Networks for Chest Pathology Classification in X-Rays Using Generative Adversarial Networks," arXiv:1712.01636v2 [cs.CV], Feb. 12, 2018, 5 pages.
Extended European Search Report, dated Aug. 16, 2021, for European Application No. 18881685.4-1126, 14 pages.
Kumar et al., "Convolutional Neural Networks for Prostate Cancer Recurrence Prediction," Proc. of SPIE 10140:101400H-1-101400H-12, 2017.
Schultz-Menger, "Standardized image interpretation and post processing in cardiovascular magnetic resonance: Society for Cardiovascular Magnetic Resonance (SCMR) Board of Trustees Task Force on Standardized Post Processing," Journal of Cardiovascular Magnetic Resonance 15:35, 2013. (19 pages).
Shrivastava et al., "Learning from Simulated and Unsupervised Images through Adversarial Training," arXiv:1612.07828V2 [cs.CV], Jul. 19, 2017, 16 pages.
Silverman, "Density estimation for statistics and data analysis," vol. 26m CRC Press, 1986. (22 pages).
Simard et al., "Best Practices for Convolutional Neural Networks Applied to Visual Document Analysis," 7th International Conference on Document Analysis and Recognition, Edinburgh, United Kingdom, Aug. 3-6, 2003, pp. 958-963.
Simpson et al., "Estimation of Coherence Between Blood Flow and Spontaneous EEG Activity in Neonates," IEEE Transactions on Biomedical Engineering 52(5):852-858, 2005.
Sixt et al., "RengerGAN: Generating Realistic Labeled Data," arXiv:1611.01331v5 [cs.NE], Jan. 12, 2017, 15 pages.
Sluimer et al., "Computer Analysis of Computed Tomography Scans of the Lung: A Survey", IEEE Transactions on Medical Imaging, IEEE, Piscataway, NJ, US, vol. 25, No. 4, pp. 385-405, Apr. 1, 2006.
Stalder et al., "Fully automatic visualization of 4D Flow data," 21st Annual Meeting & Exhibiton of the International Society for Magnetic Resonance in Medicine, Salt Lake City, Utah, USA, Apr. 20-26, 2013, p. 1434.
Supplemental Amendment, filed Jun. 6, 2016, for U.S. Appl. No. 14/118,964, Hsiao et al., "Comprehensive Cardiovascular Analysis With Volumetric Phase-Contrast MRI," 21 pages.
Supplementary European Search Report and Communication dated Jul. 2, 2019, for European Application No. 16869356.2, 11 pages.
Suzuki, "Pixel-Based Machine Learning in Medical Imaging," International Journal of Biomedical Imaging 2012:792079, 2012 (18 pages).
Taerum et al., "Automated Lesion Detection, Segmentation, and Longitudinal Identification," U.S. Appl. No. 62/589,825, filed Nov. 22, 2017, 192 pages.
Taerum et al., "Systems and Methods for High Bit Depth Rendering of Medical Images in a Web Browser," U.S. Appl. No. 62/770,989, filed Nov. 23, 2018, 28 pages.
Tran, "A Fully Convolutional Neural Network for Cardiac Segmentation in Short-Axis MRI," The Computing Research Repository 1604.00494, 2016. (21 pages).
Töger et al., "Vortex Ring Formation in the Left Ventricle of the Heart: Analysis by 4D Flow MRI and Lagrangian Coherent Structures," Annals of Biomedical Engineering 40(12):2652-2662, 2012.
Unterhinninghofen et al., "Consistency of Flow Quantifications in tridirectional Phase-Contrast MRI," Proceedings of SPIE 7259:72592C, 2009. (8 pages).
Van Riel et al., "Observer Viability for Classification of Pulmonary Nodules on Low-Dose CT Images and Its Effect on Nodule Management," Radiology 277(3):863-841, 2015.

(56) References Cited

OTHER PUBLICATIONS

Vilariño et al., "Discrete-time CNN for image segmentation by active contours," Pattern Recognition Letters 19:721-734, 1998.
Walker et al., "Semiautomated method for noise reduction and background phase error correction in MR phase velocity data," Journal of Magnetic Resonance Imaging 3(3):521-530, 1993.
Wiehman et al., "Semantic Segmentation of Bioimages Using Convolutional Neural Networks," 2016 International Joint Conference on Neural Networks (IJCNN), IEEE, Jul. 24, 2016, pp. 624-631.
Wolterink et al., "Deep MR to CT Synthesis using Unpaired Data," arXiv:1708.01155v1 [cs.CV], Aug. 3, 2017, 10 pages.
Wong et al., "Segmentation of Myocardium Using Velocity Field Constrained Front Propagation," 6th IEEE Workshop an Applications of Computer Vision, Orlando, Florida, USA, Dec. 3-4, 2002, pp. 84-89.
Yu et al., "Multi-Scale Context Aggregation by Dilated Convolutions," International Conference on Learning Representations, San Juan, Puerto Rico, May 2-4, 2016, 13 pages.
Yuh et al., "Interpretation and Quantification of Emergency Features on Head Computer Tomography," U.S. Appl. No. 62/269,778, filed Dec. 18, 2015, 44 pages.
Zhao et al., "Performance of computer-aided detection of pulmonary nodules in low-dose CT: comparison with double reading by nodule volume," European Radiology 22(10):2076-2084, 2012.
Zhao et al., "Synthesizing Filamentary Structured Images with GANs," arXiv:1706.02185v1 [cs.CV], Jun. 7, 2017, 10 pages.
Zhu et al., "A geodesic-active-contour-based variational model for short-axis cardiac MR image segmentation," International Journal of Computer Mathematics 90(1):124-139, 2013 (18 pages).
Zhu et al., "Unpaired Image-to-Image Translation using Cycle-Consistent Adversarial Networks," arXiv:1703.10593v4 [cs.CV], Feb. 19, 2018, 20 pages.
Öberg, "Segmentation of cardiovascular tree in 4D from PCT-MRI images," Master's Thesis, Lund University, Lund, Sweden, Apr. 8, 2013, 49 pages.
Giese et al., "Optimized Pre-Processing Strategy for the Correction of Gradient Field Inhomogeneities in 3D-PC-MRI," 16th Annual Meeting and Exhibition of the International Society for Magnetic Resonance in Medicine, Toronto, Canada, May 3-9, 2008, p. 1371.
Golden et al., "Automated Cardiac Volume Segmentation," U.S. Appl. No. 62/415,666, filed Nov. 1, 2016, 119 pages.
Golden et al., "Content Based Image Retrieval for Lesion Analysis," U.S. Appl. No. 62/589,805, filed Nov. 22, 2017, 189 pages.
Golden et al., "Patient Outcomes Prediction System," U.S. Appl. No. 62/589,838, filed Nov. 22, 2017, 187 pages.
Goodfellow et al., "Generative Adversarial Nets," arXiv:1406.2661v1 [stat.ML], Jun. 10, 2014, 9 pages.
Gu et al., "Pulmonary nodule registration: Rigid or nonrigid?", Medical Physics, AIP, Melville, NY, US, vol. 38, No. 7, pp. 4406-4414, 2011.
Gulshan et al., "Development and Validation of a Deep Learning Algorithm for Detection of Diabetic Retinopathy in Retinal Fundus Photographs," Journal of the American Medical Association 316(22):2402-2410, 2016.
He et al., "Deep Residual Learning for Image Recognition," IEEE Conference on Computer Vision and Pattern Recognition, Las Vegas, Nevada, USA, Jun. 27-30, 2016, pp. 770-778.
He et al., "Identity Mappings in Deep Residual Networks," 14th European Conference on Computer Vision, Amsterdam, The Netherlands, Oct. 8-16, 2016, 15 pages.
Hennemuth et al., "Fast Interactive Exploration of 4D MRI Flow Data," Proceedings of PIE 7964:79640E, 2011. (11 pages).
Hill et al., "Medical image registration", Physics in Medicine and Biology, Institute of Physics Publishing, Bristol, GB, vol. 46, No. 3, Mar. 1, 2001 (45 pages).
Hong et al., "Automatic lung nodule matching on sequential CT images", Computers in Biology and Medicine, New York, NY, US, vol. 38, No. 5, pp. 623-634, May 1, 2008.

Hsiao et al., "An Integrated Visualization and Quantitative Analysis Platform for Volumetric Phase-Contrast MRI," U.S. Appl. No. 61/571,908, filed Jul. 7, 2011, 18 pages.
Hsiao et al., "Evaluation of Valvular Insufficiency and Shunts with Parallel-imaging Compressed-sensing 4D Phase-contrast MR Imaging with Stereoscopic 3D Velocity-fusion Volume-rendered Visualization," Radiology 265(1):87-95, 2012.
Hsiao et al., "Improved cardiovascular flow quantification with time-resolved volumetric phase-contrast MRI," Pediatric Radiology 41(6):711-720, 2011.
Hsiao et al., "Rapid Pediatric Cardiac Assessment of Flow and Ventricular Volume With Compressed Sensing Parallel Imaging Volumetric Cine Phase-Contrast MRI," American Journal of Roentgenology 198(3):W250-W259, 2012.
Huhdanpaa et al., "Image Coregistration: Quantitative Processing Framework for the Assessment of Brain Lesions," Journal of Digital Imaging 27(3):369-379, 2014.
International Preliminary Report on Patentability, dated Dec. 3, 2019, for International Application No. PCT/US2018/035192, 18 pages.
International Preliminary Report on Patentability, dated Jan. 7, 2014, for International Application No. PCT/US2012/045575, 6 pages.
International Preliminary Report on Patentability, dated Jul. 19, 2016, for International Application No. PCT/US2015/011851, 13 pages.
International Preliminary Report on Patentability, dated Jul. 30, 2019, for International Application No. PCT/US2018/015222, 10 pages.
International Preliminary Report on Patentability, dated Jun. 19, 2018, for International Application No. PCT/US2016/067170, 7 pages.
International Preliminary Report on Patentability, dated May 26, 2020, for International Application No. PCT/US2018/061352, 34 pages.
International Preliminary Report on Patentability, dated May 29, 2018, for International Application No. PCT/US2016/064028, 13 pages.
International Search Report and Written Opinion, dated Jan. 14, 2013, for International Application No. PCT/US2012/045575, 8 pages.
International Search Report and Written Opinion, dated Jul. 17, 2015, for International Application No. PCT/US2015/011851, 17 pages.
International Search Report and Written Opinion, dated Jul. 26, 2018, for International Application No. PCT/US2018/015222, 13 pages.
International Search Report and Written Opinion, dated Mar. 13, 2017, for International Application No. PCT/US2016/064028, 15 pages.
International Search Report and Written Opinion, dated Mar. 16, 2017, for International Application No. PCT/US2016/067170, 9 pages.
International Search Report and Written Opinion, dated May 31, 2019, for International Application No. PCT/US2018/061352, 42 pages.
International Search Report and Written Opinion, dated Oct. 17, 2018, for International Application No. PCT/US2018/035192, 24 pages.
Isola et al., "Image-to-Image Translation with Conditional Adversarial Networks," arXiv:1611.07004v2 [cs.CV], Nov. 22, 2017, 17 pages.
Japanese Office Action, dated Apr. 12, 2016, for Japanese Application No. 2014-519295, 6 pages. (with English Translation).
Japanese Office Action, dated Aug. 29, 2017, for Japanese Application No. 2016-175588, 8 pages. (with English Translation).
Japanese Office Action, dated Mar. 13, 2018, for Japanese Application No. 2016-175588, 4 pages. (with English Translation).
Japanese Office Action, dated Sep. 18, 2018, for Japanese Application No. 2016-565120, 12 pages. (with English Translation).
Japanese Office Action, dated Sep. 29, 2020, for Japanese Application No. 2018-527794, 12 pages. (with English Translation).

(56) References Cited

OTHER PUBLICATIONS

Jepson et al., "Image Segmentation," Segmentation, 2503, published Nov. 21, 2011 (34 pages), URL: http://www.cs.toronto.edu/~fleet/courses/2503/fall11/Handouts/segmentation.pdf.

Kainz et al., "In vivo interactive visualization of four-dimensional blood flow patterns," The Visual Computer 25(9):853-862, 2009.

Karim et al., "Evaluation of current algorithms for segmentation of scar tissue from late gadolinium enhancement cardiovascular magnetic resonance of the left atrium: an open-access grand challenge," Journal of Cardiovascular Magnetic Resonance 15.1:105, 2013. (17 pages).

Kass et al., "Snakes: Active Contour Models," International Journal of Computer Vision 1(4):321-331, 1988.

Kayahbay et al., "CNN-based Segmentation of Medical Imaging Data," ARXIV.org, Cornell University Library, Jan. 11, 2017. (24 pages).

Kilner et al., "Flow Measurement by Magnetic Resonance: A Unique Asset Worth Optimising," Journal of Cardiovascular Magnetic Resonance 9(4):723-728, 2007.

Kingma et al., "Adam: A Method for Stochastic Optimization," 3rd International Conference for Learning Representations, San Diego, California, USA, May 7-9, 2015, 15 pages.

Klein et al., "Evaluation of Optimization Methods for Nonrigid Medical Image Registration Using Mutual Information and B-Splines", IEEE Transactions on Image Processing, Piscataway, NJ, US, vol. 16, No. 12, pp. 2879-2890. Dec. 2007.

Kuhn, "The Hungarian Method for the Assignment Problem," Naval Research Logistics Quarterly 2(1-2):83-97, 1955. (16 pages).

Lankhaar et al., "Correction of Phase Offset Errors in Main Pulmonary Artery Flow Quantification," Journal of Magnetic Resonance Imaging 22(1):73-79, 2005.

Lau et al., "DeepVentricle: Automated Cardiac MRI Ventricle Segmentation with Deep Learning," Conference on Machine Intelligence in Medical Imaging, Alexandria, Virginia, USA, Sep. 12-13, 2016, 5 pages.

Lau et al., "Simulating Abnormalities in Medical Images With Generative Adersarial Networks," U.S. Appl. No. 62/683,461, filed Jun. 11, 2018, 39 pages.

Beckers et al., "Medical Imaging and Efficient Sharing of Medical Imaging Information," U.S. Appl. No. 62/260,565, filed Nov. 29, 2015, 67 pages.

Chinese Office Action and Search Report, dated Sep. 27, 2021, for Chinese Application No. 201880020558.2, 10 pages. (with English Translation).

Dormer et al., "Medical Imaging and Efficient Sharing of Medical Imaging Information," U.S. Appl. No. 62/415,203, filed Oct. 31, 2016, 111 pages.

Golden et al., "Automated Segmentation Utilizing Fully Convolutional Networks," U.S. Appl. No. 62/451,482, filed Jan. 27, 2017, 113 pages.

* cited by examiner 1402  1404

Observation #2

Size (mm)     24
Previous size    (23)
Segment    (IVb ▾)

[LR-3]   Intermediate prob.   ⊗

APHE    No — Not set — Yes
Washout    No — Not set — Yes
Capsule    No — Not set — Yes
Threshold growth    No — Not set — Yes

|  |  | No APHE | | APHE (not rim) | | |
|---|---|---|---|---|---|---|
| Size (mm) | | <20 | ≥20 | <10 | 10–19 | ≥20 |
| Major features | none | LR-3 | LR-3 | LR-3 | LR-3 | LR-4 |
| | one | LR-3 | LR-4 | LR-4 | LR-4/5 | LR-5 |
| | two | LR-4 | LR-4 | LR-4 | LR-5 | LR-5 |

Ancillary    (Select ▾)

COMMENT

| | |
|---|---|
| LESION #2 | |
| Series Description: | WATER:LAVA-FLEX BH POST 3 |
| Study Date: | 2012/07/01 |
| Diameter (mm): | 53 |
| Previous Diameter (mm): | |
| Classification: | Solid module |
| Segment: | |
| LR Score: | LR-4 |
| APHE: | false |
| Washout: | false |
| Capsule: | true |
| Threshold Growth: | false |
| Ancillary: | |
| *Click here to add a comment* |  |

CONTENT BASED IMAGE RETRIEVAL FOR LESION ANALYSIS

OVERVIEW

Various implementations of the present disclosure are discussed herein below. For readability, the implementations are provided under separate headings. In particular, the following top-level headings are provided for the various implementations: Automated Lesion Detection, Segmentation, and Longitudinal Identification; Content Based Image Retrieval for Lesion Analysis; Three Dimensional Voxel Segmentation Tool; Systems and Methods for Interaction with Medical Image Data; Automated Three Dimensional Lesion Segmentation; Autonomous Detection of Medical Study Types; Patient Outcomes Prediction System; and Co-registration. It should be appreciated that the discussion relating to one or more implementations may be applicable to one or more other implementations. Further, features of each of the various implementations discussed herein may be combined with one or more other implementations to provide additional implementations.

A. AUTOMATED LESION DETECTION, SEGMENTATION, AND LONGITUDINAL IDENTIFICATION

Description of the Related Art

Identification of lesions can occur either manually or with the help of semi- or fully-automated software. Use of semi- or fully-automated software for finding possibly malignant regions of interest (ROIs) represented in the scan is commonly referred to as computer aided detection (CAD or CADe).

The lungs are most often imaged with CT scans, as the generally higher spatial resolution of CT over MRI allows for identification of smaller, possibly malignant ROIs than would be possible with MRI. Possibly cancerous ROIs in the lung are often referred to as nodules or lesions; they will be referred to as lesions in the present disclosure. Other malignancies, such as different types of emphysema, can also be identified in CT scans. The standardization of received image data in Hounsfield Units allows for easy assessment of the lesion type. CT scans generally consist of between 50-300 axial slices, with higher resolution in the x-y plane than along the z dimension. As such, doctors often look for possible malignancies by slice-scrolling through these axial slices. However, reading the scan in a coronal or sagittal reformat is not uncommon.

Both CT and MRI are used to image the liver, with pros and cons associated with both. CT is simpler to gather and read, but it does not provide as much information as MRI. MRI's main advantage comes from its ability to collect multi-modal information, using different pulse sequences, providing more insight into the type of lesion and related diseases. However, there is increased difficulty associated with synthesizing the results from the many gathered series compared with reading a single CT scan. Preference for CT or MRI for liver imaging is usually a result of what is available in the referring physician's hospital.

The ROIs in both lung and liver scans require further analysis and study, both qualitatively and quantitatively. Qualitative assessments include the texture, shape, brightness relative to other tissue, and change in brightness over time in cases where contrast is injected into the patient and a time series of scans are available. Quantitative measurements commonly include the number of possibly malignant ROIs, longest linear dimension of the ROIs, the volume of the ROIs, and the changes to these quantities between scans.

Careful quantitative assessment of lung and liver lesions is tedious and time consuming. Detection of these ROIs, which are often camouflaged by surrounding tissue, requires significant clinical training. However, even with training, radiologists are prone to fatigue and mistakes. In addition, after ROIs are detected, quantitative assessment, such as calculating the volume via segmentation, requires additional time and effort. The use of CADe software can improve both accuracy and efficiency for both detection and further quantitative assessment.

Limitations of Previous CADe Approaches

Detection

Finding regions of interest in a volumetric image is a challenging task for both humans and computer algorithms alike. Multiple radiologists reading the same scan often identify different regions as being cause for concern and disagree about likelihood. Single radiologists often fail to identify upwards of 20% of ROIs for lung CT scans as noted by Zhao, Yingru, et al. "Performance of computer-aided detection of pulmonary nodules in low-dose CT: comparison with double reading by nodule volume." *European radiology* 22.10 (2012): 2076-2084. CADe algorithms have the potential to identify ROIs more consistently. However, they also have imperfect sensitivity. All CADe algorithms will have some tradeoff between sensitivity and specificity; higher sensitivity can be achieved (up to a point) at the cost of having more false positives per scan.

Radiologists generally find ROIs by slice-scrolling through the scan, either in an axial, sagittal, or coronal view. Tools commonly used include adjusting the window width/ window level and utilizing an intensity projection (i.e., "thick slice") to help differentiate ROIs from other anatomy.

Most CADe approaches use a multi-stage approach to find ROI candidates. For example, a recent multi-stage pipeline for lung lesion detection was proposed by Firmino, Macedo, et al. "Computer-aided detection (CADe) and diagnosis (CADx) system for lung cancer with likelihood of malignancy," *Biomedical engineering online* 15.1 (2016): 2. The authors segmented the lungs in 3D, segmented the anatomical structures of the lungs (pulmonary vessels, bronchi, etc.) in 3D, detected candidate lesions, reduced the number of false positives, and calculated the likelihood of malignancy. However, multiple of these stages require user input (e.g., placement of seed points) and review, resulting in a slower diagnosis than a more fully-automated method.

The first stage requires the placement of two seed points, one each in the left and right lungs, at which it is possible to utilize an iterative region growing and morphological closing pipeline to segment the lungs. In order to not exclude juxtapleural lesions (attached to the pleural surface), a complicated heuristic is described. At the end of the pipeline, the lung segmentation is presented to the user. If the user deems it not good enough to use, they must place seed points again and repeat the process. Algorithms that do not need to iterate with clinician input are both faster and simpler to use.

For separating lung structures, the authors utilize the Watershed transform to distinguish between pulmonary structures and lesions. This technique allows areas with similar intensities to be grouped, and thus separated. However, while CT intensities are reproducible, lesion intensities and locations can vary greatly; this makes this algorithm highly susceptible to accidental inclusion of lesions in the segmentation of benign pulmonary structures.

A rule-based classifier is utilized to sort through all the contiguous regions segmented by the Watershed transform. The authors define and quantify the Roundness, Elongation, and Energy of each structure and remove those that fall below a heuristically determined threshold. These kinds of thresholds do not usually generalize well beyond the data for which they were initially described.

Candidates that make it past this stage are then filtered with another classifier. Features are extracted for all lesions with the images with the Histogram of Oriented Gradients (HOG) technique then undergo Principal Component Analysis (PCA) to reduce dimensionality. Finally, a support vector machine (SVM) classifier is used on the PCA features. HOG features do not fully characterize the lesion, as they do not consider global context, a major limitation that prevents the classifier from learning lesion shapes. PCA limits the scope of the features found to a subset of all features available, which inherently limits the classifier to capturing only lesions that possess the retained features. Additionally, SVMs do not scale well; given the same amount of data, deep learning models are able to train more efficiently and pick up on more subtle details, resulting in a higher accuracy upper limit.

Segmentation

The most basic method of creating ROI contours is to complete the process manually with some sort of polygonal or spline drawing tool, without any automated algorithms or tools. In this case, the user may, for example, create a freehand drawing of the outline of the ROI, or drop spline control points which are then connected with a smoothed spline contour. After initial creation of the contour, depending on the software's user interface, the user typically has some ability to modify the contour, e.g., by moving, adding or deleting control points or by moving the spline segments. To reduce the onerousness of this process, most software packages that support ROI segmentation include semi-automated segmentation.

Two algorithms for semi-automated ventricular segmentation are the "snakes" algorithm (known more formally as "active contours") and extensions that rely on a shape prior, either in 2D or 3D. For details of the active contours algorithm, see Kass, M., Witkin, A., & Terzopoulos, D. (1988). "Snakes: Active contour models." *International Journal of Computer Vision*, 1(4), 321-331. Both methods utilize a deformable spline that is constrained to wrap to intensity gradients in the image through an energy-minimization approach. Practically, this approach seeks to both constrain the contour to areas of high gradient in the image (edges) and also minimize "kinks" or areas of high orientation gradient (curvature) in the contour. The optimal result is a smooth contour that wraps tightly to the edges of the image. FIGS. 1 and 2 show examples of failure cases for the snakes algorithm for different types of lung lesions. FIG. 1 shows the results of the snakes algorithm (solid line 102) for the given initial condition (dashed line 104) with alpha=0.015, beta=10, and gamma=0.001. The resulting contour wraps the lesion too tightly. FIG. 2 displays the results the snakes algorithm (solid line 202) for the given initial condition (dashed line 204) with alpha=0.15, beta=10, and gamma=0.05. The resulting contour incorrectly spills into the chest wall.

Although the snakes algorithm and other deformable models that rely on a shape prior are common, and although modifying its resulting contours can be significantly faster than generating contours from scratch, the snakes algorithm has several significant disadvantages. In particular, these algorithms require a "seed." The "seed contour" that will be improved by the algorithm is often set by a heuristic for snakes, and for deformable models, the shape prior is usually explicitly defined. Moreover, both algorithms know only about local context. The cost function typically awards credit when the contour overlaps edges in the image; however, there is no way to inform the algorithm that the edge detected is the one desired; e.g., there is no explicit differentiation between the edge of the ROI and blood vessels, airways, or other anatomy. Therefore, the algorithm is highly reliant on predictable anatomy and the seed being properly set.

Furthermore, these algorithms are greedy. The energy function of snakes is often optimized using a greedy algorithm, such as gradient descent, which iteratively moves the free parameters in the direction of the gradient of the cost function. However, gradient descent, and many similar optimization algorithms, are susceptible to getting stuck in local minima of the cost function. This manifests as a contour that is potentially bound to the wrong edge in the image, such as an imaging artifact or an edge that doesn't trace the shape of a complicated ROI.

Additionally, these algorithms have a small representation space. Because they generally only have a few dozen tunable parameters, the algorithms do not have the capacity to represent a diverse set of possible images on which segmentation is desired. Many different factors can affect the perceived captured image of the ROI, including anatomy (e.g., size, shape, texture of ROI, other pathologies, prior treatment), imaging protocol (e.g., operating technician experience, slice thickness, contrast agents, pulse sequence, scanner type, receiver coil quality and type, patient positioning, image resolution) and other factors (e.g., motion artifacts). Because of the great diversity on recorded images and the small number of tunable parameters, a snakes algorithm or deformable model can only perform well on a small subset of "well-behaved" cases.

Despite these and other disadvantages of the snakes algorithm, the snakes algorithm's popularity primarily stems from the fact that the snakes algorithm can be deployed without any explicit "training," which makes it relatively simple to implement. However, the snakes algorithm cannot be adequately tuned to work on more challenging cases.

BRIEF SUMMARY OF AUTOMATED LESION DETECTION, SEGMENTATION, AND LONGITUDINAL IDENTIFICATION

A machine learning system may be summarized as including at least one nontransitory processor-readable storage medium that stores at least one of processor-executable instructions or data; and at least one processor communicably coupled to the at least one nontransitory processor-readable storage medium, in operation the at least one processor: receives learning data comprising a plurality of batches of labeled image sets, each image set comprising image data representative of an input anatomical structure, and each image set including at least one label which: classifies the entire input anatomical structure as containing a lesion candidate; or identifies a region of the input anatomical structure represented by the image set as potentially cancerous; trains a fully convolutional neural network (CNN) model to: classify if the entire input anatomical structure contains a lesion candidate; or segment lesion candidates utilizing the received learning data; and stores the trained CNN model in the at least one nontransitory processor-readable storage medium of the machine learning system. The CNN model may include a contracting path and an expanding path, the contracting path may include a number of convolutional layers and a number of pooling layers, each pooling layer preceded by at least one convolutional layer, and the expanding path may include a number of convolutional layers and a number of upsampling layers, each upsampling layer preceded by at least one convolutional layer and may include a transpose convolution operation which performs at least one of an upsampling operation and an interpolation operation with a learned kernel, or an upsampling operation followed by an interpolation operation to segment a lesion candidate. Skip connections may be included between at least some of the layers in the contracting path and the expanding path where image sizes of those layers are compatible, and the skip connections may include concatenating features maps, or the skip connections may be residual connections and therefore may include adding or subtracting the values of the feature maps The image data may be representative of a chest, including lungs, or of an abdomen, including a liver. The image data may include computed tomography (CT) scan data or magnetic resonance (MR) scan data. Each scan may be resampled to the same fixed spacing. The CNN model may include a contracting path which may include a first convolutional layer which has between 1 and 2000 feature maps and a max-pooling layer having a pooling size of between 2 and 16 and the CNN model may include a number of convolutional layers, where each convolutional layer may include a convolutional kernel of size 3×3 and a stride of 1.

In operation, initial layers of the contracting path may downsample the image data in order to reduce computational cost of the subsequent layers, and subsequent layers may contain more convolutional operations than a first layer of the contracting path. The expanding path may contain fewer convolutional layers than the contracting path. The convolution operations may include a combination of dense 3×3 convolutions, cascaded N×1 and 1×N convolutions, where 3<N<11, and dilated convolutions. The image data may include volumetric images, and each convolutional layer of the CNN model may include a convolutional kernel of size N×N×K pixels, where N and K are positive integers. The image data may be reformatted to be an intensity projection along an axis, such intensity projection data having a depth of between 2 and 512 pixels, and the projection is a mean, median, maximum, or minimum. The received learning data may include both the intensity projection data and non-projected image data, which data may be used as inputs into the CNN model, and the feature maps for the intensity projection data and the non-projected image data may be combined via concatenation, sum, difference, or average. The CNN model may include a series of residual blocks, pooling layers, and non-linear activation functions which classify lesion candidates. Input patches to the CNN model that contain the lesion candidate may be between 4 and 512 pixels along an edge. An input patch to the CNN model may have multiple channels, where each channel may be a plane of between 4 and 512 pixels along an edge, and each channel may be drawn from the set of two-dimensional planes whose centers may further include intersect the three-dimensional anatomical structure that is to be classified as potentially cancerous, where there may be between 3 and 27 channels. The channels may be evenly distributed in solid angle around a three-dimensional anatomical structure that may be classified as potentially cancerous. The CNN model may include two or more paths, each of the two or more paths utilizing multiple series of residual blocks, pooling layers, and non-linear activation functions, and each of the two or more paths may receive a resampled version of the image data at different spatial scales. At least two of the two or more paths may be parallel paths that are combined via concatenating features maps, or adding, subtracting, or averaging the values of the feature maps. The CNN model may receive a volumetric image as input for the purpose of classification, and the volumetric image may be between 4 and 512 pixels along each dimension.

The at least one processor may, for each image set, modify a training loss function to penalize prediction errors in portions of the image data containing the lesion candidate and reduce the penalty of prediction errors in the background of the image data. The modified training loss function may include convolving the ground truth segmentation with a Gaussian kernel, where the width of the kernel may be a hyperparameter. A cancerous anatomical structure may be found utilizing a patch based method, the patches may be a crop of the input image data, and the patch based method may include a proposing cancerous anatomical structure on patches where the edge length of the patch is between 1 pixel and the image size.

The at least one processor may, for each image set, utilize a plurality of trained CNN models to predict lesion candidates, in which each CNN model votes on a relevance of the lesion candidates and the final evaluation is based on a weighted aggregation of the votes from the individual CNN models. For each processed image of the image data, the CNN model concurrently may utilize magnetic resonance imaging (MRI) data for a plurality of different pulse sequences. Each of the different pulse sequences may be a channel, or each of the different pulse sequences may be a separate input and the pulse sequences may be subsequently combined together. The at least one processor may co-register each pulse sequence prior to combining the pulse sequences together. The at least one processor may augment the learning data via modification of at least some of the image data in the plurality of batches of labeled image sets. The at least one processor may augment at least some of the image data in the plurality of batches of labeled image sets according to at least one of: a horizontal flip, a vertical flip, a shear amount, a shift amount, a zoom amount, a rotation amount, a brightness level, a contrast level, a nonlinear deformation, a nonlinear contrast deformation, or a nonlinear brightness deformation. The image data may be augmented either in 2D or 3D.

The CNN model may include a plurality of hyperparameters stored in the at least one nontransitory processor-readable storage medium, and the at least one processor may configure the CNN model according to a plurality of configurations, each configuration including a different combination of values for the hyperparameters; for each of the plurality of configurations, validate the accuracy of the CNN model; and select at least one configuration based at least in part on the accuracies determined by the validations.

A machine learning system may be summarized as including at least one nontransitory processor-readable storage medium that stores at least one of processor-executable instructions or data; and at least one processor communicably coupled to the at least one nontransitory processor-readable storage medium, in operation the at least one processor: receives image data representative of anatomical structures; utilizes at least one CNN to both locate and segment lesion candidates represented in the received image data; classifies malignancy or other properties of the lesion candidates; post-processes the segmentations of the lesion candidates; computes lesion characteristics; stores the generated classifications in the at least one nontransitory processor-readable storage medium.

The segmented lesion candidates may be predicted in 2D, and the at least one processor may stack the segmented lesion candidates to create a 3D prediction volume; and combine the segmented lesion candidates in 3D utilizing 6, 18, or 26-connectivity of the 3D prediction volume. The relevant lesion information may include a center location for each lesion, and the at least one processor may calculate the center location as the center of mass of the predicted probabilities; and implement a proposal network that generates the predicted probabilities. The at least one processor may post-process the segmentations utilizing morphological operations that may include at least one of dilation, erosion, opening or closing. The image data may include 3D scan data, and the at least one processor may extract 2D images from the 3D scan data that are evenly distributed in solid angle for each cancerous anatomical region, the number of 2D images extracted from the 3D scan data may be between 3 and 27. The image data may include 3D scan data, and the at least one processor may augment at least some of the 3D scan data according to at least one of: a horizontal flip, a vertical flip, a shear amount, a shift amount, a zoom amount, a rotation amount, a brightness level, or a contrast level.

A machine learning system may be summarized as including at least one nontransitory processor-readable storage medium that stores at least one of processor-executable instructions or data; and at least one processor communicably coupled to the at least one nontransitory processor-readable storage medium, in operation the at least one processor: receives image data which represents an anatomical structure previously classified to be potentially cancerous; processes the received image data through a fully convolutional neural network (CNN) model to generate probability maps for each image of the image data, wherein the probability of each pixel represents the probability of whether or not the pixel is part of a lesion candidate; and stores the generated segmentations in the at least one nontransitory processor-readable storage medium. The image data may be representative of a chest, including lungs, or of an abdomen, including a liver. The at least one processor may autonomously cause an indication of at least one of the plurality of parts of the cancerous anatomical structure to be displayed on a display based at least in part on the generated probability maps. The at least one processor may post-process the probability maps to ensure at least one physical constraint is met.

The image data may be representative of a chest, including lungs, or of an abdomen, including a liver, and the at least one physical constraint may include at least one of: segmentations of cancerous anatomical structures of the liver do not occur outside of the physical bounds of the liver; cancerous anatomical structures of the lungs do not occur outside of the physical bounds of the lungs; or cancerous anatomical structures of the given organ are not larger than the given organ.

The at least one processor may, for each image of the image data, set the class of each pixel to a foreground cancerous anatomical structure class when the cancerous class probability for the pixel is at or above a determined threshold, and set the class of each pixel to a background class when the cancerous class probability for the pixel is below a determined threshold; and store the set classes as a label map in the at least one nontransitory processor-readable storage medium.

The at least one processor may, for each image of the image data, set the class of each pixel to a background class when the pixel is not part of a central fully-connected segmentation, where fully-connected is defined by either 6-, 18-, or 26-connectivity in 3D, and a central lesion is a lesion of interest for a given patch submitted to the CNN model; and store the set classes as a label map in the at least one nontransitory processor-readable storage medium. The determined threshold may be user adjustable. The at least one processor may determine the volume of all lesion candidates utilizing the generated segmentations. The at least one processor may cause the determined volume of at least one unique cancerous anatomical structure to be displayed on a display.

The at least one processor may cause a display to present the segmentations to a user as a mask or contours; and implement a tool that is controllable via a cursor and at least one button, in operation, the tool edits the segmentations via addition or subtraction, and the tool continuously adds regions underneath the cursor to the segmentation, or continuously subtracts regions underneath the cursor from the segmentation, for as long as the at least one button is activated. The CNN model may include a number of convolutional layers, and each convolutional layer of the CNN model may include a convolutional kernel of sizes $N \times N \times K$ pixels, where N and K are positive integers. The at least one processor may utilize metadata related to the lesion candidate with the at least one CNN model to improve segmentations.

A machine learning system may be summarized as including at least one nontransitory processor-readable storage medium that stores at least one of processor-executable instructions or data; and at least one processor communicably coupled to the at least one nontransitory processor-readable storage medium, in operation the at least one processor: receives two sets of image data representative of the same anatomical structure; co-registers the image data; and aligns any potentially malignant anatomical structures across the two sets of image data. The two sets of image data may be from the same patient and may have been acquired at different times, or the two sets of image data may be from the same patient and may be from different scan sequences. The at least one processor may align the center of the two sets of images. The at least one processor may co-register the two sets of images via a transformation that may be calculated via gradient descent to find a rigid affine transformation such that mutual information between the two sets of images is maximized. Subsequent to the co-registration of the image data, the at least one processor may pair lesions identified in one of the two sets of image data with lesions identified in the other of the two sets of image data if the lesions are not further than a distance X away from each other, where X is a specific value larger than 1 mm until there are no more lesions left for pairing. Subsequent to the co-registration of the image data, the at least one processor may pair lesions identified in one of the two sets of image data with lesions identified in the other of the two sets of image data according to criteria that minimizes the sum of distances among the paired lesions, where lesions that are greater than 50 mm apart from each other are not paired with each other.

A display system may be summarized as including at least one nontransitory processor-readable storage medium that stores at least one of processor-executable instructions or data; and at least one processor communicably coupled to the at least one nontransitory processor-readable storage medium, in operation the at least one processor: causes a display to present the set of image data comprising a plurality of anatomical structures, wherein the opacity of certain anatomical structures is lower than that of other anatomical structures.

The processor may receive a set of image data representative of a plurality of anatomical structures; identify at least one of the anatomical structures as being not of interest; and adjust the opacity of the identified anatomical structure not of interest to be lower than the opacity of the other of the plurality of anatomical structures.

The opacity may be adjusted based on an intensity threshold.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 52 is a screenshot of a user interface that is used to capture LI-RADS features, which allows users to input each feature manually or to select a score from a score table, according to one non-limiting illustrated implementation.

DETAILED DESCRIPTION

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

1st Embodiment: Automated Detection and Segmentation

Overview

Figure 1:
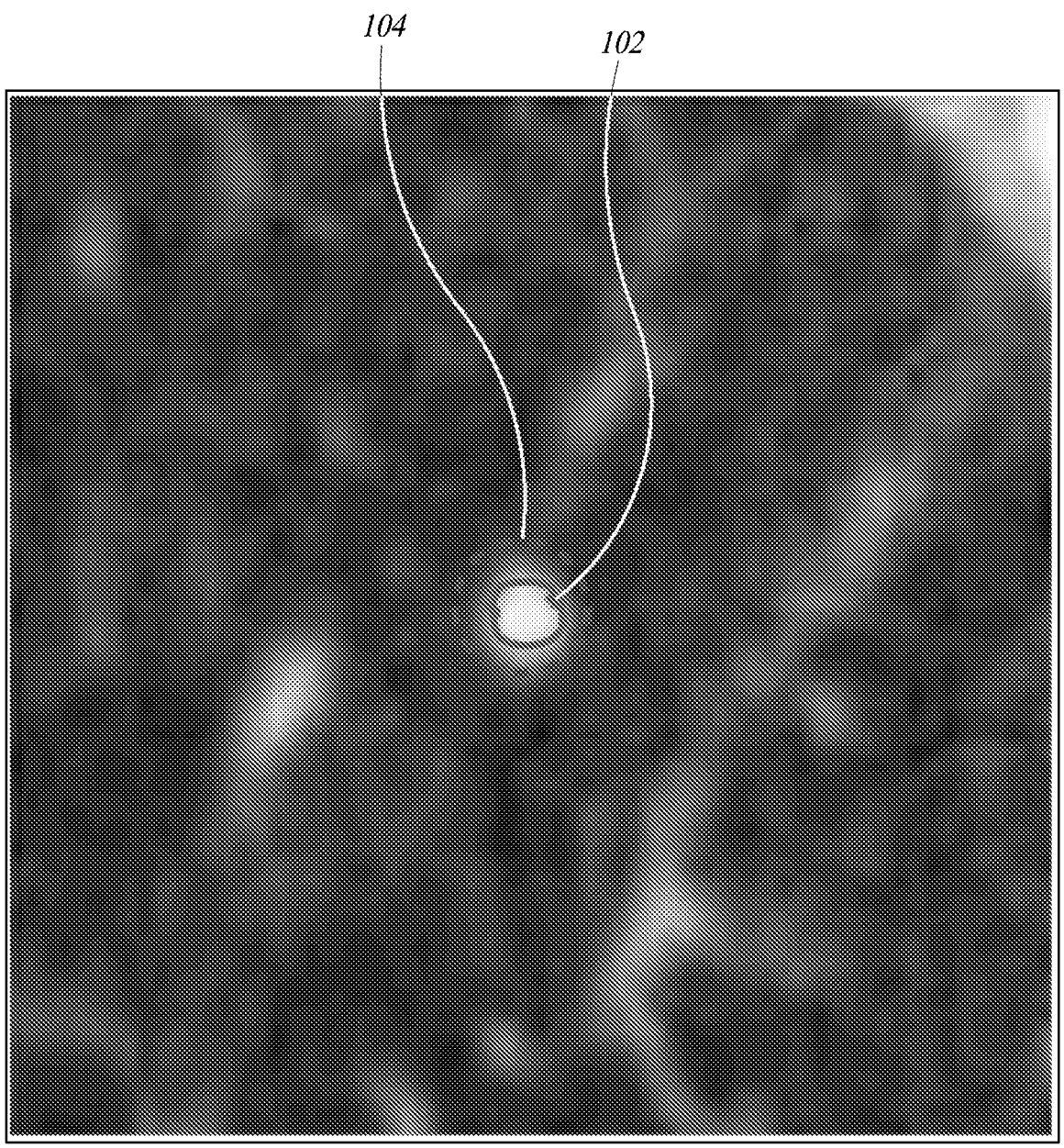
FIG. 1 is an image that displays the suboptimal results of the snakes algorithm on a small lesion.
Figure 2:
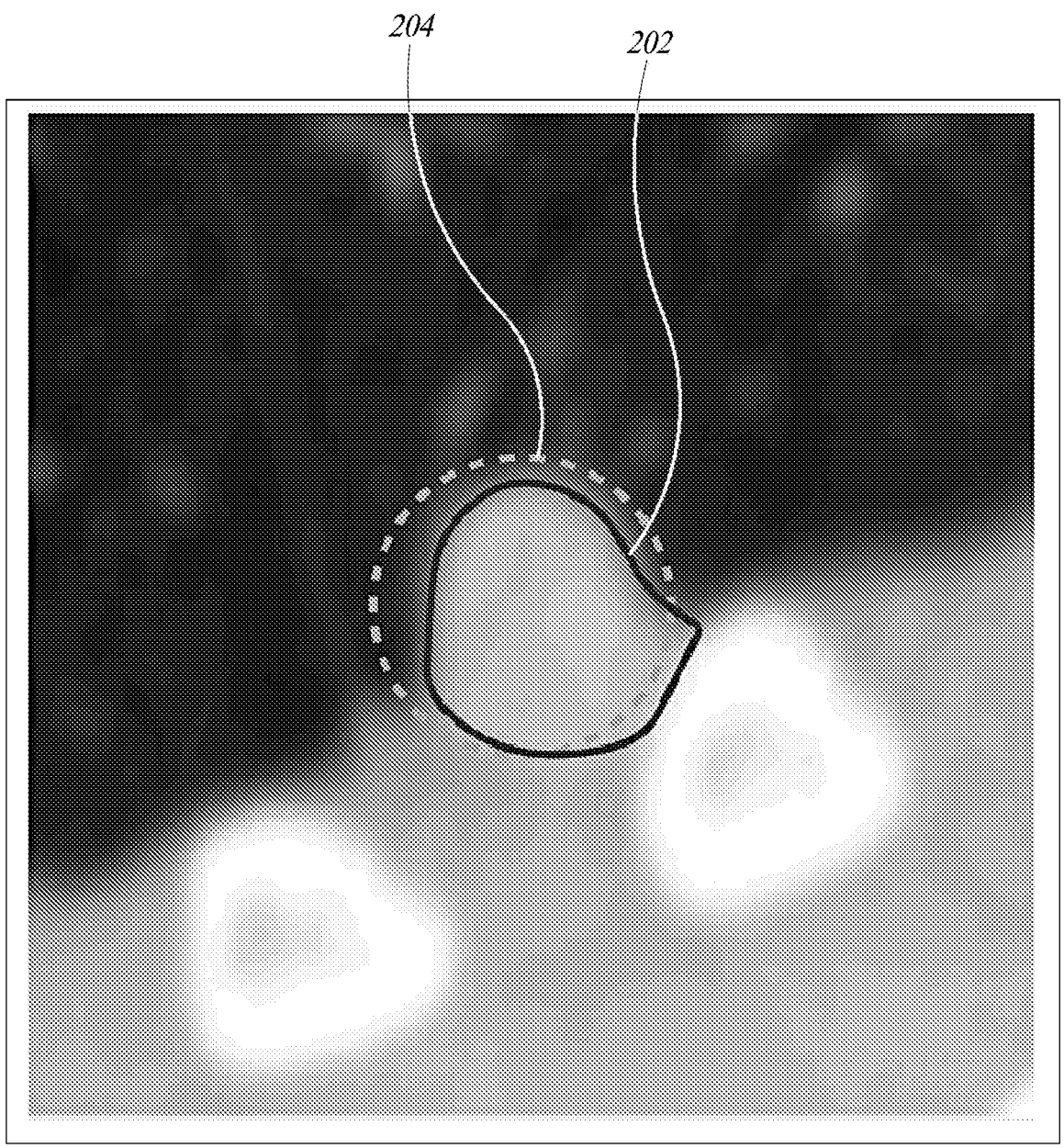
FIG. 2 is an image that displays the suboptimal results of the snakes algorithm on a juxtaplueral lesion.
Figure 3:
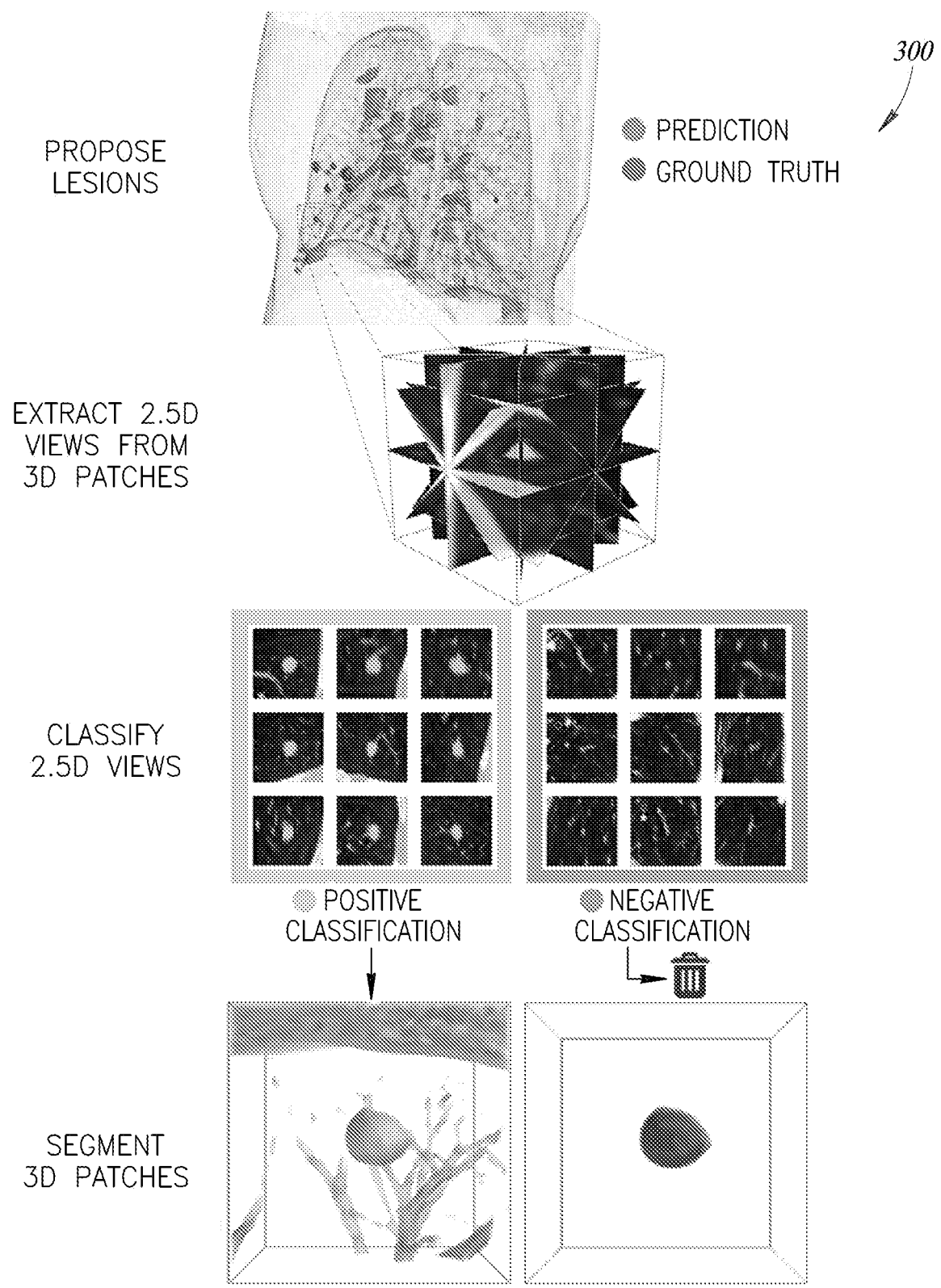
FIG. 3 is an image that displays the end-to-end detection, false-positive reduction, and segmentation pipeline in schematic form, according to one illustrated implementation.

FIG. 3 is a diagram 300 that visualizes an overview of a pipeline used to detect and segment lesions for a lung scan. This process uses a proposal network to suggest lesions candidates, optimizing for high sensitivity. A classification network sorts through all the lesion proposals, improving specificity (culling false positive proposals) while maintaining high sensitivity. A final network segments these proposals to calculate relevant diagnostic quantities to be presented to the user.

Co-registration of scans for machine learning purposes or longitudinal tracking of observations is also discussed.

Figure 4:
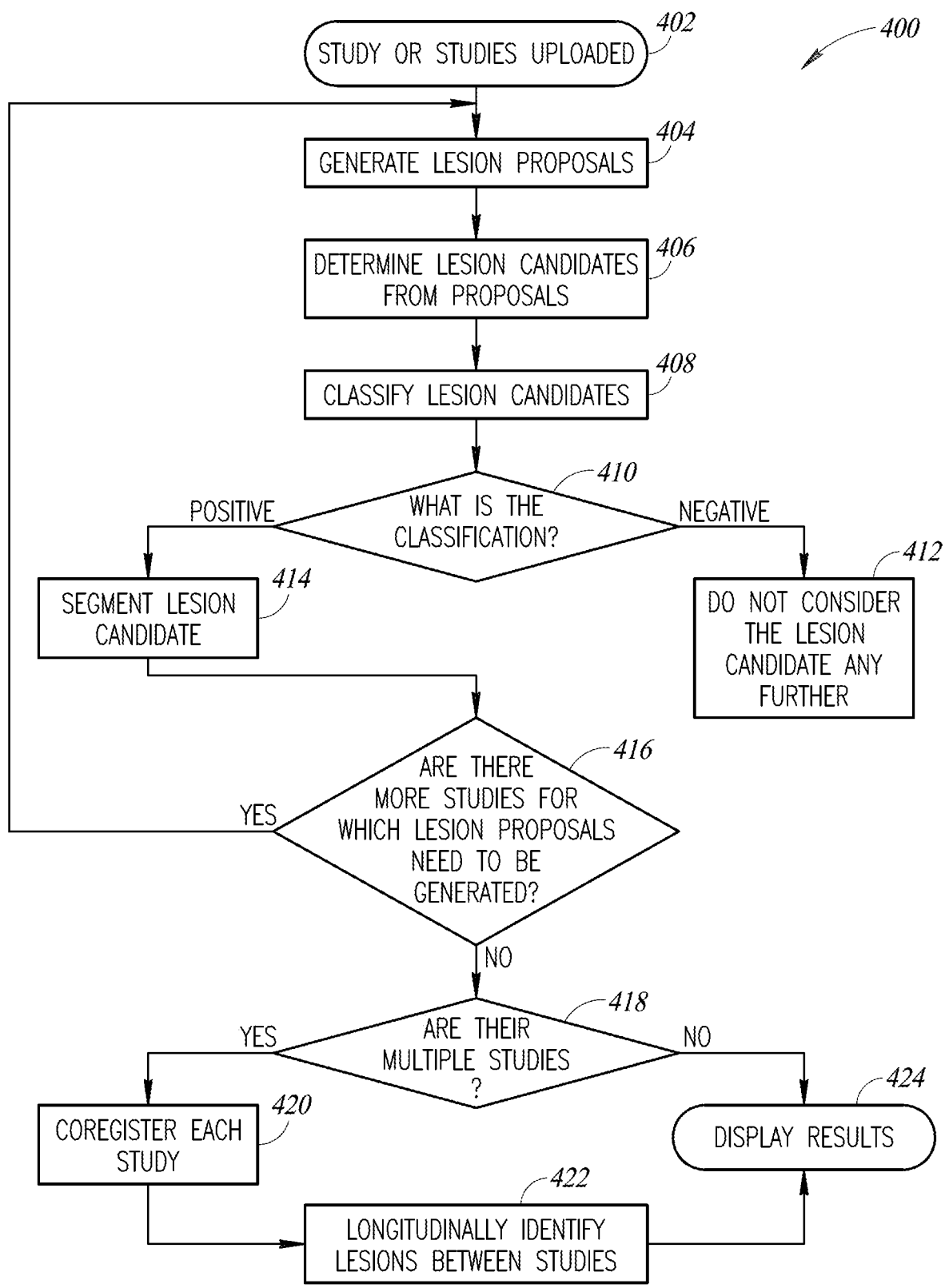
FIG. 4 is a flow diagram that displays the end-to-end detection, false-positive reduction, and segmentation pipeline, according to one illustrated implementation.
Figure 5:
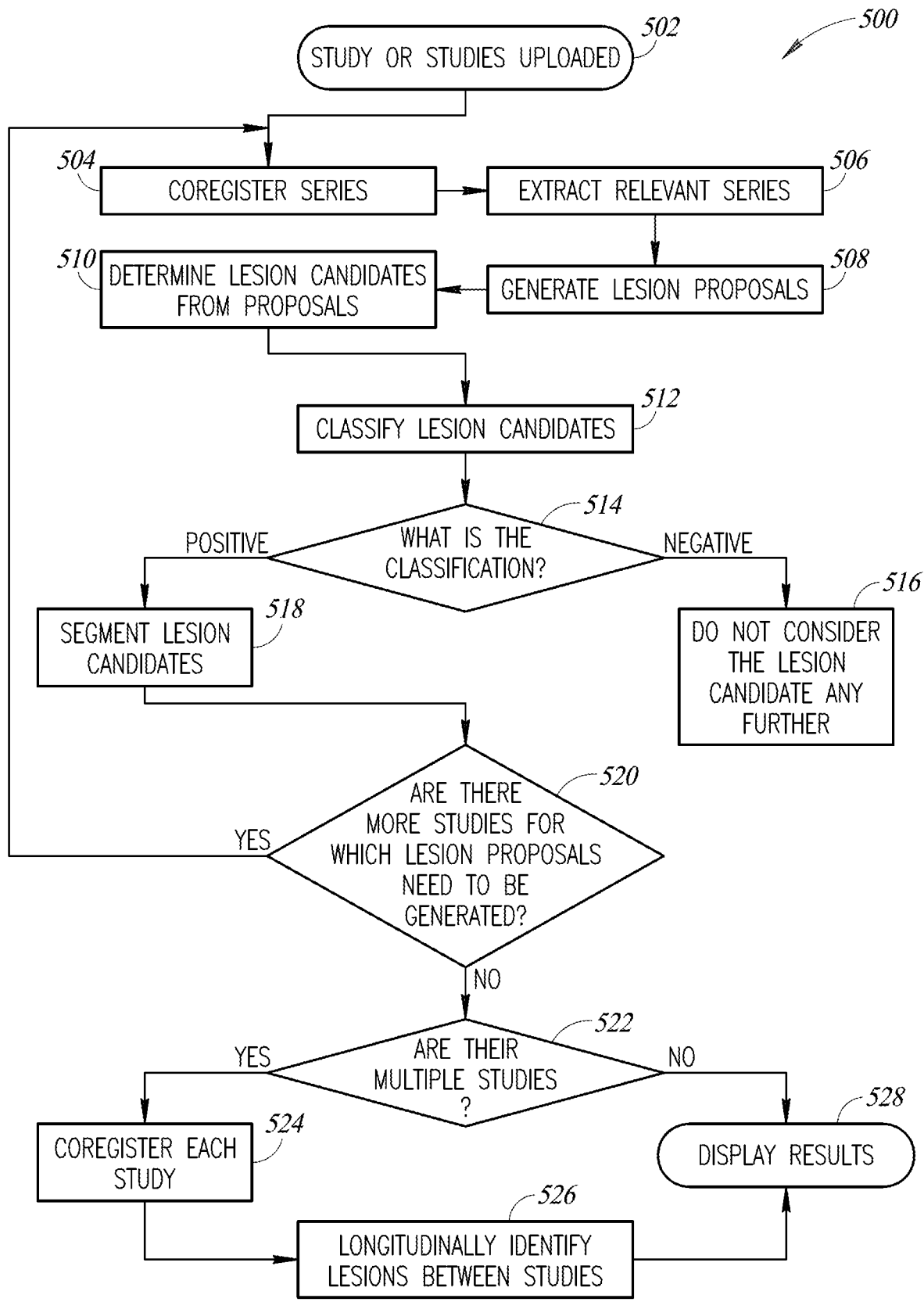
FIG. 5 is a flow diagram that displays the end-to-end detection, false-positive reduction, and segmentation pipeline for a case where each study has multiple series, according to one illustrated implementation.

A more general flowchart overview of the end-to-end pipeline for detection, segmentation, and co-registration of lesion candidates is detailed in FIGS. 4 and 5. FIG. 4 displays the pipeline for an input or inputs each with a single series (e.g., for lung lesion detection in CT), whereas FIG. 5 shows the pipeline for an input or inputs with multiple series (e.g., for liver lesion detection in MR). These figures provide context that will aid in understanding the other operational pieces discussed below.

Figure 11:
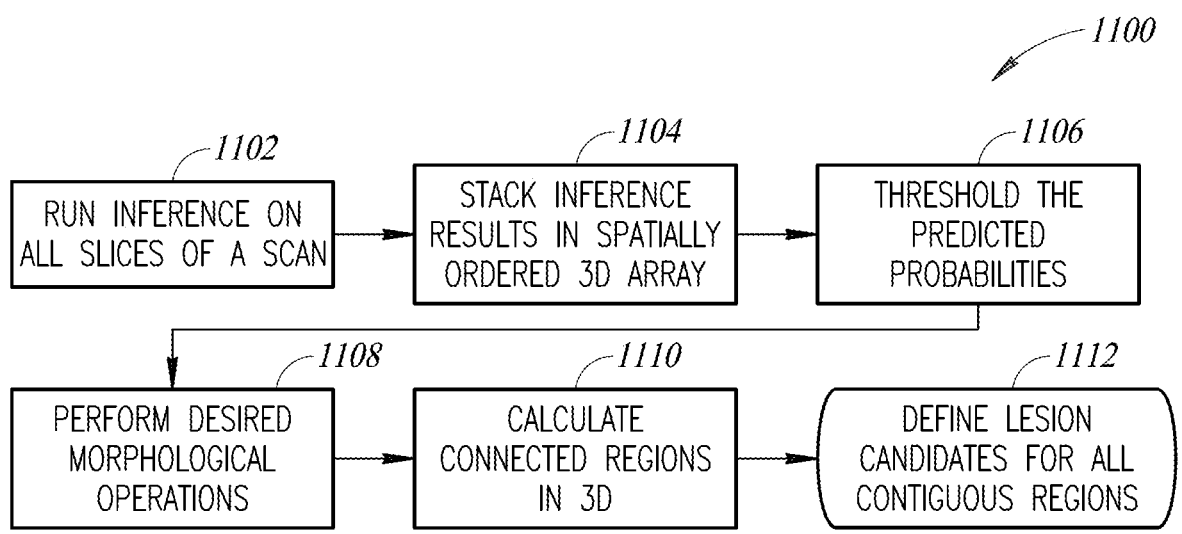
FIG. 11 is a flow diagram of the means by which inference results for a 2D proposal network are combined, according to one illustrated implementation.

For the pipeline wherein studies have a single series, the process 400 begins at 402 when a study or multiple studies are uploaded. The process 400 takes a study and generates lesion proposals at 404. From these proposals, lesion candidates are determined at 406 and classified as either a true positive (True) or false positive (False) at 408. Note that (404, 406) is described in further detail in FIG. 11. At 410, the system determines the classification of each module. For each lesion candidate, if the classification determined at 410 to be negative, it is not considered any further at 412. If the classification is positive, the lesion is segmented at 414. If there are further studies that have not been processed, which is determined at 416, steps 402-414 are repeated. If there are not any further studies to be processed, it is assessed whether there are multiple studies at 418. If there are not, the results are displayed at 424 on a display of the system. If there are multiple studies, they are co-registered at 420, and lesion candidates between each scan are longitudinally identified at 422, at which point the results are displayed at 424.

For the pipeline wherein studies have multiple series, the process 500 begins at 502 when a study or multiple studies are uploaded at 502. The process co-registers all available series at 504 and extracts the relevant series at 506 for generating lesion proposals at 508. From these proposals, lesion candidates are determined at 510 and classified at 512. Note that (508, 510) is described in further detail in FIG. 11. For each lesion, if the classification determined at 514 is negative, it is not considered any further at 516. If the classification determined is positive, the lesion candidate is segmented at 518. If there are further studies that have not been processed, which is determined at 520, steps 502-518 are repeated. If there are not, it is assessed whether there are multiple studies at 522. If there are not, the results are displayed 528. If there are multiple studies, they are co-registered at 524, and lesion candidates between each study are longitudinally identified at 526, at which point the results are displayed at 528.

Each of the methods of generating lesion proposals, classifying the proposals, and segmenting the lesions are all deep learning methods, and each utilizes its own training database with particular specifications. After the models are trained, they can be used for inference on new data. After inference is complete, and the lesion(s) are detected, co-registration is invoked if multiple scans for the same patient have been uploaded. Each of these steps will be discussed in order.

Training Databases

Each deep learning method utilized in the pipeline requires its own training database with particular specifications. Lightning Memory-mapped Databases (LMDBs) are utilized that store preprocessed image/segmentation mask pairs for training. This database architecture holds many advantages over other means of storing training data, including:

Mapping of keys is lexicographical for speed
Image/segmentation mask pairs are stored in the format required for training so they require no further preprocessing at training time
Reading image/segmentation mask pairs is a computationally cheap transaction The training data could have been stored in a variety of other formats, including named files on disk and real-time generation of masks from the ground truth database for each image. These methods would have achieved the same result, though they would likely have slowed down training.

Figure 6:
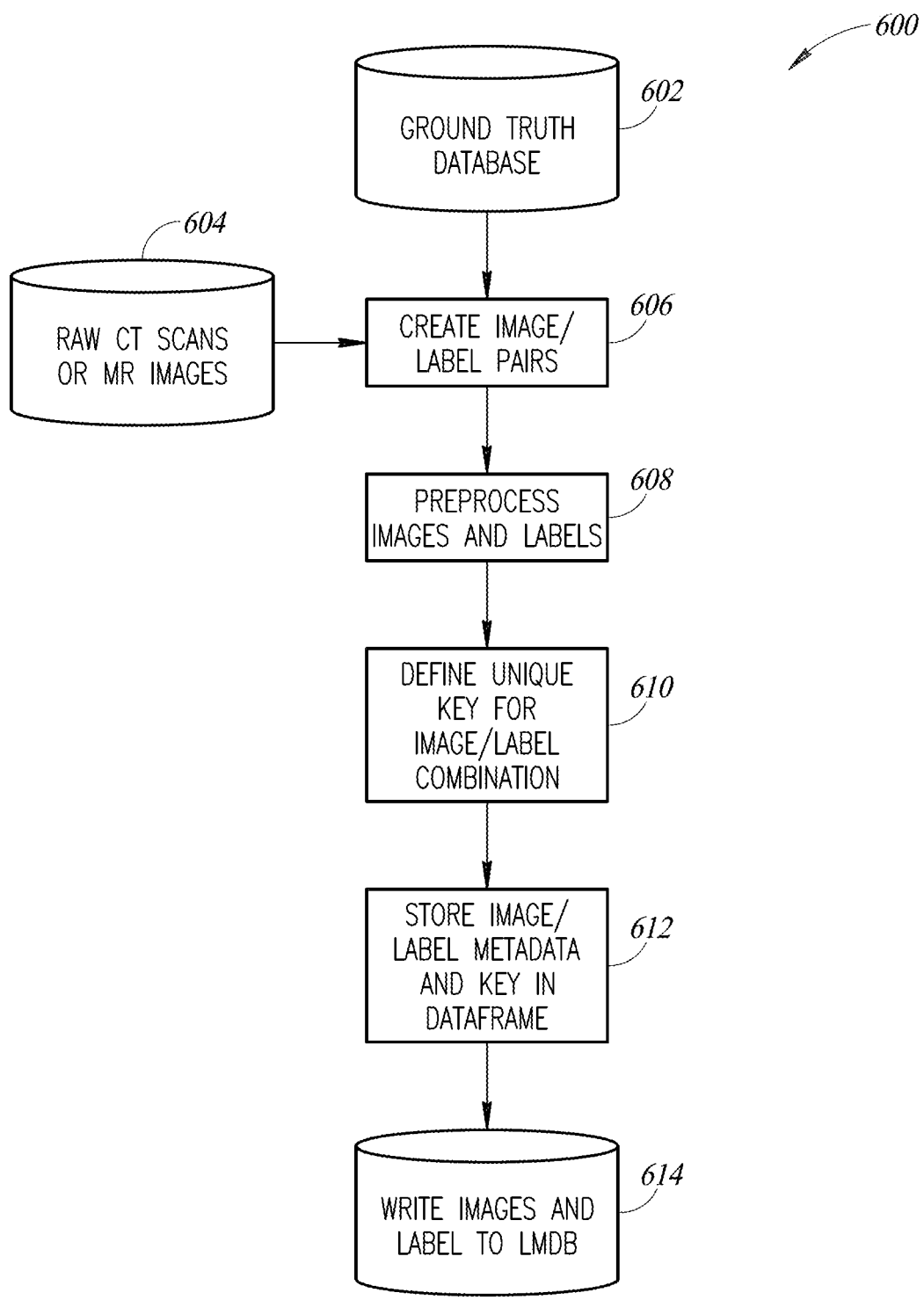
FIG. 6 is a flow diagram of the creation of a lightning memory-mapped database (LMDB) for training, according to one illustrated implementation.

Creation of a general LMDB is visualized in FIG. 6. The process 600 begins at 602 when the ground truth information is paired it with the pixel data from the corresponding scan at 604 to create image/label pairs from this information at 606. Preprocessing acts at 608 include normalizing the images, cropping the images, and resizing the images. If the label is a boolean mask, preprocessing also includes cropping and resizing.

A unique key for each image/label pair to be stored in the LMDB is defined at 610. The image and label metadata, including the slice index, lesion candidate location, and LMDB key are stored in a dataframe at 612. The preprocessed image and label are stored in the LMDB for each key at 614.

Network Training

Figure 7:
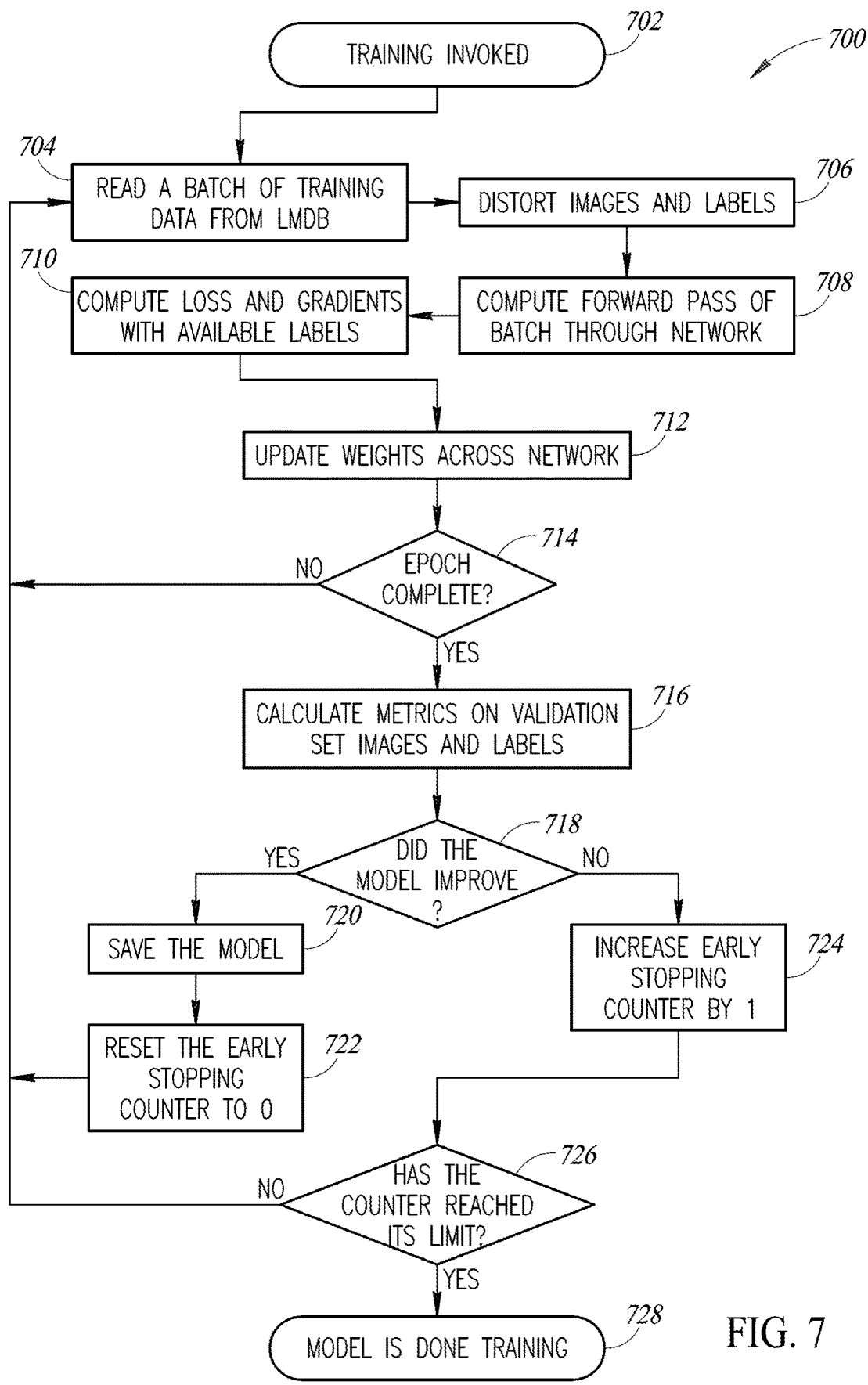
FIG. 7 is a flow diagram of the model training pipeline, according to one illustrated implementation.

FIG. 7 is a flowchart that describes general model training. An open-source wrapper built on TensorFlow called Keras is utilized in this disclosure for model training. However, equivalent results could be achieved using raw TensorFlow, Theano, Caffe, Torch, MXNet, MATLAB, or other libraries for tensor math.

The datasets are split into a training set, validation set, and test set; the training set is used for model gradient updates, the validation set is used to evaluate the model during training (e.g., for early stopping), and the test set is not used at all in the training process.

The process 700 begins at 702 when training is invoked. Image and mask data is read from the LMDB training set, one batch at a time at 704. The images and masks are distorted according to distortion hyperparameters in a model hyperparameter file at 706. The batch is processed through the network at 708, the loss/gradients are calculated at 710, and weights are updated as per the specified optimizer and optimizer learning rate at 712. Loss is calculated using a per-pixel cross-entropy loss function and the Adam update rule. For details of the Adam update rule, see Kingma, Diederik P. and Ba, Jimmy. Adam: A Method for Stochastic Optimization. arXiv:1412.6980 [cs.LG], December 2014.

At the end of every epoch at 714, metrics on the validation set at 716, including the validation loss, validation accuracy, relative accuracy vs. a naive model that predicts only the majority class, f1 score, precision, and recall. The validation loss is monitored to determine if the model improved at 718; if it did, the weights of the model are saved at that time at 720, and the early stopping counter is reset to zero at 722. Training begins for another epoch at 704. Metrics other than validation loss, such as validation accuracy, could also be used to indicate evaluate model performance. It is noted if the model didn't improve after an epoch by incrementing the early stopping counter at 724 by 1. If the counter has not reached its limit at 726, training begins for another epoch at 704. If the counter has reached its limit, training of the model is stopped at 728. This "early stopping" methodology is used to prevent overfitting, but other methods of overfitting prevention exist, such as utilizing a smaller model, increasing the level of dropout or L2 regularization.

At no point is data from the test set used when training the model. Data from the test set may be used to show examples of segmentations, but this information is not used for training or for ranking models with respect to one another.

Network Inference

Inference is the process of utilizing a trained model for prediction on new data. A web app is utilized for inference. Once the study is uploaded to the web app, the entire pipeline of detection and segmentation will be run, and co-registration will occur if multiple scans for the same patient are linked. The predicted lesion locations and segmentations are stored at that time and displayed to the user when they open the study.

For each part of the pipeline described in FIG. 4 that includes a neural network, the inference service is responsible for loading a model and generating output. The final segmentation network is responsible for generating the mask that will be displayed to the user.

Figure 8:
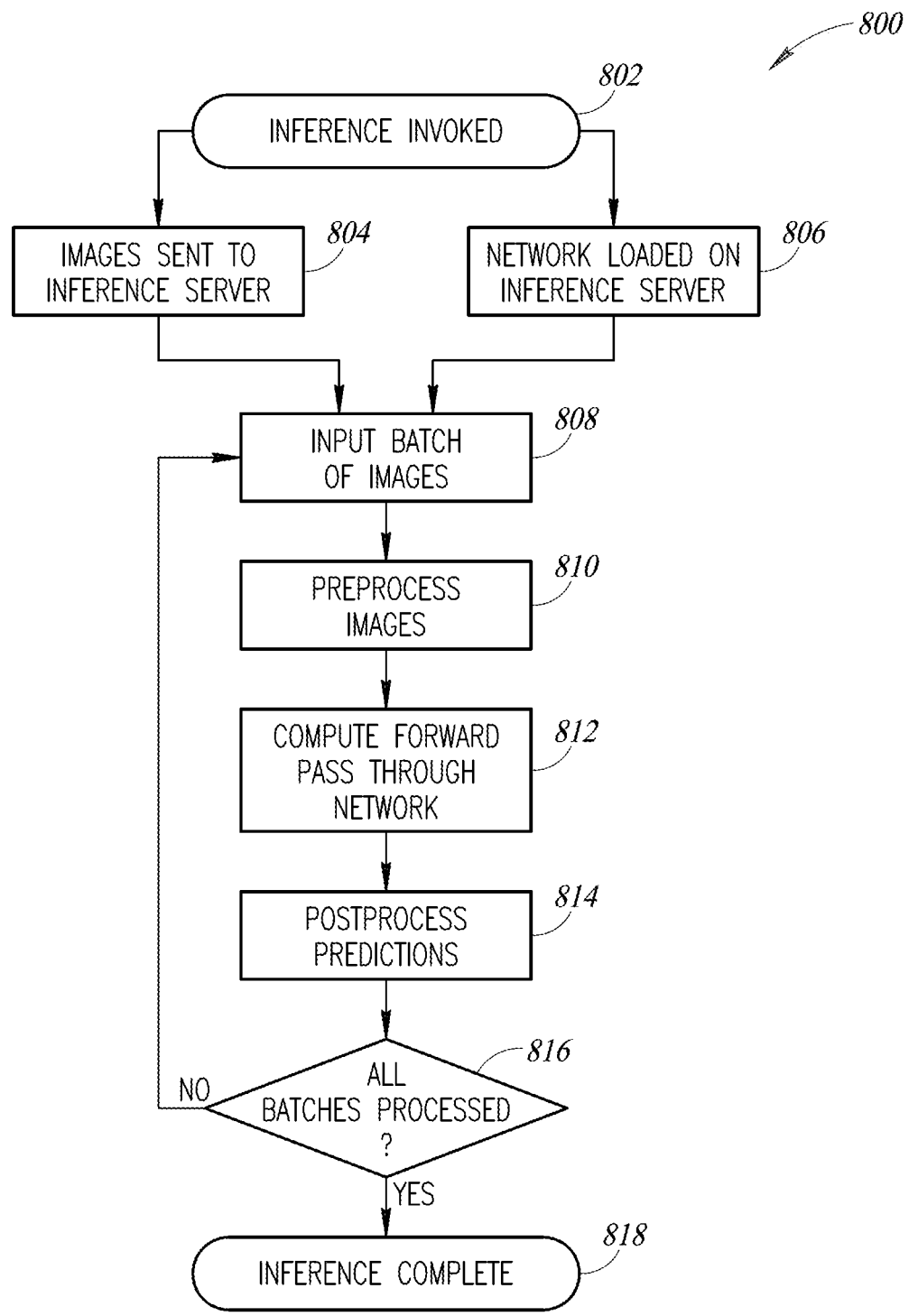
FIG. 8 is a flow diagram of the model inference pipeline, according to one illustrated implementation.

The general inference pipeline for each model is described in FIG. 8. The process 800 begins at 802 when inference is invoked. Images are sent to an inference server at 804 and the network is loaded on the inference server at 806. The production model that is used by the inference service has been previously hand-selected from the corpus of models trained during hyperparameter search; it is chosen based on the optimal tradeoff between accuracy, memory usage and speed of execution. The user may alternatively be given a choice between a "fast" or "accurate" model via a user preference option.

One batch of images at a time is processed by the inference server at 808. The images are preprocessed (normalized, cropped, etc.) using the same parameters that were utilized during training at 810. Inference-time distortions may also be applied to take the average inference result on, e.g., 10 distorted copies of each input image; this would create inference results that are robust to small variations in brightness, contrast, orientation, etc.

For a given image, a segmentation model generates probabilities for each pixel during the forward pass at 812, which results in a set of probability maps with values ranging from 0 to 1. The probabilities correspond to whether each pixel is part of a possible cancerous anatomical structure. The probability maps are transformed into a label mask, wherein all pixels with a probability above 0.5 are set to "potentially cancerous" and all pixels with a probability below 0.5 are set to background at 814.

For the classification model, a forward pass at 812 results in a probability score on whether the entire input image contains in it a possibly cancerous anatomical structure.

If not all batches have been processed as is determined at 816, a new batch is added to the processing pipeline at 808 and steps 810-814 are repeated until inference has been performed for all required inputs as determined at 816. Inference is complete at 818.

There are many reasonable physical constraints that should be satisfied for accurate segmentation. These include, for example, that segmentations of cancerous anatomical structures of the liver do not occur outside of the physical bounds of the liver, that cancerous anatomical structures of the lungs do not occur outside of the physical bounds of the lungs, and that cancerous anatomical structures of the given organ are not larger than the given organ.

Once the label mask has been created, to ease viewing, user interaction, and database storage, the mask may be converted to a spline contour for each axial slice. The first step is to convert the mask to a polygon by marking all the pixels on the border of the mask. This polygon is then converted to a set of control points for a spline using a corner detection algorithm. For details of this algorithm, see Rosenfeld, Azriel, and Joan S. Weszka. "An improved method of angle detection on digital curves." IEEE Transactions on Computers 100.9 (1975): 940-941. A typical polygon from one of these masks will have hundreds of vertices. The corner detection attempts to reduce this to a set of approximately sixteen spline control points. This reduces storage requirements and results in a smoother-looking segmentation. These splines are stored in a database and displayed to the user in the web app. If the user modifies a spline, the database is updated with the modified spline.

Volumes may be calculated by creating a volumetric mesh from all vertices for a given time point. The vertices are ordered on every slice of the 3D volume. An open cubic spline is generated that connects the first vertex in each contour, a second spline that connects the second vertex, etc., for each vertex in the contour, until a cylindrical grid of vertices is created that is used to define the mesh. The internal volume of the polygonal mesh is then calculated.

Alternatively, for small or complex lesions, a spline may be too coarse of a representation to fully capture the structure of the lesion. In this case, the mask may be created and stored as a pixel mask without being converted to a spline. Volumes may be calculated by counting the voxels within the 3D mask and multiplying by the volume of each voxel in mL or $mm^3$. Alternatively, volumes can be calculated using a shape prior for the given lesion.

Proposal Network

In this disclosure, a fully convolutional network (FCN) is utilized for segmentation to locate as many lesion candidates as possible. This FCN is tuned to maximize lesion sensitivity rather than specificity; it is left to the second piece of the pipeline, the classification network, to reduce the number of false positives from the proposal network.

Various styles of FCN may be chosen, as long as the FCN performs pixelwise segmentation. Possible segmentation architectures include but are not limited to ENet, U-Net, and their variants. Detailed discussion of these FCN architectures is presented in a later section. In this disclosure, 2D or 3D FCNs are utilized. 2D networks train more quickly than their 3D extensions and have lighter computational requirements, but 3D networks incorporate more spatial context. Dimensionality of the neural network is chosen via a hyperparameter search.

If a 2D network is chosen, it is generally used on axially acquired images, as scan resolution is often highest in the xy plane; however, the 2D FCN could also be trained and validated on any reformat or acquired plane of the data, including the coronal or sagittal planes.

If the image data are from CT scans, the data are clipped with a lower limit of −1000 Hounsfield units and an upper limit of 400 Hounsfield units before normalizing such that they have a mean of 0, though other clip values that contain the full range of lesion brightnesses would suffice. MRIs are normalized such that they have a mean of zero and that the 1st and 99th percentile of a batch of images fall at −0.5 and 0.5, i.e., their "usable range" falls between −0.5 and 0.5.

Both 2D and 3D networks are applied to the full input image for a particular model if there is sufficient GPU memory. If not, the input image can be downsampled (e.g., a 512×512 pixel image to a 256×256 pixel image for the 2D case) or the FCN can operate on patches of the high resolution data, either in a non-overlapping fashion (e.g., a 512×512 pixel image is split into 256×256 pixel images with stride 256, resulting in four total images in the 2D case) or an overlapping fashion (e.g., a 512×512 pixel image is split into 256×256 pixel images with stride 128, resulting in sixteen total images in the 2D case).

To achieve a high sensitivity with the proposal network, the loss function is modified to increase the penalty of prediction errors in portions of the image containing pixels annotated to be lesion candidates by clinicians and reduce the penalty of prediction errors in the background of the image. The modified training function comprises convolving the ground truth label map with a Gaussian kernel. Furthermore, the modified training function has as a hyperparameter the ratio of total weight given to foreground and background pixels.

To further increase the sensitivity of the proposal network, multiple models trained in different ways are ensembled, as each model may pick up on different "flavors" of possibly cancerous anatomical structure. There are many different ways to ensemble models. The inventors found that the most effective combination involves combining the predictions from a model trained with a modified loss function and one trained with a classic pixel-wise binary cross-entropy. However, other means of ensembling predictions could include but are not limited to combining the results of 2D FCNs trained on each of axial, coronal, and sagittal slices of the volumetric data and ensembling different model architectures, including combinations of 2D and 3D models.

An optional preprocessing step includes reformatting the data to be the intensity projection along any axis. In lung CT, blood vessels appear more elongated in an intensity projection, whereas lesions generally don't appear more elongated. The intensity projection can be the mean, maximum, or minimum. In this framework, the intensity projection and non-projected image data are used as inputs into the model and the feature maps for the two data types are combined via concatenation, sum, difference, or average.

Multi-modal data for training the models is utilized in cases where it is available, e.g., in liver MRIs. These scans are co-registered before utilizing this data. There are many possible ways of combining different series, including but not limited to including each series as a channel and including each series as a separate input and fusing the latent feature maps. Traditional neural networks typically have one channel of input or channels that represent RGB colors. By utilizing the different series as neighboring channels, the network is able to learn spatially-coherent intensity correspondences between the pulse sequences. If each series is included in a separate input, the network learns unique features for each before they are combined to make a final segmentation or classification.

A CNN that directly predicts the content of bounding boxes corresponding to features in the input image may also function as the proposal network. Two-stage bounding box prediction networks, wherein the first stage suggests locations of reasonable bounding boxes and the second stage classifies these bounding boxes, have been shown to succeed at a variety of detection tasks. However, these algorithms tend to be slow and require custom fine-tuning to work.

A one-stage bounding box detection system that operates on a dense grid of candidate bounding boxes has recently been proposed by [Ysung-Yi 2017]; the authors describe a modified cross-entropy loss to sort through the highly unbalanced classes, as most candidate boxes will be in the background class. Their one-stage detection system and custom "focal loss" may be extended to a 3D analogue tuned for nodule detection, except for one notable distinction: a dense sampling of candidate bounding boxes in 3D mandates an exceptional number of candidates. In this disclosure, the inventors utilize the general structure outlined by [Ysung-Yi 2017] for purposes of nodule detection, but modify the anchor sampling strategy. We observe that large anchors, when densely sampled, have extremely high IoU with one another, resulting in an unnecessarily high computational burden; as such, we spread larger candidate bounding boxes with a multi-pixel stride while still maintaining dense sampling for smaller candidates. Both the baseline 2D approach and 3D extension to published work are considered.

Proposal Network Training Database

Figure 9:
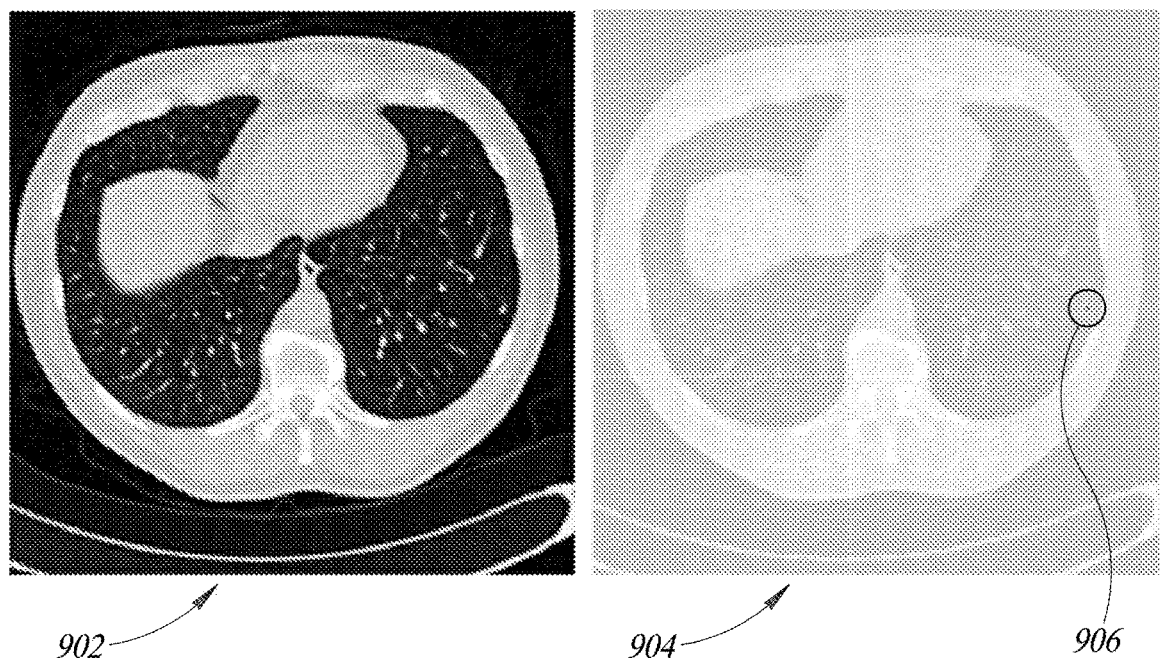
FIG. 9 is an image that displays an example from the proposal network training database, according to one illustrated implementation.

For the proposal network, a ground truth database includes lesion segmentations that are paired with the raw CT or MR images on an axial slice-by-slice basis (for the 2D case) or with the entire scan (for the 3D case) to create image/label mask pairs. For the 2D case, only axial slices that intersect a lesion segmentation are included, though other slices could have been included. The unique LMDB key is a concatenation of the series UID and the slice index, though other unique keys would have sufficed. FIG. 9 displays an image/label pair (902 and 904, respectively) for the proposal network training database. The ROI is in the black box 906. For the case wherein a bounding box detection network is utilized, the ground truth database includes the bounding boxes described by the lesion segmentations.

Proposal Network Training

In order to maximize lesion recall, the 2D version of the proposal network is trained only on slices that intersect a lesion. Although this will result in an over-proposing of lesions at inference time, as real scans do not have lesions on every slice, the subsequent classification network sorts out the false proposals.

Figure 10:
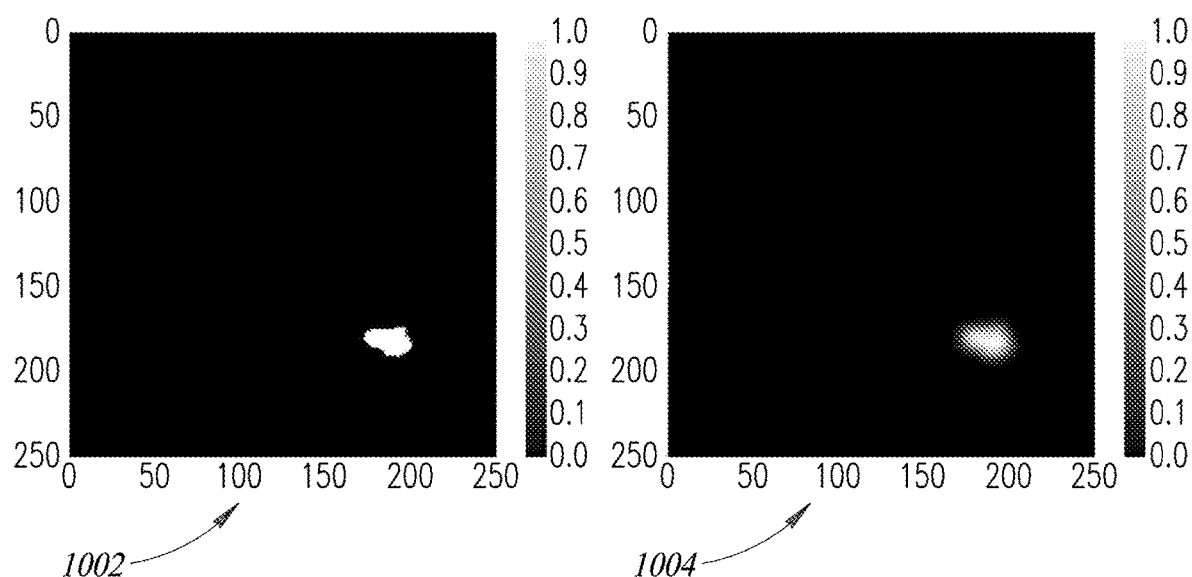
FIG. 10 is an image that displays the method by which the ground truth map is adjusted for training, according to one illustrated implementation.

The training loss function is modified to preferentially penalize prediction errors in the vicinity of the lesion candidate and reduces the penalty of prediction errors in the background of the image. The modification involves convolving a Gaussian kernel with the ground truth segmentations. The width and strength of the kernel are hyperparameters. This is visualized in FIG. 10. Image 1002 shows the ground truth map before convolving with a Gaussian kernel, image 1004 shows after convolving with a Gaussian kernel.

The kernel used in this example has a width of 15 pixels and has been normalized such that the peak value is 100.

A plurality of models is optionally utilized, in which case the results are ensembled. In this case, the best model trained with this modified loss function (as determined in a hyperparameter search) and the best model trained with a pixelwise cross-entropy loss (as determined in a separate hyperparameter search) are ensembled to use for inference and for creating the classification network training database.

Proposal Network Inference

Figure 12:
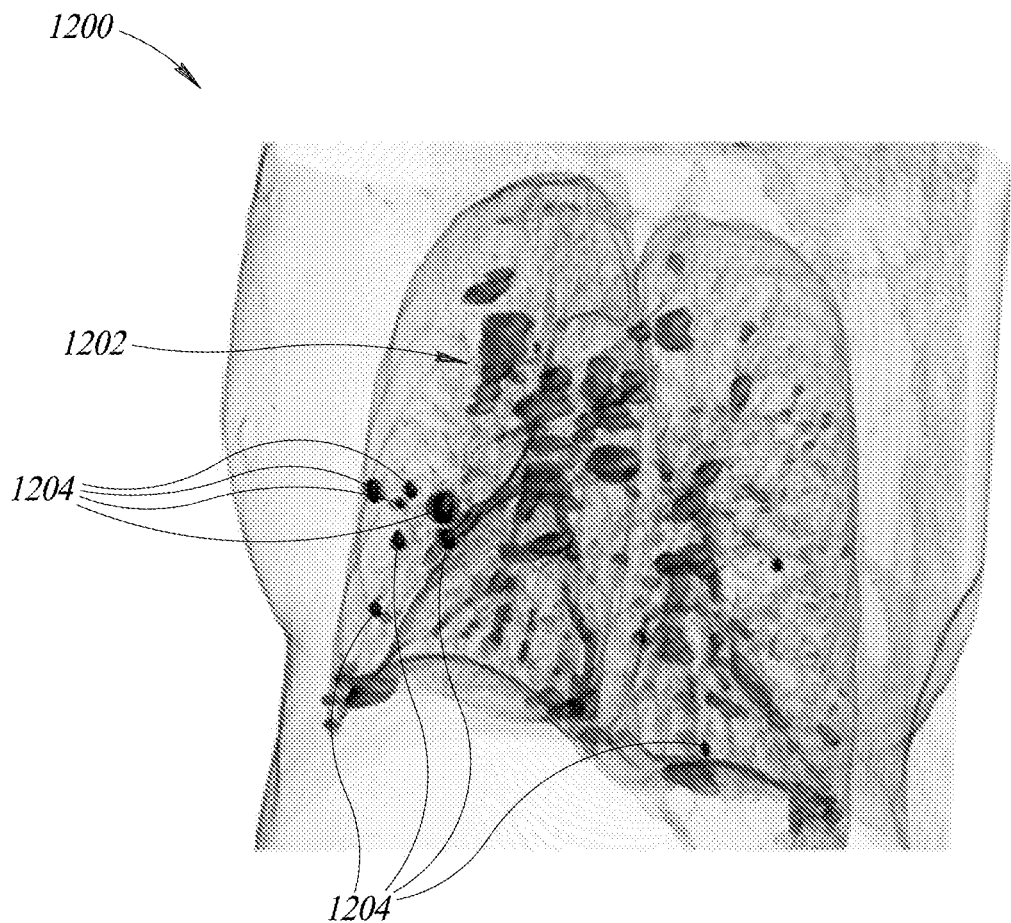
FIG. 12 is an image that displays a 3D render of a lung scan showing both proposed and ground truth lesion candidates.

In the implementation wherein a 2D FCN is used on slices of the volumetric image data, the process 1100 begins at 1102 when inference is run for each slice. The proposals are stacked in a spatially ordered 3D array at 1104. The predicted probabilities are thresholded at 1106, and any desired morphological operations are utilized at 1108. Morphological operations may include dilation, erosion, opening and closing. These predictions are then combined in 3D utilizing 6, 18, or 26-connectivity of the predicted pixels at 1110, for example. The centroid of each connected prediction is defined to be the center of mass of predicted probabilities, the center of the binarized mask, the center of the circumscribing bounding box, or the random location within the segmentation, among other options. Lesion candidates are defined for all contiguous regions as 1112. FIG. 12 displays a 3D render 1200 of both proposed 1202 and ground truth 1204 lesion candidates after all 2D axial proposals have been combined and processed.

Classification Network: False Positive Reduction

While the proposal network is able to achieve high lesion sensitivity, it does so with a very low specificity. To reduce the number of false positives while maintaining high sensitivity, a classification network is utilized to sift through all proposals and learn the difference between true and false lesions.

There are many popular CNN architectures for classification that have been discussed in the literature. For this disclosure, a modified ResNet is used. For a detailed description, refer to the "ResNet Variation" section below.

Image planes centered on the lesion center that are evenly distributed in solid angle over each axis to create a 2.5D view of the lesion are extracted and stacked as channels for input to the network. This allows us to consider 3D context while making classifications on hundreds of lesion candidates per scan in a reasonable amount of time. However, in other implementations a 3D classification architecture may be used for this purpose. A 3D architecture would likely be more accurate, at the expense of being significantly more computationally intensive.

To further increase the classification accuracy of the model, an intensity projection could be used for some subset of the channels of the 2.5D view.

To learn features at a variety of spatial scales, the input data are resampled to different real-world spacing per pixel and combine the learned latent features.

Classification Network Training Database

Figure 13:
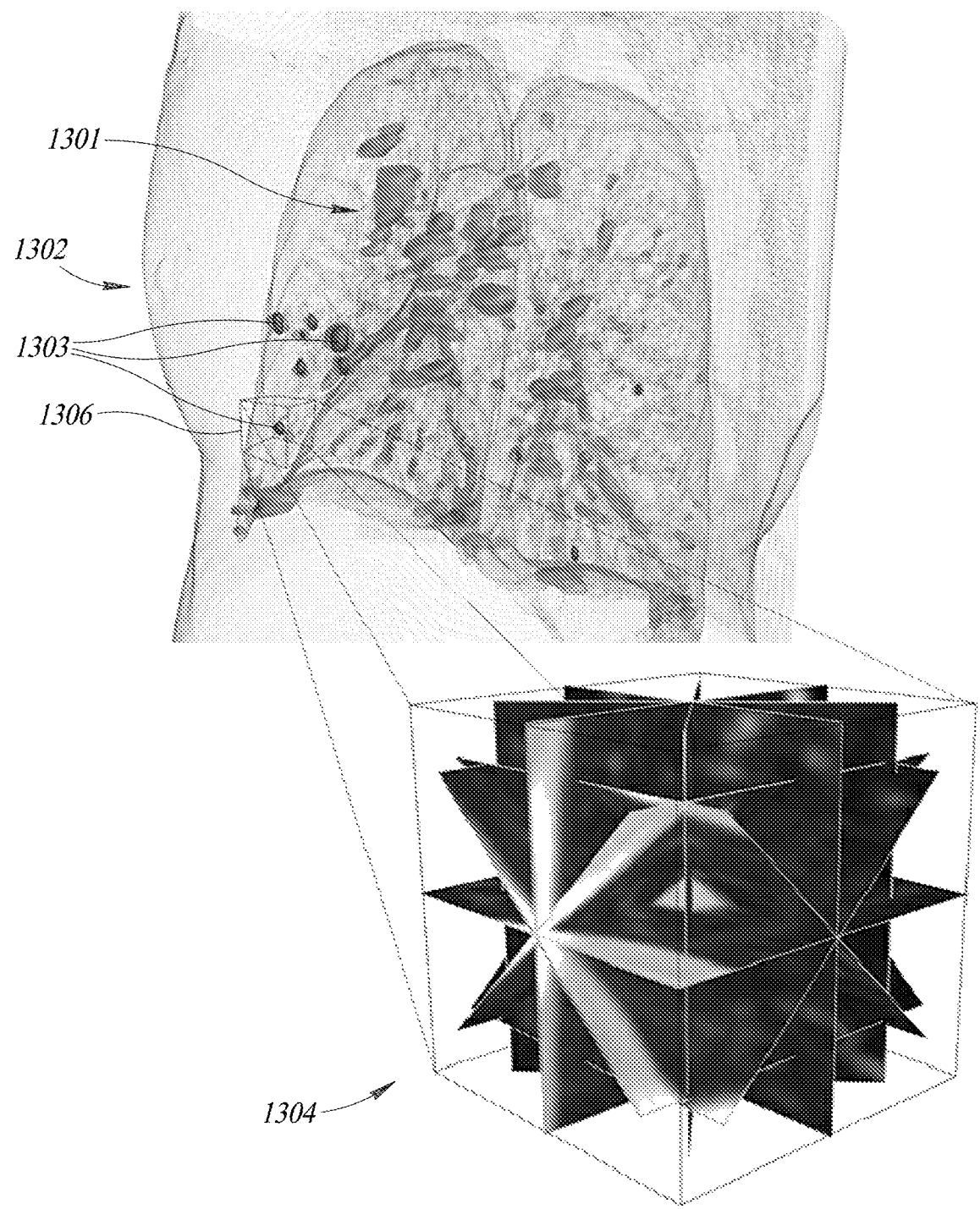
FIG. 13 is an image that displays a 3D render of a lung scan and how a multi-plane view is extracted for a specific nodule, according to one illustrated implementation.

The classification network's training database is built with the results from the proposal network. The proposed segmentations are combined in 3D and the centroid of each connected region is calculated. If the centroid falls within the segmentation mask, the image extracted at this centroid will be a true case in the database, whereas if it falls outside of a ground truth segmentation mask, it will be a false case. The images utilized for training the classification network are extracted from the raw CT scans or MRIs for each centroid. Planes evenly distributed in angle along each primary axis are extracted. This process is visualized in FIG. 13, wherein a 3D render 1302 of a CT lung scan with proposed 1301 and ground truth 1303 lesions and the 9-plane view 1304 extracted for one specific lesion candidate in the box 1306. The images extracted for the lesion candidate are evenly distributed in angle (by 45 degrees for a 9-plane view) along each of the x, y, and z axes.

Figure 14:
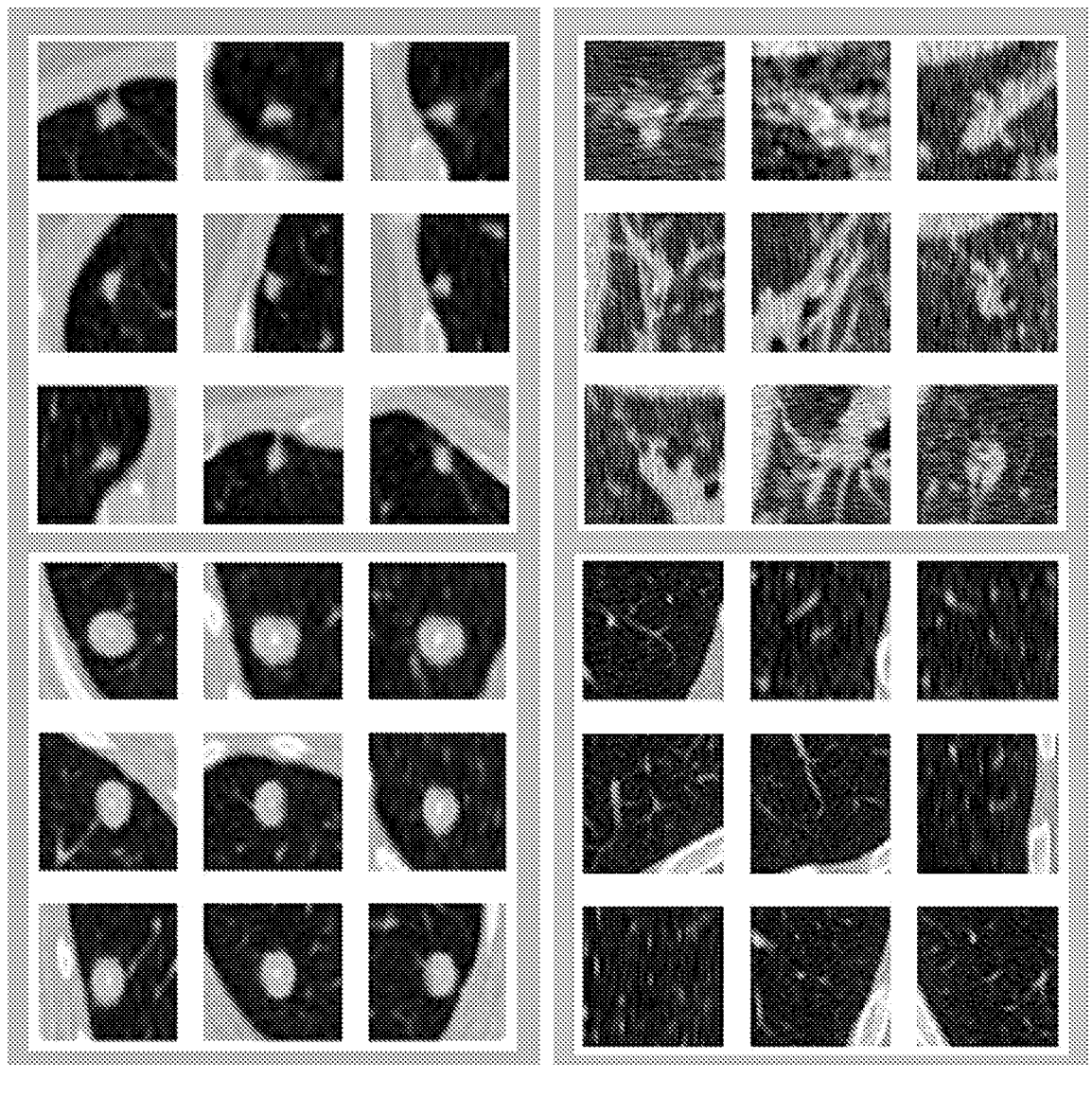
FIG. 14 is an image that displays two randomly selected true cases and two randomly selected false cases from the classification network training database.

These images are stored in a single array where the channel dimension are combined with the classification label. The unique key used in the LMDB is the lesion location, though other unique keys could also be used. FIG. 14 displays two randomly selected true cases 1402 and false cases 1404 pulled from the classification network training database for the 9-planes variation.

Classification Network Training

The classification network is trained as described in the general framework. However, because there may be hundreds of false proposals for every positive proposal, dataset rebalancing is used during training. The ratio of negative to positive lesions is a hyperparameter. Samples are randomly selected from all the negative proposals until the desired ratio is achieved. Furthermore, the change in the ratio of negative to positive lesion images with each epoch is a hyperparameter. Having this option allows the strong oversampling of positive candidates during the beginning of training for the network to learn the characteristics of positive lesions, followed by an annealing of the ratio towards the original distribution such that the network can learn the native distribution of classes in the data.

Classification Network Inference

Figure 15:
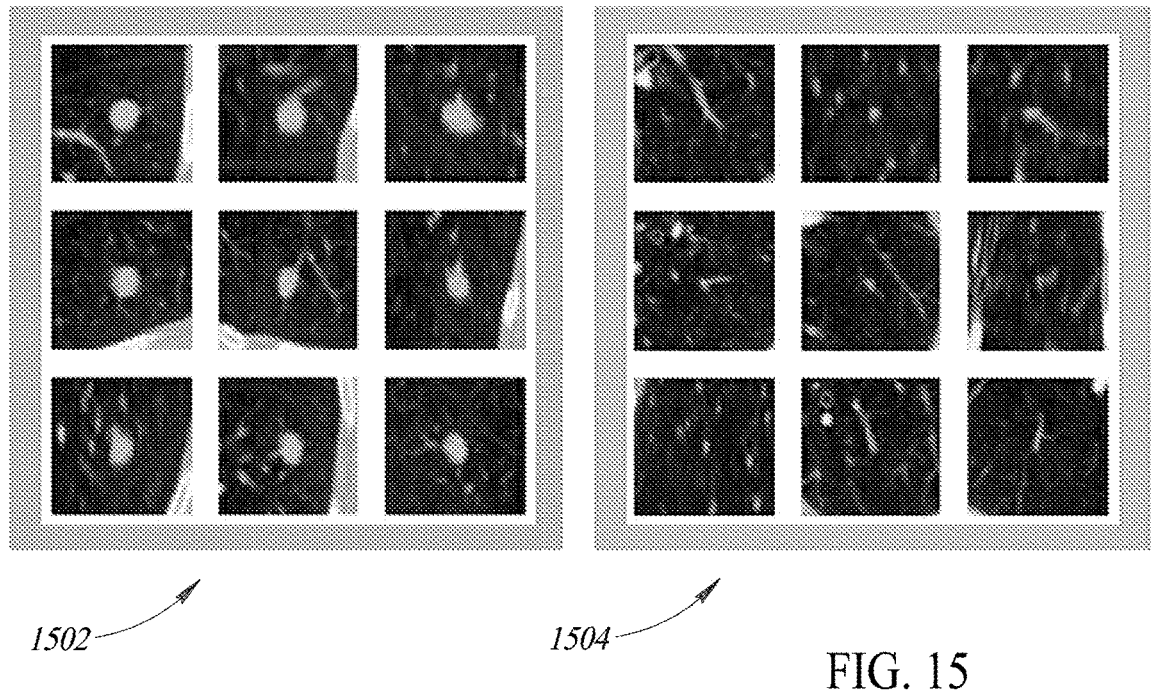
FIG. 15 is an image that displays inference results for two selected cases from the classification network training database.
Figure 16:
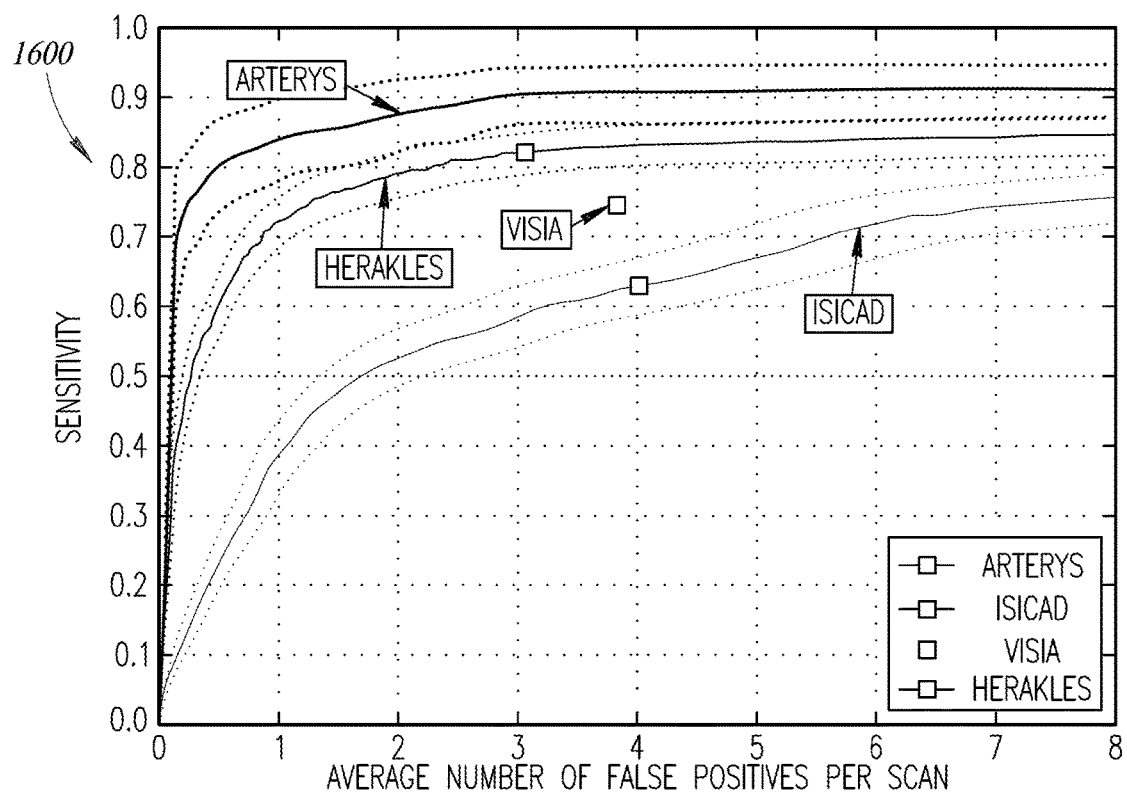
FIG. 16 is an image that displays the lesion detection sensitivity vs. average number of false positives per scan for lung lesion detection using the combination of the proposal and classification networks for a lesion detection system of the present disclosure vs. other clinical CAD products, according to one illustrated implementation.

FIG. 15 displays inference results for the classification network of a true positive 1502 and true negative 1504 case. FIG. 16 is a graph 1600 that displays the lesion detection sensitivity versus average number of false positives per scan for lung lesion detection using the combination of the proposal and classification networks for the lesion detection system discussed in this disclosure versus other clinical CAD products, according to one implementation.

Segmentation Network

Lesion candidates that are classified as true lesions will be segmented via patches that are extracted from the full resolution images. Having a dedicated segmentation network that operates on patches is advantageous over a network that operates on the entire image at once. The percentage of foreground pixels in a patch is much higher relative to a full resolution image, allowing faster training. Furthermore, this implementation does not require complicated custom loss functions. Furthermore, a patch based method allows the use of a 3D end-to-end segmentation model, as memory limits are not reached with small patches.

The segmentation methodology of the present disclosure utilizes customized fully convolutional neural networks for end-to-end 3D training and segmentation. This deep learning approach is able to learn a huge number of features representative of the training data presented to it, resulting in superior generalization performance. Furthermore, the network is able to consider full spatial context for all lesion candidates that need to be segmented at the intrinsic resolution of the scan.

As with the proposal network, the exact FCN that is used for segmentation may vary as long as it performs pixelwise segmentation. 3D extensions of ENet, U-Net, and their variants are all possible.

The segmentation network may additionally contain a Spatial Transformer Network (STN) module, a subnetwork structure that allows for the spatial manipulation of data. STNs take as input the data to transform, and produce the parameters necessary to perform a pre-determined spatial transformation such as, but not limited to, rotation or scaling. STNs can produce varying types of transformations that allow for rigid or non-rigid spatial manipulation, and include but are not limited to affine transformations, thin plate spline transformations, b-spline transformations, and projective transformations.

When inserted into an existing CNN, STN modules allow for the network to increase its invariance to translation, scaling, rotation, and more generic warping. STN modules may be inserted at the beginning of a CNN, acting on the input and manipulating it in such a way that it is easier for the CNN to perform its task (e.g. classification or segmentation). They can also be inserted anywhere within a CNN to manipulate the intermediate feature maps such that the CNN can more easily perform its task.

For semantic segmentation, scale invariance is often a challenge that CNNs struggle with. Spatial transformer networks parametrized to perform zoom/attention operations can improve the scale invariance of a CNN by allowing the network to focus on the relevant features for segmentation.

Segmentation Network Training Database

Figure 17:
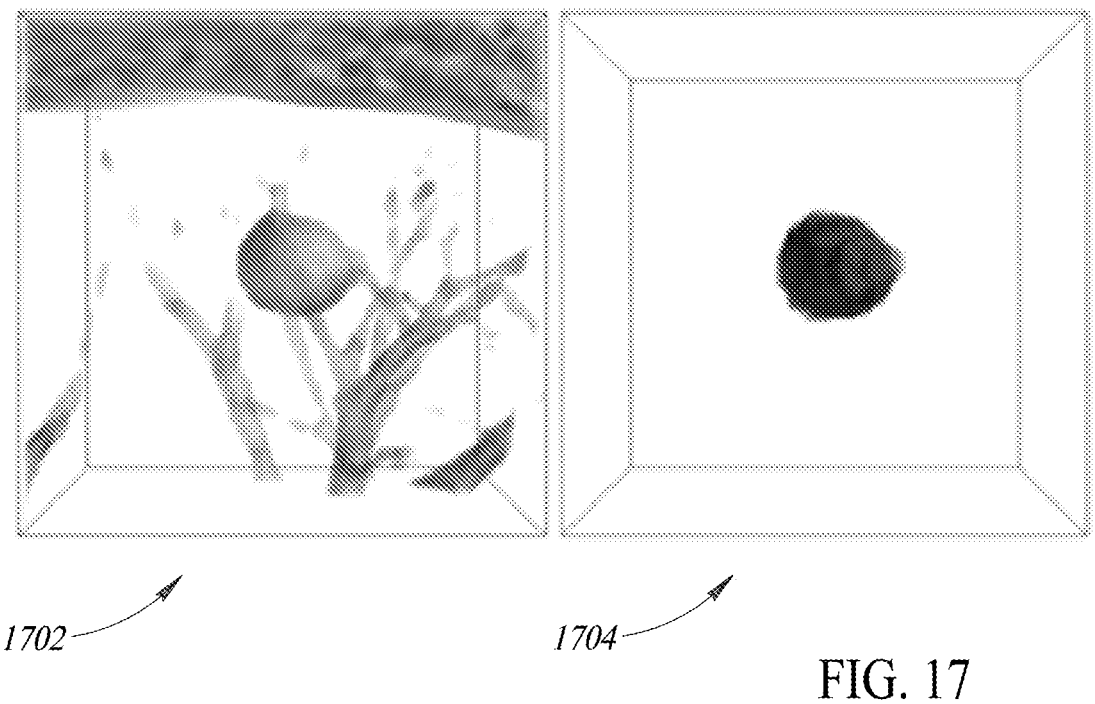
FIG. 17 is an image that displays a randomly selected case from the segmentation network training database.

The training database for the segmentation network is very similar to that of the proposal network, as both are segmentation networks. One main difference is that the segmentation network operates in 3D, while the proposal network operates in 2D, 3D, or a combination thereof. The network is trained only on 3D patches that contain lesions, though in some implementations non-lesions are also included. 3D patches are extracted from the raw CT scans or MRIs centered on the center of mass of each ground truth lesion. Patches are extracted such that the pixel spacing is fixed along all axes. In at least some implementations, the system utilizes patches that are 64 pixels along each edge, but a different size may be used in other implementations to achieve similar results. The 3D image patches are matched with 3D boolean masks representing whether each pixel within the 3D patch is in a lesion. The unique key utilized is the lesion location, though other unique keys may be used. FIG. 17 displays a 3D render of the 3D patch 1702 and 3D ground truth boolean mask target 1704 for an input/target pair randomly pulled from the training database.

Segmentation Network Training

In at least some implementations, the segmentation network is trained as described above with reference to FIG. 7 with no further adjustments.

Segmentation Network Inference

Figure 18:
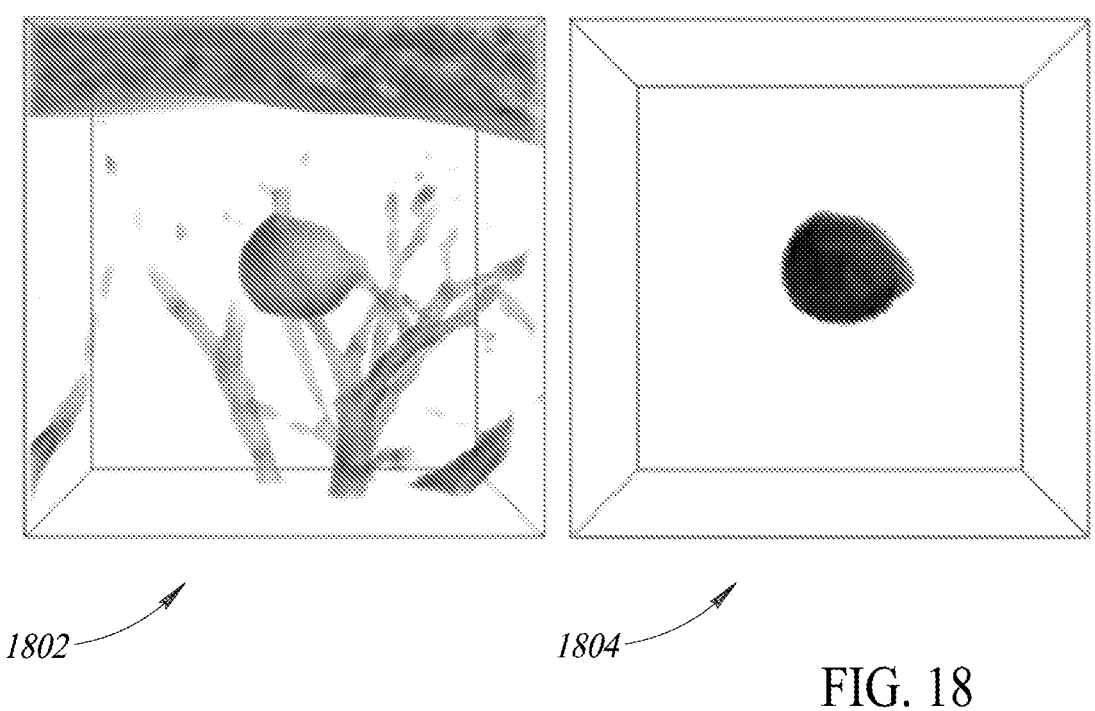
FIG. 18 is an image that displays inference results for a randomly selected case from the segmentation network training database.
Figure 19:
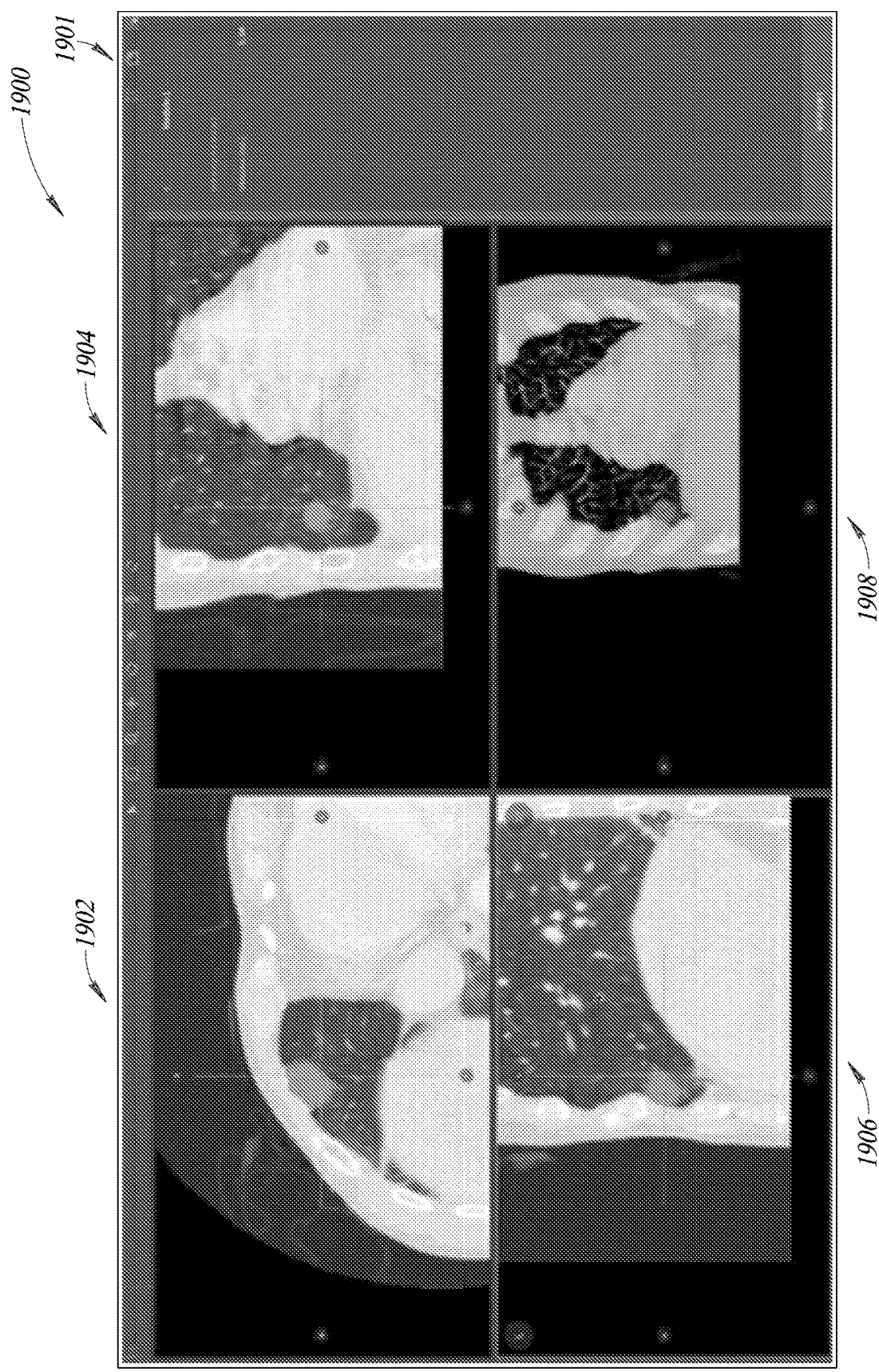
FIG. 19 is an image that displays inference results for a randomly selected case from the segmentation network training database in a web application.

FIG. 18 shows a render of the 3D input patch 1802, the corresponding segmentation and ground truth annotation 1804. FIG. 19 displays a view 1900 of an example lesion segmentation calculated with a segmentation network in the web application. The lesion segmentation mask from the segmentation network is presented in axial 1902 (top left), sagittal 1904 (top right), coronal 1906 (bottom left), and 3D reconstruction 1908 (bottom right) views in the web application. The volume 1901 of the mask is displayed to the user.

Co-Registration

Figure 20:
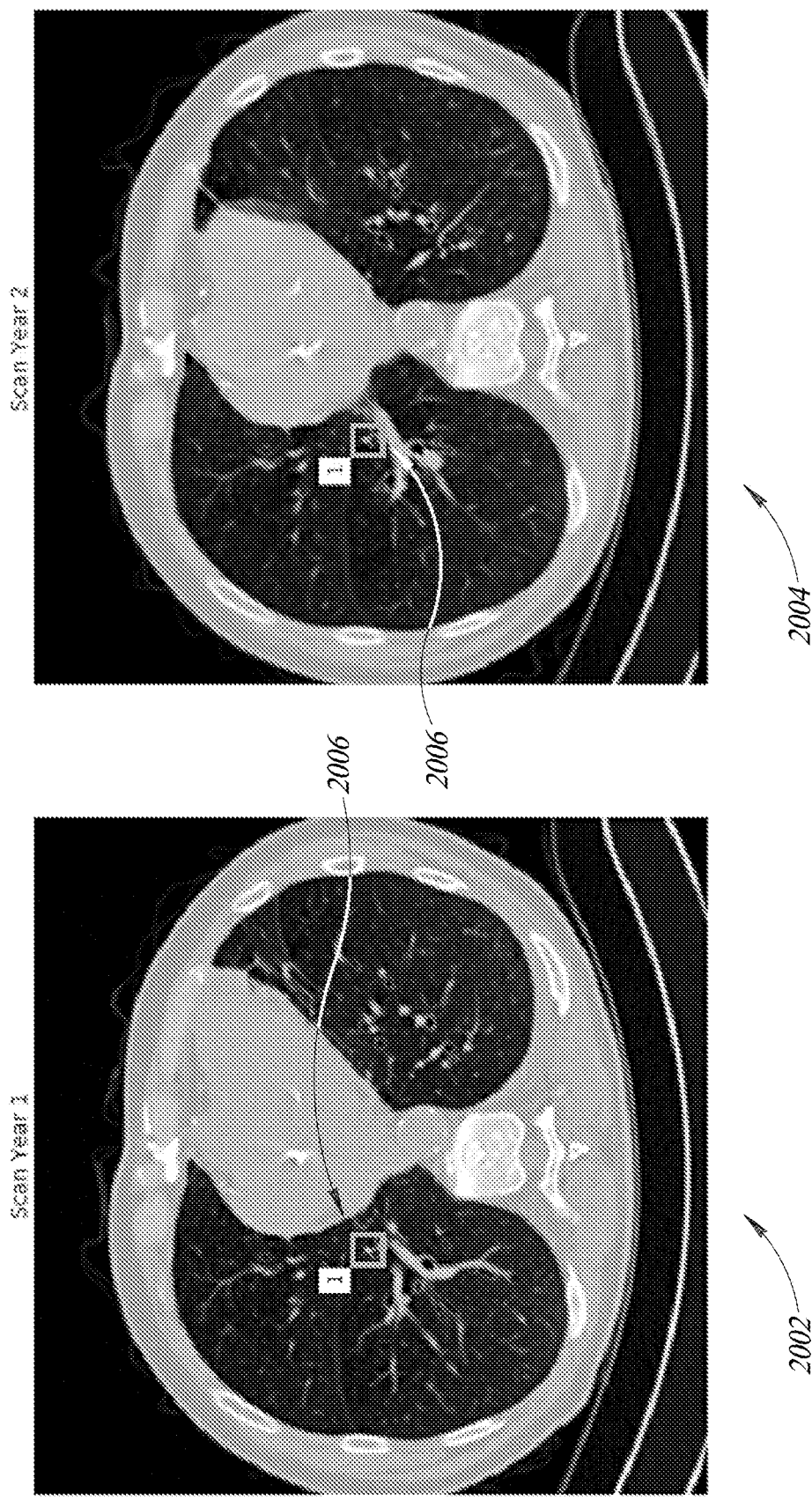
FIG. 20 is an image that displays co-registration results via a single axial slice for two scans from the same patient in sequential years.
Figure 21:
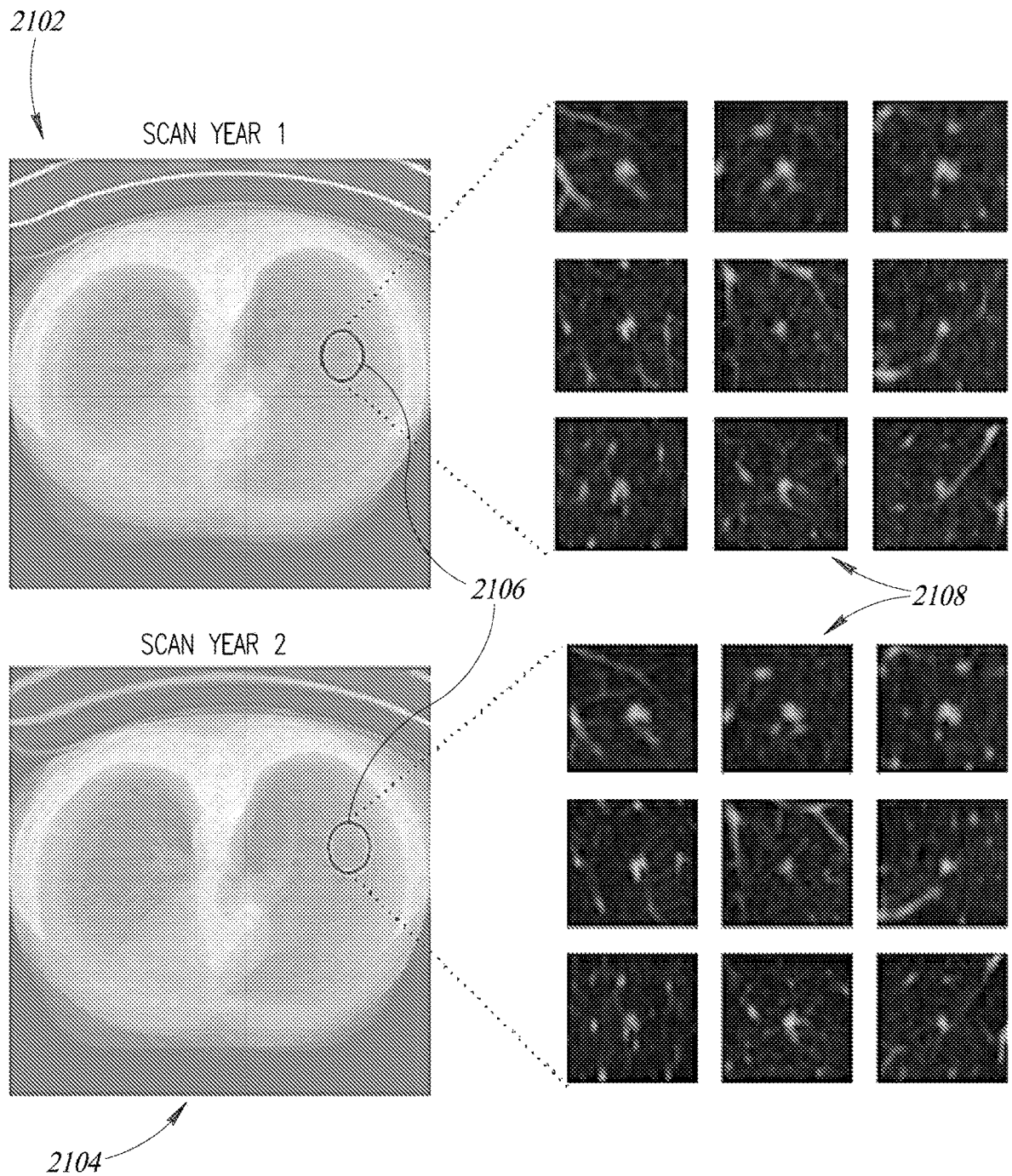
FIG. 21 is an image that displays co-registration results via an axial intensity projection and 9-planes views for two scans from the same patient in sequential years.

Co-registration of two scans is important for display purposes, machine learning training and inference, and clinical interpretation. Often, multiples series taken in the same session will be misaligned due to the patient shifting or inconsistent breath holds. Furthermore, in order to assess tumor growth, recession, and/or response to treatment, a patient will come in for a follow up scan, and the doctor would like to visually compare and quantify changes in possibly malignant observations. Though the applications of co-registration are slightly different, the technique for co-registration may be the same. FIGS. 20 and 21 display examples of a co-registration algorithm according to at least one implementation of the present disclosure. In FIG. 20, an axial slice of co-registered scans for the same patient for an initial scan 2002 and a follow up scan the next year 2004 is displayed. A lesion identified to be the same lesion in both scans is centered in box 2006. In FIG. 21, axial maximum intensity projections for co-registered scans for the same patient for an initial scan 2102 and a follow up scan the next year 2104 with a specific longitudinally identified lesion in the circle 2106 displayed as 2.5D nine plane views 2108 are displayed.

In general, the goal of image co-registration is to find a certain transformation so that when applied to the moving image, its similarity with the fixed image is maximized. Linear transformations and elastic transformations describe the two main classes of registration algorithms. The choice of transformation depends on the organ of interest in the scan. For example, rigid affine transformation may be applied to brain scans since the skull is rigid and the movement of the brain is limited in the skull, as discussed in Huhdanpaa, H., Hwang, D. H., Gasparian, G. G., Booker, M. T., Cen, Y., Lerner, A., . . . Shiroishi, M. S. (2014), image Co-registration: Quantitative Processing Framework for the Assessment of Brain Lesions. *Journal of Digital Imaging*, 27(3), 369-379. http://doi.org/1007/s10278-013-9655-y. However, elastic transformations may be important for precise registration of non-rigid organs, such as the liver or lungs.

For affine transformation, points, lines and planes are preserved in the transformation, e.g., rotation, translation and scaling are allowed. In the case of affine rigid transformation, only rotation, translation and reflection are allowed. Because affine transformation is formulated as a matrix multiplication, co-registration using affine transformation is generally much faster than elastic co-registration.

For elastic transformation, local deformation is applied to the moving image using, e.g., b-spline or thin-spline transformation.

A similarity metric is a continuous measure of degree of similarity between two images, and registration methods attempt to maximize the chosen similarity metric. Common choices of similarity measure include mutual information, cross-correlation and sum of squared differences. The similarity metric is used as a cost function for optimizing the transformation parameters in stochastic gradient descent.

Similarity metrics can be calculated on the intensity of the image directly or features extracted from the images. Image intensity and image features might be computed in an overlapping or non-overlapping sliding-window manner. Examples of image features are corresponding points, lines and curves.

For follow up scans in which it is desired that quantification of changes to any possibly malignant observations is determined, one of two potential algorithms is utilized, though others that pair lesion candidates could also be used. The first step for each algorithm is to co-register the scans. A greedy nearest neighbor algorithm pairs each lesion candidate in one scan with the closest lesion candidate in the other scan if it is not further than t mm away, which t is a distance threshold depends on organ and use cases. This process is repeated until there are no more lesion candidates left to be paired. Another option is to find sets of pairs such that the sum of distances among the paired lesion candidates is minimized. This pairing can be calculated using Hungarian algorithm, for example. For details of the Hungarian algorithm, see Kuhn, H. W. 1955. "The Hungarian Method for the Assignment Problem." *Naval Research Logistics* 2 (1-2). Wiley Subscription Services, Inc., A Wiley Company: 83-97. In addition, lesions are that t mm apart are ignored and will not be paired, where t is a distance threshold that depends on the organ and use cases.

Co-Registration Technique

Figure 22:
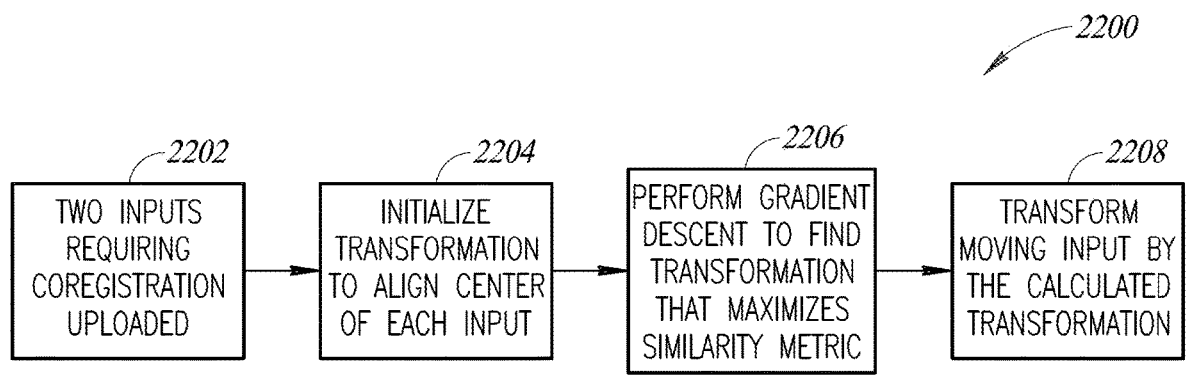
FIG. 22 is a flow diagram describing the co-registration system, according to one illustrated implementation.

In at least some implementations, the system utilizes a co-registration technique that does not use deep learning, though deep learning methods may also be used. The process is described in FIG. 22. The process 2200 begins at 2202 when two inputs that require co-registration are uploaded. The inputs could be, but are not limited to, two scans from different times for the same patient or two series from the same study for the same patient (here, a "scan" or "series" refers to any volume of data). Then, at 2204 the system initializes the transformation such that the center of the two inputs are aligned. Gradient descent is performed to find a rigid affine transformation or non-rigid transformation such that a certain similarity metric between the two scans is maximized at 2206. At this point, the transformation matrix can be utilized on the moving image at 2208, i.e., the one to be matched with the original. At this point, the co-registered inputs can be utilized. A specific configuration could be to use mutual information as the similarity metric with 50 histogram bins and SGD with a learning rate of 0.1 for 200 iterations, but in other implementations different configurations may be used to achieve similar results.

Display of Lesions

Figure 23:
FIG. 23 is an image that displays an axial top-down view of a 3D render of a lung scan with the opacity adjusted for certain structures.

It is important to display lung anatomy and lesions for doctor review in an easily accessible way. We allow the user to view the nodule annotations with the opacity of certain structures adjusted. FIG. 23 is an image 2300 that displays this effect from an axial top-down view, showing various lesions 2302.

Fully Convolutional Neural Networks for Region Proposals and Segmentation

This section describes in further detail the neural network architectures and variations discussed elsewhere in the description.

The general idea behind fully convolutional networks (FCNs) is to use a downsampling path to learn relevant features at a variety of spatial scales followed by an upsampling path to combine the features for pixelwise prediction. The downsampling path generally includes convolution and pooling layers, whereas the upsampling path includes upsampling and convolution layers. Downsampling the feature maps with a pooling operation is an important step for learning higher level abstract features by means of convolutions that have a larger field of view in the space of the original image. Upsampling the activation volumes back to the original resolution is necessary in a fully convolutional network for pixel-wise segmentation.

In at least some implementations, the system uses ReLUs (rectified linear units) for all activations following convolutions. Other nonlinearities, including PReLU (parametric ReLU) and ELU (exponential linear unit), may also be used.

UNet Variation Architecture

Figure 24:
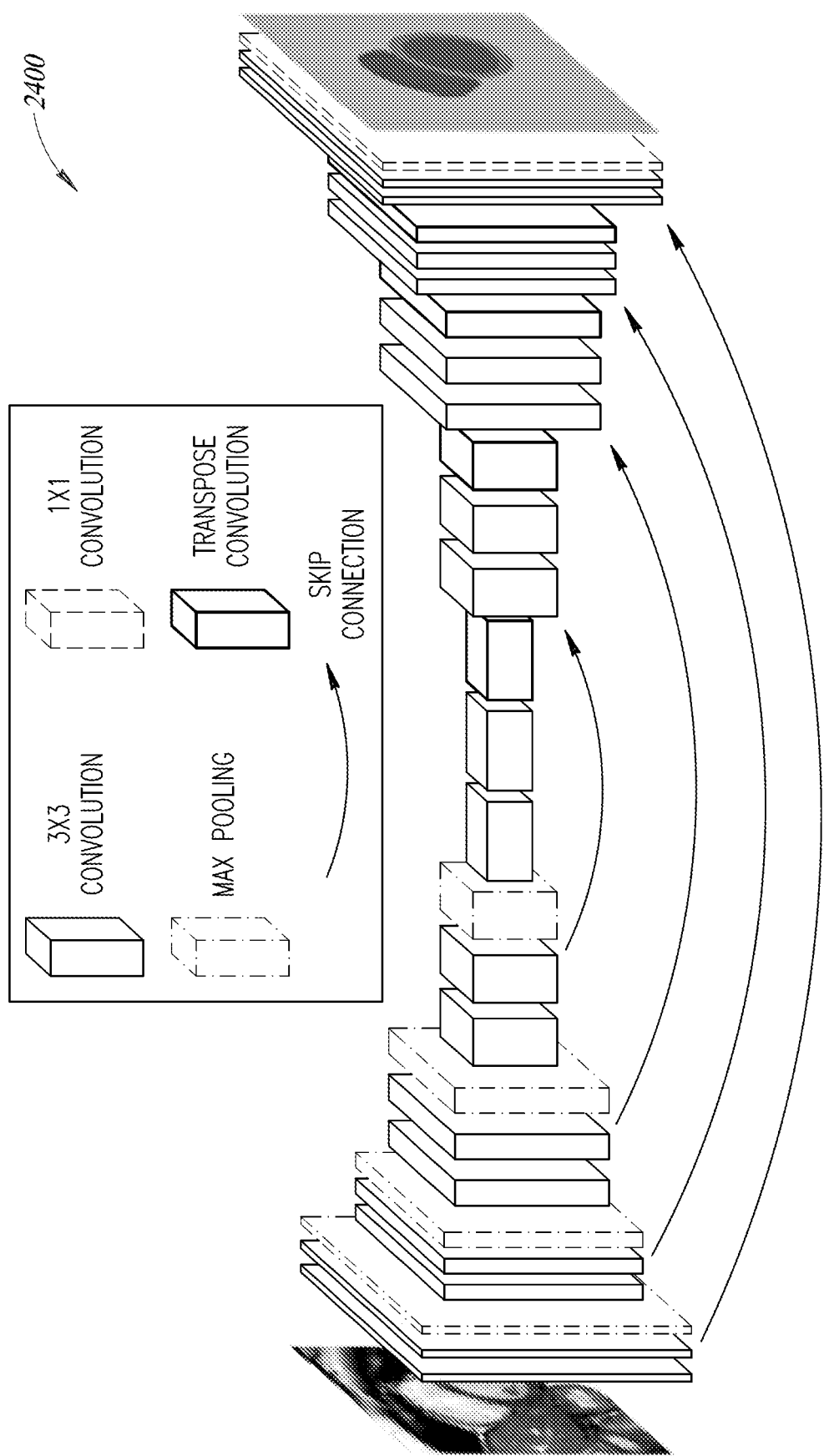
FIG. 24 is a schematic diagram of the U-Net network architecture used, according to one illustrated implementation.

FIG. 24 shows a schematic representation of the U-Net convolutional neural network architecture 2400 according to at least some implementations of the present disclosure. While superficially similar to the original U-Net, the modifications to the network overcome many of the limitations of the original U-Net. For details on the original U-Net, see Ronneberger, O., Fischer, P., Brox, T.: U-Net: Convolutional networks for biomedical image segmentation. In: Medical Image Computing and Computer-Assisted Intervention— MICCAI 2015, pp. 234-241. Springer (2015)

As in U-Net, the FCN 2400 according to an implementation of the present disclosure utilizes two convolutional layers before every pooling operation, with convolution kernels of size 3×3 and stride 1. Different combinations of these parameters (number of layers, convolution kernel size, convolution stride) may also be used, although the results may not improve. U-Net uses a total of four contracting pooling operations, followed by four upsampling operations; based on a hyperparameter search it was found that four pooling and upsampling operations worked best for the data, though the results are only moderately sensitive to this number.

Without applying any padding to input images (this lack of padding is called "valid" padding), convolutions that are larger than 1×1 naturally reduce the size of the output feature maps, as only (image_size−conv_size+1) convolutions can fit across a given image. The original U-Net uses valid padding, and as such, their output segmentation maps are only 388×388 pixels, even though their input images are 572×572 pixels. Segmenting the full image therefore requires a tiling approach, and segmentation of the borders of the original image is not possible. In the network, zero-padding of width (conv_size−2) is utilized before every convolution such that the segmentation maps are always the same resolution as the input (known as "same" padding). Valid padding was experimented with as well, but found it did not improve the results.

As in U-Net, a 2×2 max pooling operation with stride 2 is used to downsample the images after every set of convolutions. Learned downsampling, i.e., convolving the input volume with a 2×2 convolution with stride 2 was experimented with, but found it increased computational complexity without improving performance. Different combinations of pooling size and stride were also tried, but it was found the results did not improve.

To increase the resolution of the activation volumes in the network 2400, U-Net uses an upsampling operation, then a 2×2 convolution, then a concatenation of feature maps from the corresponding contracting layer through a skip connection, and finally two 3×3 convolutions. The upsampling and 2×2 convolution are replaced with a single transpose convolution operator, which performs upsampling and interpolation with a learned kernel, improving the ability of the model to resolve fine details. As in U-Net, that operation is followed with the skip connection concatenation. Following this concatenation, two 3×3 convolutional layers are applied.

The number of free parameters in the network 2400 determines the entropic capacity of the model, which is essentially the amount of information the model can remember. A significant fraction of these free parameters reside in the convolutional kernels of each layer in the network. The network is configured such that, after every pooling layer, the number of feature maps doubles and the spatial resolution is halved. After every upsampling layer, the number of feature maps is halved and the spatial resolution is doubled. With this scheme, the number of feature maps for each layer across the network can be fully described by the number in the first layer.

ENet Variation

Figure 25:
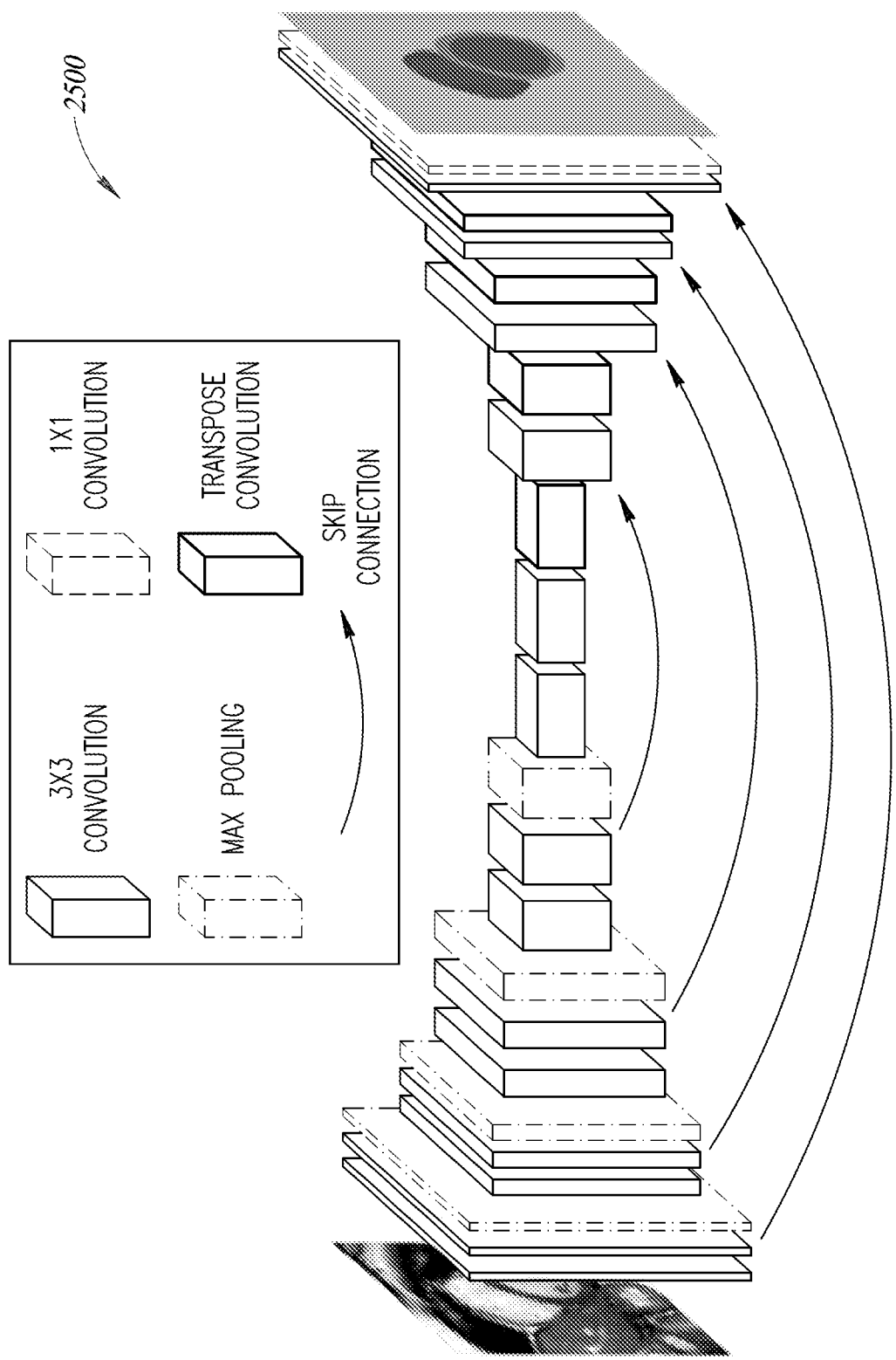
FIG. 25 is a schematic diagram of the ENet network architecture used, according to one illustrated implementation.

Disadvantages of fully symmetric architectures in which there is a one-to-one correspondence between downsampling and upsampling layers are that they can be slow and have a significant memory footprint, especially for large input images. ENet, an alternative FCN design, is an asymmetrical architecture optimized for speed. For details on the original ENet implementation, see Paszke, Adam, et al. "Enet: A deep neural network architecture for real-time semantic segmentation," arXiv preprint arXiv:1606.02147 (2016). FIG. 25 shows a schematic representation of the U-Net convolutional neural network architecture 2500 according to at least some implementations of the present disclosure.

ENet utilizes early downsampling to reduce the input size using only a few feature maps. This reduces both training and inference time, given that much of the network's computational load takes place when the image is at full resolution, and has minimal effect on accuracy since much of the visual information at this stage is redundant. ENet also makes use of bottleneck modules, which are convolutions with a small receptive field that are applied in order to project the feature maps into a lower dimensional space in which larger kernels can be applied. Throughout the network, ENet leverages a diversity of low cost convolution operations. In addition to the more-expensive n×n convolutions, ENet also uses cheaper asymmetric (1×n and n×1) convolutions and dilated convolutions. A significant limitation of the original ENet implementation is the lack of skip connections, limiting the network's ability to learn from and predict fine details. As such, the ENet variation utilizes skip connections.

3D FCNs

In at least some implementations, the system may extend the 2D implementations of UNet and ENet to utilize 3D convolutions, 3D pooling, and 3D upsampling.

ResNet Variation

For classification, convolutional neural networks using residual connections, i.e., residual networks, ResNet, may be used. For details on ResNet, see He, Maiming, et al. "Deep residual learning for image recognition." *Proceedings of the IEEE Conference on Computer Vision and Pattern Recognition.* 2016. A variant of the residual network for false positive reduction is used in this disclosure. Residual connection adds an identify mapping (or bypass) between the input and the output of the convolution and activation layer, improving gradient flow in very deep neural networks.

The variant of ResNet in this disclosure utilizes identity mappings wherein a residual block consists of 2 repetitions of Batch Normalization layer, ReLU activation layer and a convolutional layer. For details of this variant, see He, Kaiming, et al. "Identity mappings in deep residual networks." *European Conference on Computer Vision.* Springer International Publishing, 2016. A pooling block consists of one or more residual blocks in which the last convolutional layer has stride of 2 to reduce dimension of the feature maps. The variant of ResNet starts with a Convolution layer, ReLU activation layer and a Batch Normalization layer. Unlike the original ResNet, a Max Pooling layer was not used after because the lesion image patches size is smaller than the input size. A certain number of pooling blocks follows, and the network ends with a global averaging layer to reduce size of the feature map to 1×1. The final layer is a fully connected layer of 1 neuron with sigmoid nonlinearity.

Model Hyperparameters

The model hyperparameters are stored in a configuration file that is read during training. Each model (U-Net, ENet, ResNet) and dimensionality (2D, 3D) will have a specific set of hyperparameters. Parameters that describe a 2D U-Net model include:
    num_pooling_layers: the total number of pooling (and upsampling) layers
    pooling_type: the type of pooling operation to use
    num_init_filters: the number of filters (convolutional kernels) for the first layer
    num_conv_layers: the number of convolution layers between each pooling operation
    conv_kernel_size: the edge length, in pixels, of the convolutional kernel
    dropout_prob: the probability that a particular node's activation is set to zero on a given forward/backward pass of a batch through the network
    border_mode: the method of zero-padding the input feature map before convolution
    activation: the nonlinear activation function to use after each convolution
    weight_init: the means for initializing the weights in the network
    batch_norm: whether or not to utilize batch normalization after each nonlinearity in the down-sampling/contracting part of the network
    batch_norm_momentum: momentum in the batch normalization computation of means and standard deviations on a per-feature basis
    down_trainable: whether to allow the downsampling part of the network to learn upon seeing new data
    bridge_trainable: whether to allow the bridge convolutions to learn
    up_trainable: whether to allow the upsampling part of the network to learn
    out_trainable: whether to allow the final convolution that produces pixel-wise probabilities to learn Parameters that describe the training data to use include:
    crop_frac: the fractional size of the images in the LMDB relative to the originals
    height: the height of the images, in pixels
    width: the width of the images, in pixels Parameters that describe the data augmentation during training include:
    horizontal_flip: whether to randomly flip the input/label pair in the horizontal direction
    vertical_flip: whether to randomly flip the input/label pair in the vertical direction
    shear_amount: the positive/negative limiting value by which to shear the image/label pair
    shift_amount: the max fractional value by which to shift the image/label pair
    zoom_amount: the max fractional value by which to zoom in on the image/label pair
    rotation_amount: the positive/negative limiting value by which to rotate the image/label pair
    zoom_warping: whether to utilize zooming and warping together
    brightness: the positive/negative limiting value by which to change the image brightness
    contrast: the positive/negative limiting value by which to change the image contrast
    alpha, beta: the first and second parameters describing the strength of elastic deformation. For more details on elastic deformation, see Simard, Steinkraus and Platt, "Best Practices for Convolutional Neural Networks applied to Visual Document Analysis", in Proc. of the International Conference on Document Analysis and Recognition, 2003.

Parameters that describe training include:
    batch_size: the number of examples to show the network on each forward/backward pass
    max_epoch: the maximum number of iterations through the data
    optimizer_name: the name of the optimizer function to use
    optimizer_lr: the value of the learning rate objective: the objective function to use
early_stopping_monitor: the parameter to monitor to determine when model training should stop training
early_stopping_patience: the number of epochs to wait after the early_stopping_monitor value has not improved before stopping model training To choose the optimal model, a random search over these hyperparameters is performed and the model with the highest validation accuracy is chosen.

B. CONTENT BASED IMAGE RETRIEVAL FOR LESION ANALYSIS

Terms

API—Application Programming Interface
Benign—Not cancerous
CBIR—Content-Based Image Retrieval
CBIR Database—Database containing images and (in some implementations) one or more of image features and clinical features for lesions that may be returned to the user
CBIR Image Database—Database containing the images from which features may be extracted for lesions that may be returned to the user
Clinical Features—Features related to a lesion that are derived from clinical data of the patient from whom the lesion is drawn, such as: demographic information, medical history, biopsy results or semantic features determined through radiological examination
CNN—Convolutional Neural Network
CT—Computed Tomography
Database—Any nontransitory processor-readable storage medium, including but not limited to a relational database (e.g., MySQL), a "NoSQL" database (e.g., MongoDB), a key-value store (e.g., LMDB), or any centralized or distributed file system
EHR—Electronic Health Record
Ground Truth Label—The label that is correctly associated with an image for the purpose of training or evaluating a machine learning model; to be contrasted with the predicted label
Image Features—Features that are derived from the pixel data of one or more images
Lesion Features—Features related to a lesion that may be a combination of any or all of image features, clinical features or other features
Malignant—Cancerous
MR—Magnetic Resonance
Predicted Label—The label predicted by a machine learning model; may or may not be correct with respect to the ground truth label Current Clinical Practice for Radiological Estimation of Lesion Malignancy One of the most important tasks that radiologists need to perform is the review of medical images, such as magnetic resonance (MR) or computed tomography (CT), of patients who may have cancer. These patients may have imaging performed for a variety of reasons: they may be participating in cancer screening; they may have an unidentified mass from a clinical examination; they may have known cancer and are being imaged to track progression. As part of the review, the radiologist may discover potentially malignant lesions. The radiologist must then make an assessment of the likelihood of malignancy of the lesions. Such an assessment will then lead to decisions for follow-up care for the patient, which may include any of: no treatment, follow-up imaging, biopsy, cancer treatment (such as radiation, surgery or chemotherapy) or others.

Although radiologists receive training in the practice of determining the likelihood of malignancy from radiological images, the great variety of presentations for both benign and malignant lesions makes this task extremely challenging. For example, Lung-RADS assessment categories [ACR Lung-RADS] are often used for the clinical prediction of malignancy for lung nodules and LI-RADS assessment categories [ACR LI-RADS] perform the same role for assessing potential hepatocellular carcinoma in liver lesions. These systems are generally structured as decision trees, in which a clinician will assess various morphological features associated with a lesion or its growth and then assign a category to the lesion based on the appropriate reporting system. There are at least two major challenges when using these reporting systems. The first challenge is that the assessment categories are very coarse (i.e., each category has a wide range of malignancy probabilities) which leads to low positive predictive value (PPV) in the classification of cancer and therefore unnecessary biopsy and treatment. The second challenge is that assessment of lesion morphological features is subjective and suffers from inter- and intra-rater variability.

The challenge that arises from the coarseness of the assessment categories can be illustrated with an example from Lung-RADS. Lung-RADS Version 1.0 dictates that the nodule category corresponding to the highest likelihood of malignancy, Category 4B, carries a true probability of malignancy of 15% or greater. Studies have shown that the true probability of malignancy for some Category 4B nodules is around 25%, a number that is similar to the Lung-RADS guideline of >15% [Chung 2017]. Because Category 4B constitutes the highest suspicion level, all Category 4B nodules are likely to be recommended for biopsy. If the true likelihood of malignancy of Category 4B nodules is 25%, indicating a positive predictive value (PPV) of 25%, this means that 75% of all Category 4B nodules that are recommended for biopsy are benign and that the biopsies in those cases were not truly necessary. There is therefore a critical need to provide radiologists better tools to improve the PPV of malignancy prediction which would allow them to reduce the number of invasive biopsy procedures for patients who do not stand to benefit from them. Simultaneously, improvements to sensitivity would allow radiologists to detect more malignant lesions earlier, leading to more timely care for patients.

The second challenge of malignancy assessment based on clinical reporting systems is related to the inter- and intra-reader variation, an issue that is well-established for the clinical diagnosis of medical images [van Riel 2015] [Gulshan 2016]. Inter-reader variation results from a variety of factors, including differences in clinical training, years of experience, and frequency of reading a particular type of image. Intra-reader variation can be influenced by how much time a clinician has to read a scan or the context in which the scan is read (e.g., whether the clinician's other most recently-read scans contained benign or malignant lesions). Providing the appropriate, objective information to clinicians during the process of diagnostic decision making can reduce this inter- and intra-reader variation by reducing biases and giving more historical context to the current case.

Content-Based Image Retrieval (CBIR)

Content-based image retrieval (CBIR) constitutes a class of machine learning methods to retrieve images (and possibly other associated information) from a database based on the similarity of those images to a query image. The query image is drawn from the medical images of the query patient, which is usually the patient for whom the clinician seeks to make a clinical assessment. By using a CBIR system to retrieve similar images along with information about the clinical outcomes of the patients from whom those images are drawn, the clinician gains direct access to imaging and outcomes information for similar patients. The clinician can then incorporate that information into the process of making a diagnosis for the query patient.

Although an effectively implemented CBIR system has the potential to significantly improve the accuracy of cancer diagnosis, implementation of a CBIR system can be very challenging. An effective CBIR system should have the following properties:

A large, diverse database of images
A clinically relevant definition of similarity
A scalable way of querying the database In the past, many of the aspects that define a successful CBIR system have been very difficult to achieve. Some of the obstacles are described in detail below.

A large, diverse database of images

Assembly of a large, diverse database of images has traditionally been very challenging. Standard clinical care for the radiological assessment of suspicious lesions typically involves the review of images followed by the dictation of relevant findings into a textual report. Although reviewers may make basic measurements on the image, such as the longest linear dimension of the lesion, these measurements are typically not stored in a manner that allows them to be easily retrieved for research or product development. It is therefore impossible to use these reports to localize lesions on images for later retrieval.

It is therefore necessary to execute a targeted annotation procedure to localize lesions on their original images. Because the annotation of images typically requires a trained radiologist or technologist, this procedure is often prohibitively time consuming, expensive, or both. Two very recent innovations have changed that calculation. The first is the recent advent of large, well-annotated data sets, such as the LIDC-IDRI dataset [Armato 2011], which includes multi-reader volumetric localization and segmentations of lung nodules. The second is the development of the cloud-based radiological viewing software, such as the web-based application provided by Arterys, Inc., which collects in a central cloud database all annotations created by users, including linear distance and volumetric annotations. These annotations, provided by radiologists and technologists as part of standard clinical care, can then be easily used to localize lesions in images, allowing the lesions themselves, along with localized pixel data and related metadata, to be stored in a database for subsequent analysis and retrieval.

A Clinically Relevant Definition of Similarity

The concept of lesion similarity is subjective and context dependent; not only may two different individuals disagree on the definition of similarity, but the same user may also wish to change the definition to suit different purposes. For example, one definition of similarity may be relevant for distinguishing between benign and malignant lesions, while another definition may be relevant for distinguishing between different cancerous subtypes.

Even when a clinician is able to express their definition of similarity, it has in the past been challenging to computationally quantify that definition. For example, the presence of spiculations in lung nodules tends to increase the likelihood that the nodule is malignant, so a clinician may prefer that spiculations factor into the definition of similarity. However, computationally quantifying the extent to which a lung nodule is spiculated has traditionally required the extraction of hand-crafted features. These hand-crafted features would be meticulously designed based on low-level image processing techniques, such as wavelets, texture analysis, the Hough transform and others. Hand-crafted features traditionally took a very long time to develop and were very fragile and dependent on intricacies with the given data set. However, the very recent advent of deep learning, and particularly convolutional neural networks [Russakovsky 2015], has significantly reduced the difficulty of extracting relevant features. Using modern deep learning-based convolutional neural networks (CNNs), one can straightforwardly extract any features for which well-curated training data is established.

The burden has therefore shifted away from the design of hand-crafted features and towards the curation of labeled datasets and the design of effective models for feature extraction. Once a clinically relevant set of features—including, for example, spiculations—is identified, one can create a training dataset with lesions and their ground truth annotations (including, e.g., the degree of spiculation for each lesion), design a CNN model to predict the annotations, and train it on the training dataset. That model can then be used to extract the features from new images beyond those in the training dataset and the features may be included as part of the definition of similarity for comparing a query lesion to lesions from a database.

CNNs can alternatively be used to extract relevant features less directly. Because a CNN includes many layers, one can extract features from any layer of the CNN and use those features as part of the definition of similarity. For example, a CNN can be trained as a binary classifier to classify images of lesions as benign or malignant. The final output of such a network typically has only a single scalar value: the probability that a lesion is malignant, from 0 to 1. However, the layers prior to the final layer of a CNN model typically have on the order of 1000 or more features [He 2016]. These are mid-level features that the CNN model has learned are relevant for the ultimate prediction of malignancy. Because these mid-level features must ultimately depend on the morphological appearance of the lesion (given that the lesion image is the input to the model), they may also be relevant for retrieving similar lesions. These lower-level features could therefore be used directly, or with some postprocessing, to calculate lesion similarity.

Finally, a CNN model could be used to directly predict the similarity of a query lesion to other lesions in the database. For example, if a training data set was created that consisted of a set of query lesions and their quantitative similarity to some or all lesions within a database of lesions, a model could be trained on that data set. That model would then be able to predict similarity for a new query lesion to lesions from the database.

A Scalable Way of Querying the Database

CBIR is most effective when integrated with a clinician's existing workflow. This presents a challenge for traditional radiological postprocessing tools, which are workstation-based and typically possess minimal ability to send data to or receive data from outside of a hospital's IT network. Part of this restriction is technological (e.g., building network-connected software is difficult) and part is administrative (e.g., hospitals prefer to restrict network connectivity to reduce the possibility of a data breach). A large database of retrievable images and associated information, particularly a dynamic one, cannot easily be maintained within the context of a single workstation, because of both its size and its need for continual updates.

A cloud-based solution, in which the CBIR interface is a web-based application, can fully support the needed scalability and dynamism of the CBIR database. For such a solution to be effective, it must both integrate with the clinician's workflows and mitigate the privacy risk of sending data between the hospital and the outside network.

DETAILED DESCRIPTION

1st Embodiment

System Overview

One implementation of the full content-based image retrieval system is described below in two separate phases: the "training" phase, in which the models and databases that will be used in operation of the system are developed, and the "inference" phase, in which a user interacts with the system to retrieve images that are similar to a query image.

Figure 26:
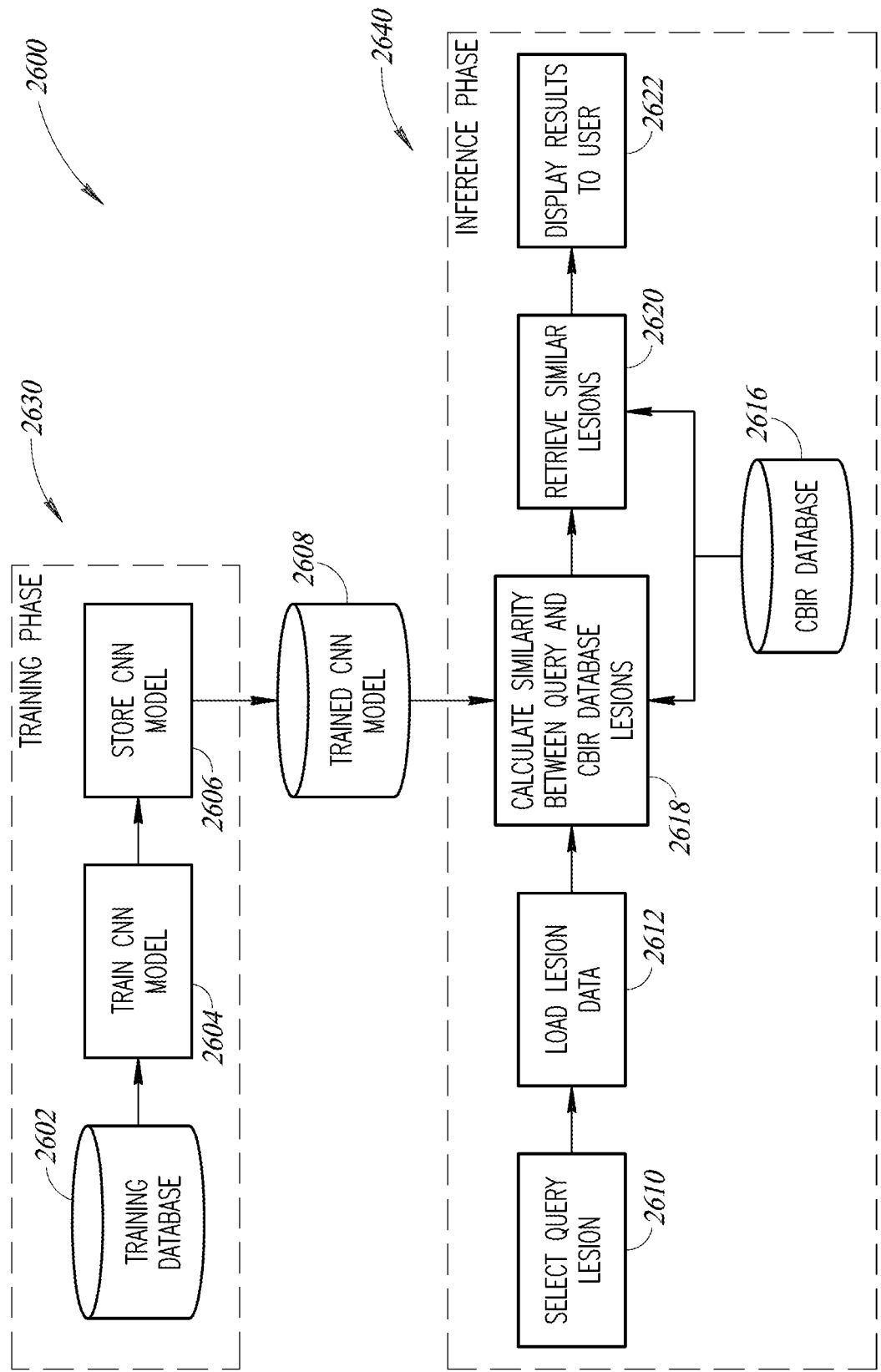
FIG. 26 is a schematic diagram of one implementation of a system that may be used for content based image retrieval, according to one non-limiting illustrated implementation.

FIG. 26 shows one implementation of a complete system 2600, including both a training 2630 and an inference 2640 phase. In the training phase 2630 of this implementation, training images, optionally along with "labels" or "targets" for the images, are stored in a training database 2602. For implementations in which the CNN model that is trained is a supervised learning model, the training database 2602 contains labels, whereas for implementations in which the CNN model is an unsupervised learning model, labels may not be used in the training process and therefore do not need to be stored in the training database 2602. The training images, along with their labels if applicable, are used to train the CNN model 2604. Once trained, the CNN model 2604 is stored 2606 to disk or a database 2608. Note that the training process is described in more detail for different implementations below.

In the inference phase 2640 of this implementation, a query lesion is initially selected at 2610. Data related to the lesion is then loaded at 2612. Once the image data of the query lesion is loaded, the trained CNN model 2608 is used along with the lesion data 2612 to calculate the similarity between the query lesion and lesions in the CBIR database lesions at 2618. Different implementations for how similarity is calculated 2618 are described elsewhere herein.

Once similarity has been calculated between the query lesion and lesions from the CBIR database, similar lesions are retrieved from the CBIR database 2616 at 2620. After similar lesions are retrieved, they are displayed to the user of the software at 2622. Additional details and different possible implementations of the user interface are discussed further below.

Training

Figure 27:
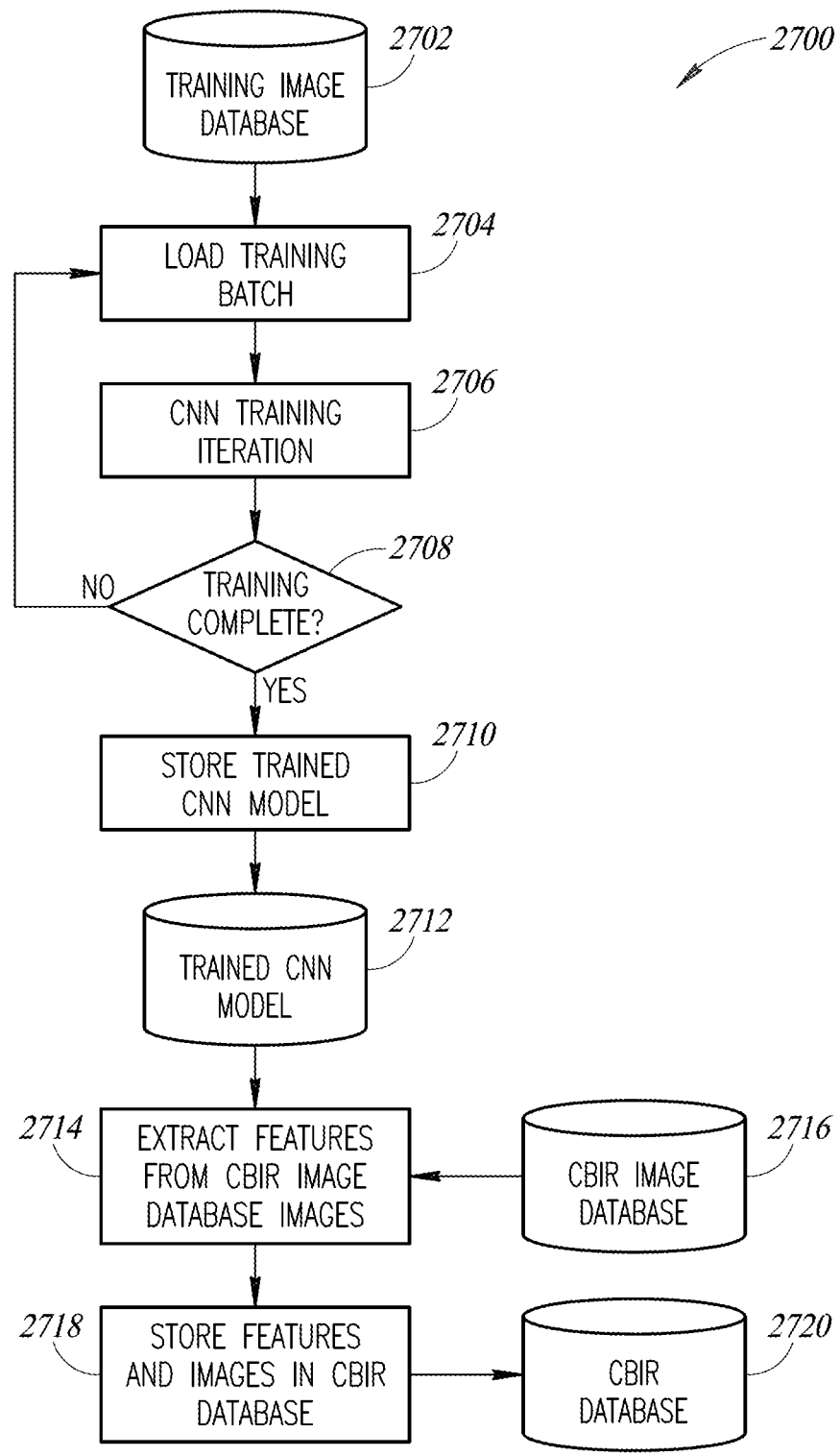
FIG. 27 is a schematic block diagram of a convolutional neural network training procedure according to an implementation wherein the convolutional neural network operates as a feature extractor.

Several different implementations of the training phase 130 are described below. FIG. 27 shows a method 2700 of one implementation of training, in which a CNN is trained for use as a feature extractor. Training data is stored in the training image database 2702. In at least some implementations, training is performed in a supervised manner and data in the training image database 2702 includes both lesion images and ground truth labels. Those labels may take on many forms, depending on the specific CNN implementation, including but not limited to: Lesion diagnosis (e.g., malignancy, type of malignant lesion, overall type of lesion including benign and malignant lesions); lesion characteristics (e.g., size, shape, margin, opacity, heterogeneity); characteristics of the tissue surrounding the lesion; location of the lesion within the body; whether the image is drawn from a real radiological image or one fabricated by, e.g., the generator of a generative adversarial network; or any combination of the above.

Training is cyclical process and includes repeated loading of batches of training data from the database at 2704, followed by a standard CNN training iteration 2706. The standard CNN training iteration 2706 includes a forward pass of image data through the network, calculation of a loss function, and updating the weights of the CNN model using backpropagation [LeCun 1998]. For implementations in which the model is supervised, loss is calculated with respect to the network's output and the ground truth label. For implementations in which the model is unsupervised, loss is calculated with respect to some other metric, such as the inter-cluster distance of predicted results.

After each CNN training iteration 2706, some criteria is used to evaluate whether the training is complete at 2708. This criteria could take on any of several forms, including but not limited to: whether the evaluation loss is continuing to decrease with respect to historical loss data; whether a predetermined maximum number of training iterations have completed; whether a predetermined maximum amount of time has elapsed; or some combination of the above.

If training is not complete, another batch is loaded at 2704 and training continues; if training is complete, the cycle is broken and the CNN model is stored at 2710 and 2712.

The CBIR image database 2716 contains image data for lesions that may be returned as part of CBIR inference. These images are in the format from which features may be extracted using the trained CNN model 2712. Note that this image format may be different from the format of images that are returned to the user as part of CBIR inference. For example images from the CBIR image database 2716 may include the complete scan of the patient, which could be a multi-slice, multi-timepoint MR or CT study, for example. In contrast, images returned to the user as part of CBIR inference may be optimized for user viewing. In at least some implementations, returned images include simple thumbnails showing the lesions. In other implementations, images returned to the user include more complex data, such as the full scan with which the user can interact through an appropriate user interface.

After the trained CNN model is stored, images are drawn from the CBIR image database 2716 and features are extracted at 2714 using the trained CNN model 2712. These features are then stored 2718 in the CBIR database 2720. In at least one implementation, clinical features are also stored 2718 in the CBIR database 2720. Lesion images of the appropriate format for returning to the user are also stored 2718 in the CBIR database 2720.

Note that, in place of the single CNN described above, an ensemble of multiple CNNs, possibly with different training techniques or target label formats, may be used to extract complementary features.

Figure 28:
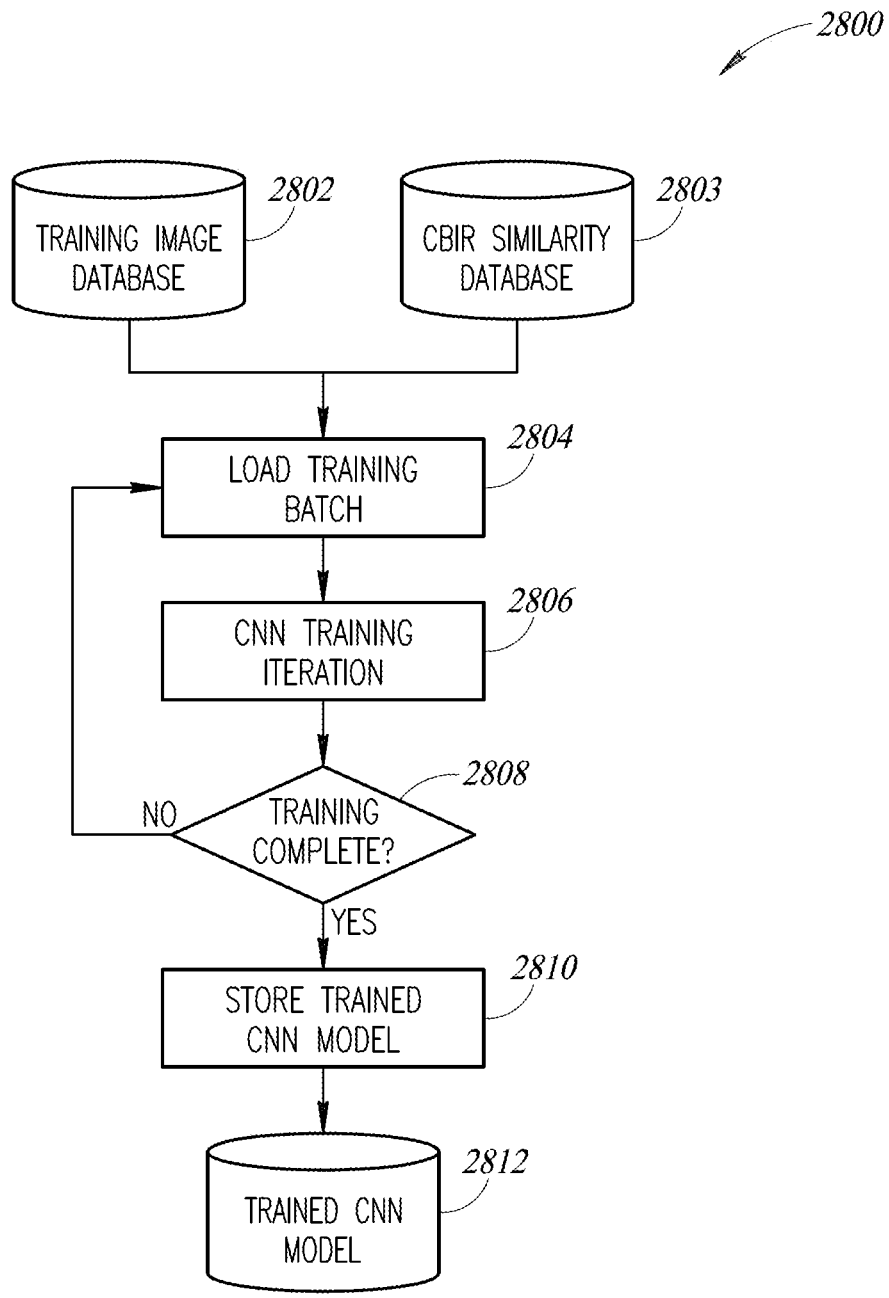
FIG. 28 is a schematic block diagram of a training procedure for a convolutional neural network according to an implementation wherein the convolutional neural network operates to provide predictions of similarity.

FIG. 28 shows a method 2800 of one implementation of training, in which a CNN is trained to directly predict similarity. As in the method 2700, training images are drawn from a training database 2802. One distinction between the implementation of the method 2800 and the implementation of the method 2700 is that, in the implementation of the method 2800, the ground truth labels drawn from the CBIR similarity database 2803 are themselves similarity scores between the training images and the images in the CBIR database. Unlike the implementation of the method 2700, where the CNN is used as a feature extractor, the CNN of the method 2800 is responsible for directly predicting the similarity between a given lesion image to some or all lesion images within the CBIR database.

Because similarity is an intrinsically subjective concept, there are several methods by which the similarity score targets of the CNN can be determined, including but not limited to: a system in which similarity is derived from similarities of the diagnosis or treatment response of the training database lesions and CBIR database lesions; a system in which clinicians or other trained individuals explicitly indicate the extent to which lesions in the CBIR database are similar to lesions in the training image database; or some combination of the above.

Similarity need only be determined between any given lesion in the training image database and a subset (as opposed to all) lesions in the CBIR database. Lesions in the CBIR database for which similarity is not determined may either have their similarity score imputed based on surrounding data or they may be ignored for a given training image while training the CNN model.

Beyond the difference in how labels are defined, the remaining steps of the training process for the implementation of method 2800 are analogous to the steps in the method 2700. As part of this implementation's training cycle, a batch of training data is loaded at 2804, a training iteration is performed at 2806, and completeness of training is evaluated at 2808. Unlike the training iteration of the act 2706, which could be either a supervised or unsupervised training iteration, the training iteration at 2806 may be exclusively supervised, with the similarity score as the ground truth label. Once training is complete at 2808, the CNN model is stored at 2810 and 2812. Unlike in the method 2700, features are not extracted for lesions in the CBIR image database 2716 and stored in the CBIR database 2720 in this implementation, because the CNN model of the method 2800 is not used as a feature extractor.

In at least some implementations, clinical features related to lesions in the training image database 2802 may be loaded along with the images when loading the training batch at 2804. In those implementations, the CNN input includes both image data and clinical features. Although the image data is used as input to the CNN at the first layer (the layer furthest from the output), the clinical features may be used as input to the CNN at any layer; for example, they may be used as input to the last layer (the layer closest to the output) of the CNN.

Inference

Figure 29:
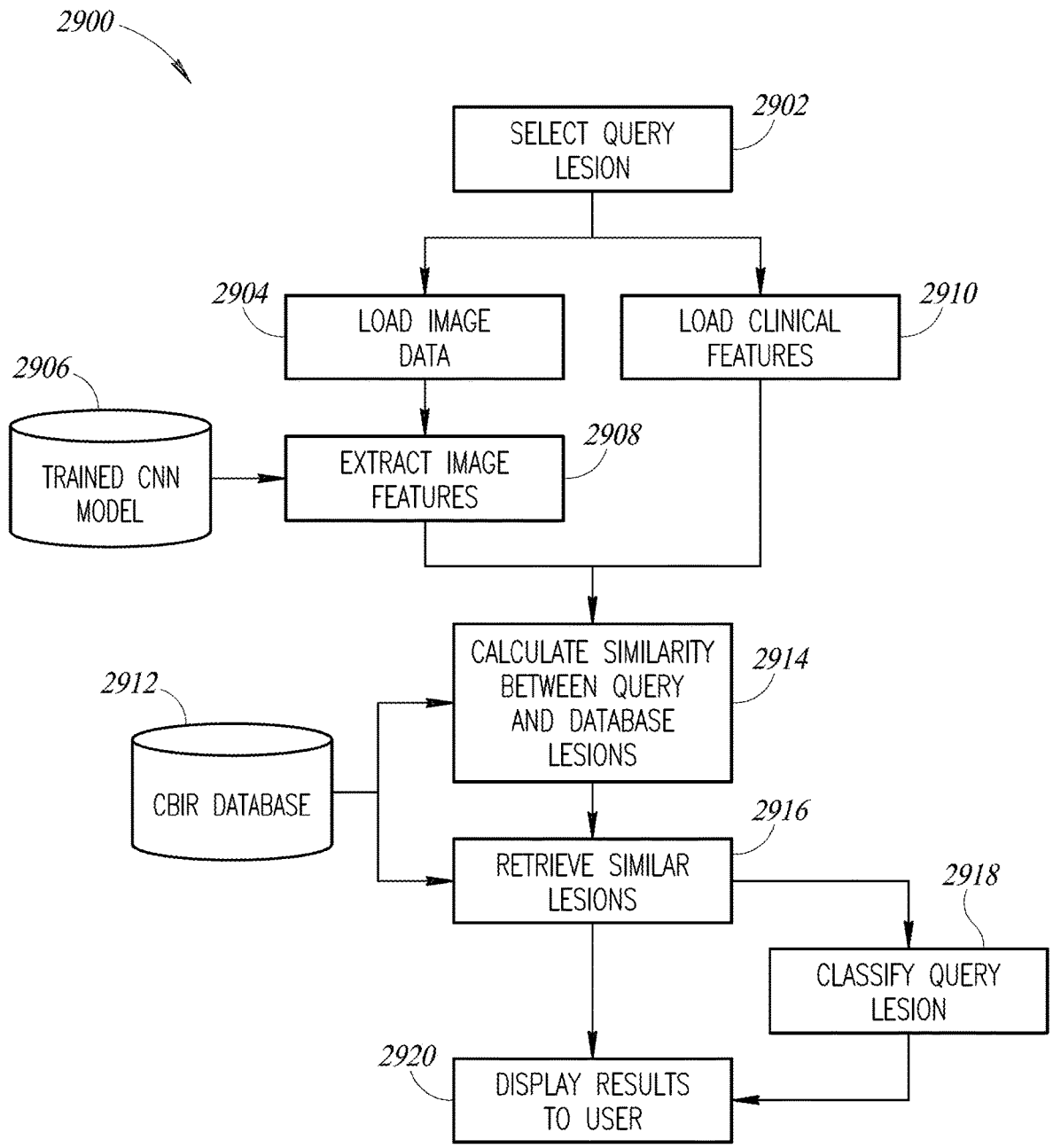
FIG. 29 is a schematic block diagram of a content based image retrieval process, wherein a convolutional neural network operates as a feature extractor.

Several different implementations of the inference phase 2640 (FIG. 26) are described below. FIG. 29 shows a method 2900 of a CBIR retrieval process in which a CNN is used as a feature extractor. Initially, the query lesion is selected at 2902. The query lesion could be selected in many different ways, including but not limited to: a user clicking on or tapping a lesion when viewing a radiological study (such as an MR or CT study); a user selecting a lesion from a list of previously identified lesions; via an automated system; or some combination of the above.

The lesion may be a lesion that a user (e.g., a radiologist) is interested in diagnosing as being malignant or benign. The lesion may be a lesion for which the radiologist wishes to diagnose the type or subtype of lesion (e.g., infection, fibroma, cancer, etc.), or it may be any other lesion for which the user wishes to retrieve similar lesions, including possibly a lesion for which the diagnosis is already known.

Image data associated with the lesion is then loaded at 2904. The image data includes pixels from the original radiological study (or some derivative thereof, such as one or more PNG or JPEG images) and may be 2D, 3D or of a higher dimension (e.g., in perfusion or cine studies that include a temporal dimension in addition to the three spatial dimensions).

In at least one implementation, clinical features are also loaded at 2910. These clinical features can be derived from the patient's electronic health record through an application programming interface (API) or they may be retrieved from a separate database that may either be colocated with or separated from the image data associated with the query lesion. These clinical features are used in conjunction with image features in order to retrieve similar lesions.

Once the image data of the query lesion is loaded, the trained CNN model 2906 is used to extract image features from the image data at 2908. The image features and clinical features are then used to calculate the similarity 2914 between the query lesion and lesions from the CBIR database 2912.

In at least one implementation, the CBIR database 2912 contains both lesion information to be retrieved as well as lesion features that are used as part of the similarity calculation. The lesion information to be retrieved includes some form of image data for display to the user as well as, in some implementations, lesion metadata, such as clinical information. In at least one implementation, the CBIR database 2912 is implemented as multiple linked databases that each contain different types of data; for example, one database may contain pixel data, another database may contain image features and yet another database may contain clinical features.

The similarity calculation of 2914 may be implemented in many different ways. In at least one implementation, the query lesion is compared to the lesions in the CBIR database 2912 by calculating the Euclidian distance between the features of the query lesion to the features of the lesions in the CBIR database. Other distance metrics, such as Manhattan, Minkowski or LP distance can also be used. Features may have individual weights such that, for example, image features are weighted more heavily in the distance calculation than clinical features. If features have individual weights, these may be set explicitly or implicitly by users, they may be based on aggregated preferences of users, or they may be based on users' feedback about the quality of the similar results. Features may also be combined in a non-linear fashion, e.g., using dimensionality reduction methods such as principal component analysis (PCA) or t-Distributed Stochastic Neighbor Embedding (t-SNE). Features may be combined based on their relationship, by, for example, reducing the dimensionality of clinical features independently from reducing the dimensionality of image features. For speed, similarity may be calculated using an approximate nearest neighbors algorithm [Muja 2009] instead of an exact algorithm.

In at least one implementation, similarity is directly calculated using a regression model. Such a regression model predicts a similarity metric between the query lesion and each lesion or a subset of lesions in the CBIR database 2912. The regression model takes as input image features and, in at least one implementation, clinical features. The output of the regression model is a similarity score between the query lesion and some or all lesions in the CBIR database. The regression model must have previously been trained on a set of lesions with known ground truth similarity to some or all lesions from the CBIR database. The regression model could be any type of feature-based regression, such as K-nearest-neighbors, logistic regression, multilayer perceptron, random forests or gradient boosted decision trees.

Similarity may be calculated on only a subset of lesions in the CBIR database 2912. In at least one implementation, similarity is only calculated based on patients with similar demographics or with similar clinical history to the patient from whom the query lesion is drawn. The criteria that determines which subset of similar lesions to return may be user selectable, or it may be determined automatically by the software.

Once similarity has been calculated between the query lesion and lesions from the CBIR database 2912, similar lesions are retrieved at 2916 from the CBIR database. All lesions from the CBIR database 2912 may be returned and ranked, or a subset of lesions may be returned. For the at least one implementation in which a subset of lesions are returned, there are many criteria that may be used to determine which subset of lesions is returned. Criteria may include, without being limited to: the most similar lesions; the most similar lesions from each of a selection of categories, e.g.: benign and malignant; different subtypes of lung cancer; different types of lesions (infection, fibroma, cancer, etc.); the most similar lesions which specific morphological characteristics selected by the user (e.g., lesions with spiculations; ground glass lesions; hypoenhancing lesions, etc.); the most similar lesions from patients with similar demographic or clinical characteristics to the patient from whom the query lesion is drawn; or any combination of the above.

In at least some implementations, the returned results are used as input to an algorithm that classifies the query lesion at 2918. The classification algorithm may predict for the query lesion any clinical outcome that is known for the lesions retrieved from the CBIR database 2912. For example, the classifier may classify the malignancy, lesion type, cancer subtype or prognosis of the query lesion. The classifier may be a K-nearest-neighbors algorithm that generates a result based on majority voting of the returned results, or it may be a more sophisticated algorithm, such as a random forest or gradient boosted decision trees. The classification may include the probability associated with the most likely predicted class as well as the probabilities associated with other classes. The results may include the uncertainty of the prediction. The uncertainty may be expressed as a confidence interval or in colloquial language that indicates the degree to which the classifier is confident in its prediction.

Figure 30:
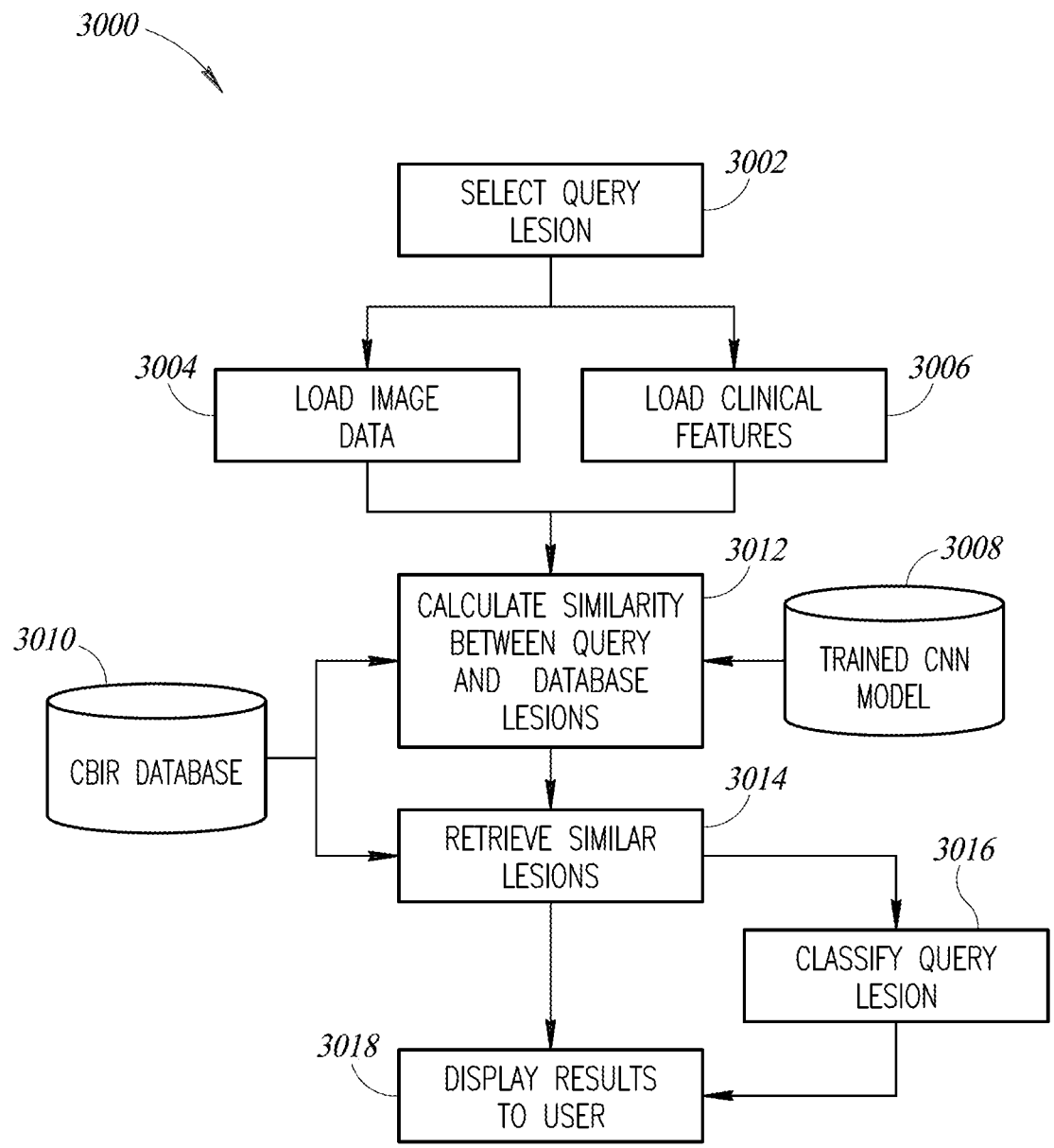
FIG. 30 is a schematic block diagram of a content based image retrieval process according to an implementation wherein a convolutional neural network operates to provide predictions of similarity.

After similar lesions are retrieved, the similar lesions, along with the classification result (if applicable in the given implementation) are displayed to the user of the software at 2920. Additional details and different possible implementations of the user interface are discussed elsewhere herein. FIG. 30 shows a method 3000 for an alternative implementation for inference in which a CNN is used to directly predict similarity. As in the previous implementation of the method 2900, the query lesion is selected at 3002, image data is loaded at 3004 and, in at least some implementations, clinical features are loaded at 3006. One difference between the implementation of the method 3000 and the implementation of the method 2900 is that, in the implementation of the method 3000, the trained CNN model 3008 is not used to extract features. Rather, the trained CNN model 3008 directly predicts at 3012 the similarity of the query lesion to lesions from the CBIR database 3010. The CNN model takes as input image data and, in some implementations, clinical features. Although the image data is used as input to the first CNN layer, if clinical features are used as input, the clinical features may be used as input to the CNN at any layer; for example, they may be used as input to the last layer (the layer closest to the output) of the CNN. The output of the CNN model is a similarity value between the query lesion and lesions from the CBIR database 3010.

The remaining sections of the method 3000, including retrieval of similar lesions at 3014, optional classification at 3016, and displaying the results to the user at 3018, operate identically to the analogous sections in the method 2900 discussed above.

Inference User Interface

Figure 31:
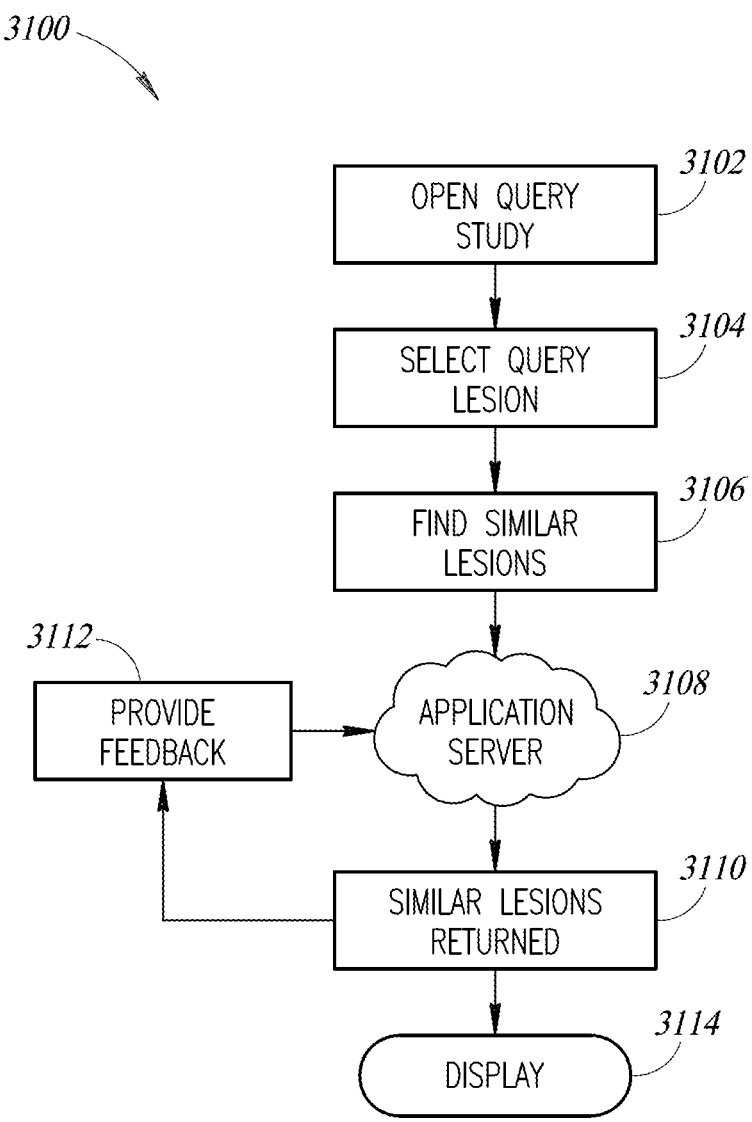
FIG. 31 is a schematic block diagram of a user interface of a content based image retrieval system, according to one non-limiting illustrated implementation.

FIG. 31 shows a method 3100 of implementing a user interface with which the user can interact with the CBIR system. Within the software application, the user initially opens the relevant study from which they wish to invoke CBIR at 3102. Within the study, the query lesion is selected at 3104, as described previously. From there, a Find Similar Lesions process is invoked at 3106. The Find Similar Lesions process may be invoked manually by the user, or it may be invoked automatically once the query lesion is selected at 3104. The request to find similar lesions is sent to the application server 3108 which may either be a remote server or it may reside on the user's computer. Similar lesions are returned at 3110 and then displayed to the user on a display at 3114. In at least some implementations, the probability of malignancy or some other metric for the query lesion is simultaneously displayed. In implementations for which such a metric is displayed, the metric may be displayed simultaneously with the returned lesions, or it may be displayed in a separate interface. In at least some implementations, the metric is displayed as a bar chart or number indicating the probability of the given metric (e.g., malignancy).

In at least some implementations, the user has the option of providing feedback on the returned results at 3112. The feedback mechanism may take on any of several forms, including but not limited to: the user may indicate on specific results whether they deem them to be similar or dissimilar to the query lesion; the user may indicate on specific results whether they deem them to be relevant or irrelevant to the specific treatment decision (e.g., whether or not to biopsy the query lesion) that the clinician wishes to make; the user may directly assign similarity scores or relevancy scores to the individual results; the user may re-order the results based on their preferred ordering of similarity or relevance; or any combination of the above.

Figure 32:
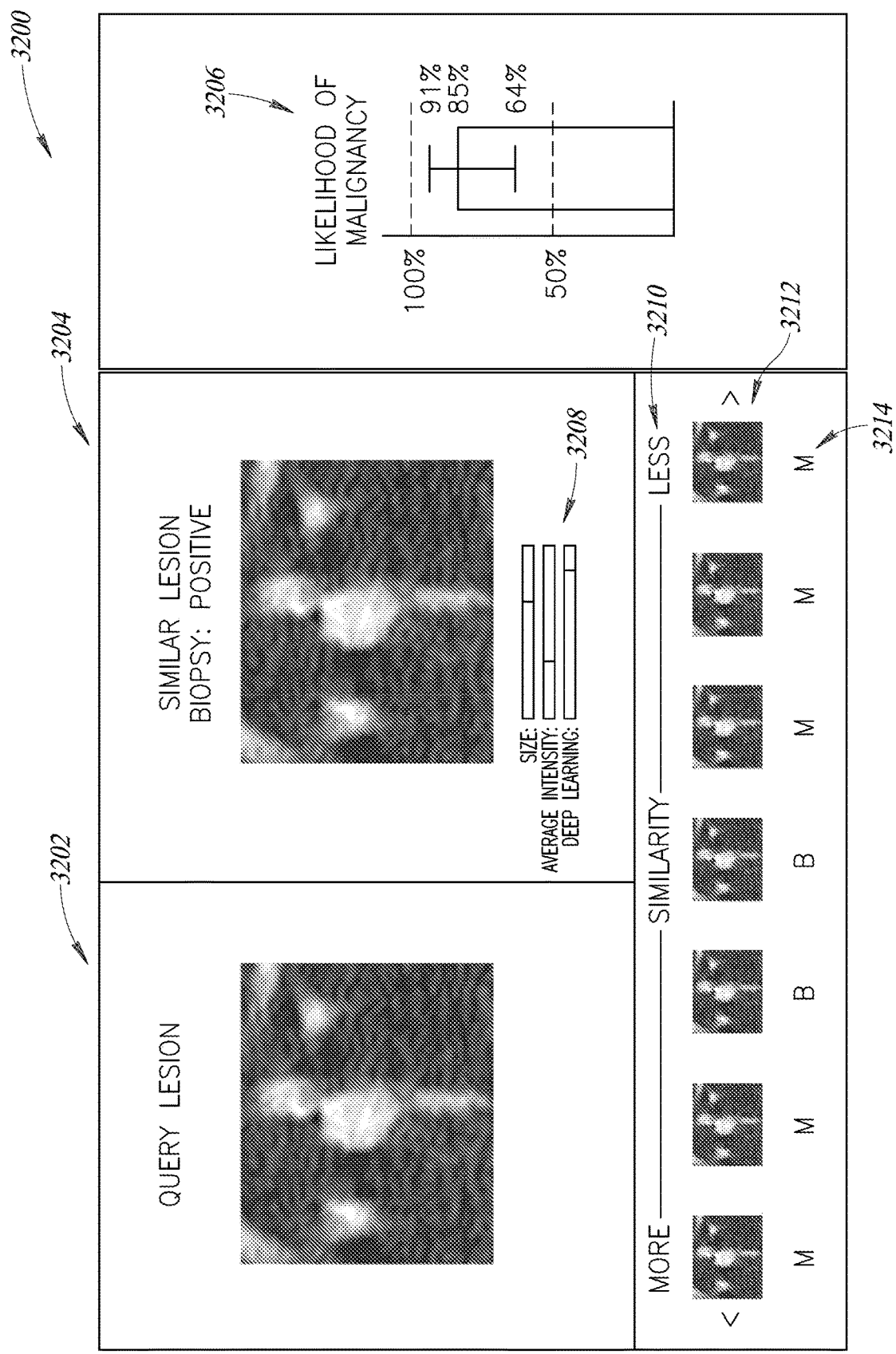
FIG. 32 illustrates one implementation of a results user interface of a content based image retrieval system, according to one non-limiting illustrated implementation.

FIG. 32 shows one implementation of a user interface 3200. In particular, FIG. 32 shows the user interface 3200 for returned results 3214. The query lesion 3202 is shown alongside the current selected similar lesion 3204. Characteristics of the current selected similar lesion 3204, such as the biopsy result, are shown. In at least some implementations, the current selected similar lesion 3204 may be displayed larger, possibly in its own window, hiding other elements of the user interface 3200. Degrees of similarity of the current selected similar lesion along different similarity dimensions may be displayed 3208. In this implementation, three dimensions, including "size," "average intensity" and "deep learning" are shown. Other implementations may show similarity across additional dimensions, different dimensions or not at all. Additional similar lesions beyond the current selected similar lesion 3204 that is currently selected are shown below in a scrollable interface 3212. The user may interact with one of the other similar lesions 3212. Upon interaction, that similar lesion becomes the current selected similar lesion.

The user may browse additional similar lesions beyond those shown by clicking the arrows on either side of the list of similar lesions. In other implementations, the user may also scroll through the list using a mouse scroll wheel, a touch interface, clicking and dragging or keyboard shortcuts. In this implementation, a summary of the returned lesion characteristics, namely whether the lesion is known to be malignant (M) or benign (B) is indicated alongside the results 3214, but this information could be displayed in another way (e.g., using color or a shape, or overlaid on the images). Other information about the lesions (e.g., the known cancer subtype) could be displayed. In this implementation, the likelihood of malignancy 3206 of the query lesion is displayed. In this implementation, the likelihood is displayed as a bar graph with error bars, though other forms of display, including other types of graphs or a textual percent are also possible. Other predicted results, e.g., the probabilities of different cancerous subtypes can also be displayed. In at least some implementations, the predicted results 3206 may be derived from statistical analysis of the returned similar lesions 3212. In at least some implementations, predicted results 3206 are not shown.

Figure 33:
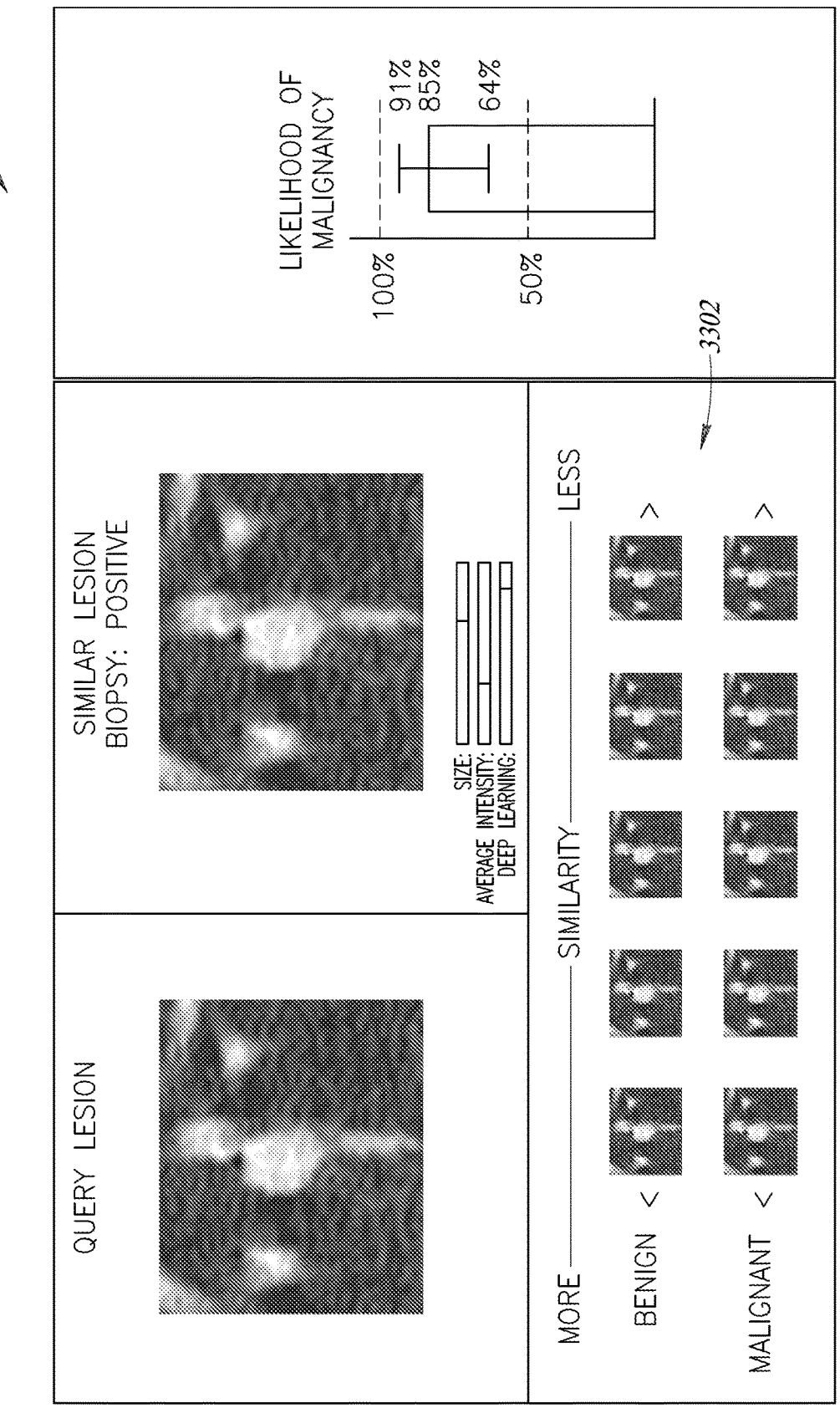
FIG. 33 illustrates another implementation of a results user interface of a content based image retrieval system, wherein returned results are stratified by malignancy, according to one non-limiting illustrated implementation.
Figure 34:
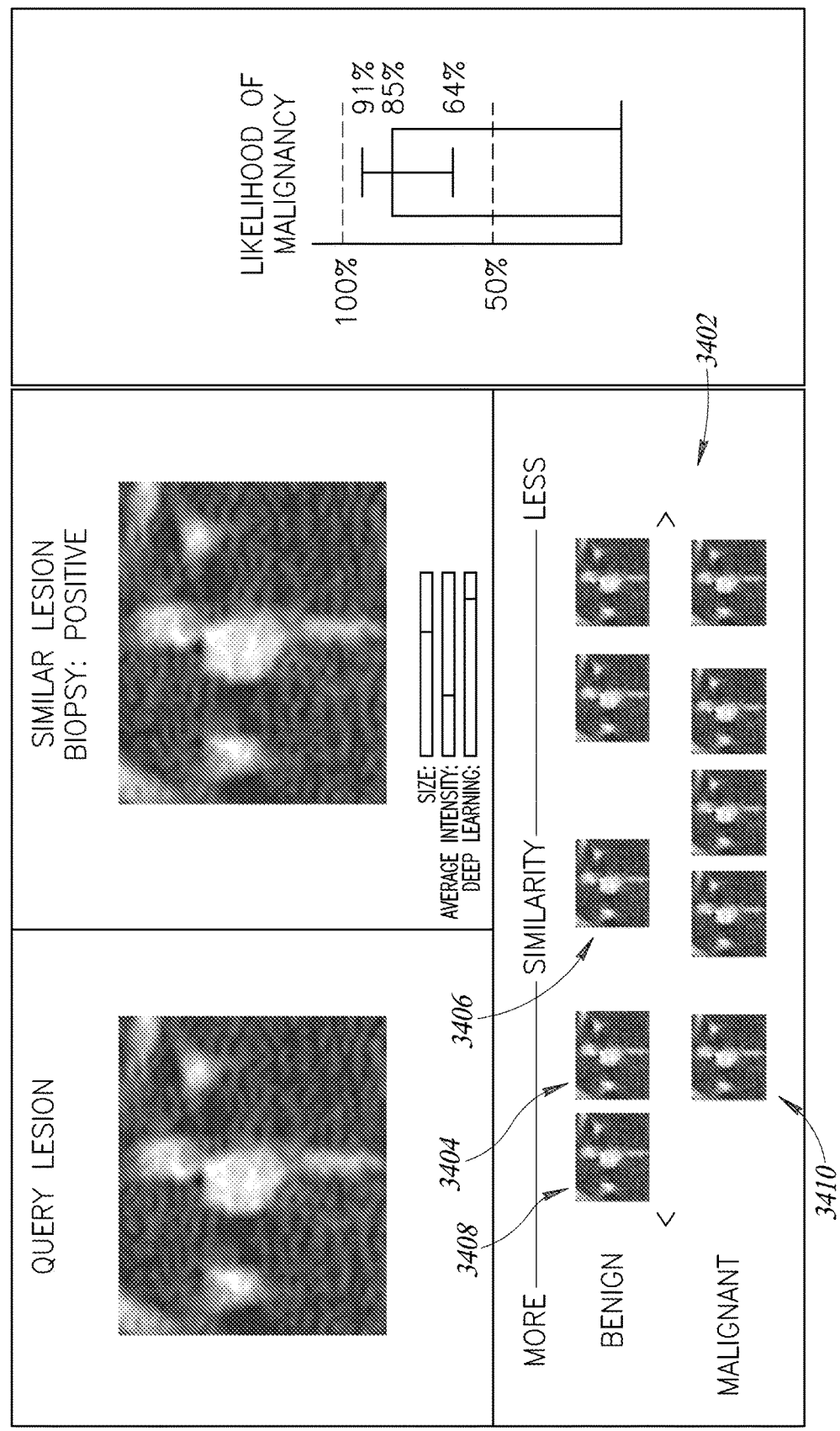
FIG. 34 illustrates another implementation of a results user interface of a content based image retrieval system, wherein returned results are stratified by malignancy and arranged spatially according to similarity, according to one non-limiting illustrated implementation.

FIG. 33 shows a view of a user interface 3300 that provides an alternative implementation of displaying returned lesions. In this implementation, returned lesions are stratified into sections based on biopsy-confirmed malignancy 3302, with benign lesions shown separated from malignant lesions. Any characteristic of the lesions, such as known cancerous subtype, or different types of lesions (including both benign and malignant types) can be used to stratify the display of returned lesions. FIG. 34 shows a view of a user interface 3400 that provides an alternative implementation of displaying returned lesions. This implementation is similar to the implementation shown in FIG. 33, except that, instead of returned lesions shown spaced equidistant from each other, the distances of the lesions with respect to each other in the returned lesion display 3402 are based on the actual similarity of the lesions with respect to each other. For example, the small gap between the leftmost two lesions 3408 and 3404 in the benign category indicates that those two lesions are similar to each other. The large gap between the second and third benign lesions 3404 and 3406, respectively, indicates that those lesions are relatively more dissimilar to each other. The fact that the first malignant lesion 3410 is further to the right than the first benign lesion 3408 indicates that the first malignant lesion 3410 is less similar to the query lesion than the first benign lesion 3408 is to the query lesion. In at least one implementation, the benign and malignant rows of lesions scroll synchronously to preserve the similarity relationships between the two rows. Stratifications other than benign and malignant, such as lesion subtype, could also be used.

Figure 35:
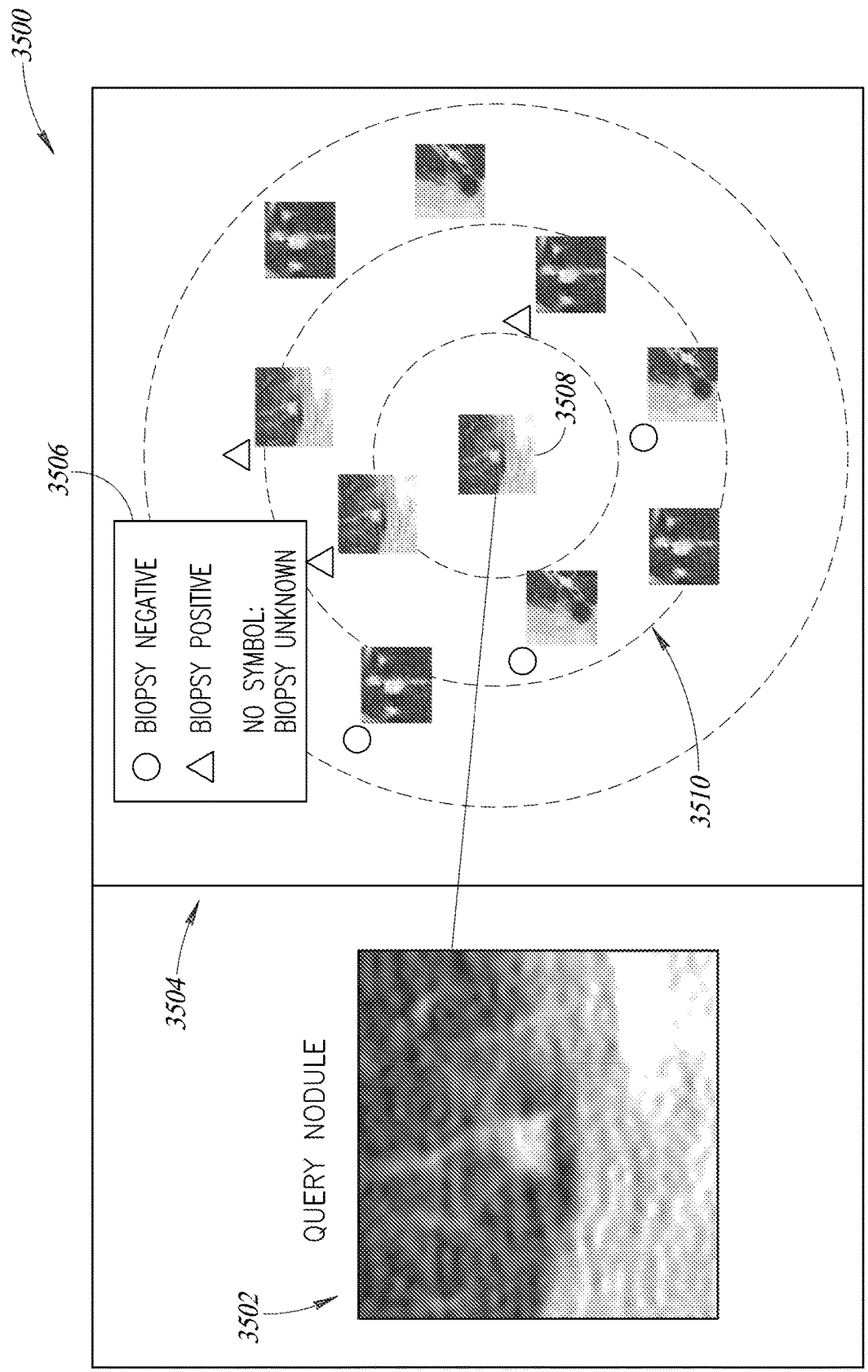
FIG. 35 illustrates another implementation of a results user interface of a content based image retrieval system, wherein returned results are shown in a two-dimensional radial diagram, according to one non-limiting illustrated implementation.

FIG. 35 shows a view of a user interface 3500 that provides an alternative implementation of displaying returned lesions. As in other implementations described here, the query lesion is shown 3502. In at least some implementations, the query lesion 3502 is not separately shown. In this implementation, returned similar lesions are shown in a two-dimensional polar plot 3504. The polar plot 3504 represents two dimensions of similarity between returned lesions and the query lesion; the overall distance on the polar plot from its center 3508 represents the overall distance (inversely proportional to similarity) between a given returned lesion and the query lesion. The dimensions may be two features that are used in the calculation of similarity, or they may be two features that result from dimensionality reduction of a higher dimensional feature space, such as through principal component analysis (PCA) or t-Distributed Stochastic Neighbor Embedding (t-SNE). The query lesion is shown at the center of the polar plot 3508 for reference. Contours 3510 indicate lines of equal distance from the query lesion. Returned lesions are indicated on the polar plot using thumbnail images of the lesions. Returned lesions could also be represented with markers that do not show the lesion image. In this implementation, the biopsy result of returned lesions is indicated by the color of the image border and a symbol (circle for biopsy negative, triangle for biopsy positive) 3506. The biopsy result could be indicated via other means, such as the shape of the thumbnail image, a symbol adjacent to the image, or a text overlay. If the returned images are represented with markers, the marker type (e.g., square vs. diamond) could indicate the category of lesion (e.g., benign vs. malignant). Other categories besides benign or malignant, such as the lesion subtype of the returned lesions, could alternatively or additionally be indicated.

C. THREE DIMENSIONAL VOXEL SEGMENTATION TOOL

Medical imaging, such as CT and MR, is frequently used to create a 3D image of anatomy from a stack of 2D images, where the 3D image then includes a three dimensional grid of voxels. While the technique is extremely powerful, its three dimensional nature frequently presents challenges when trying to interact with the data. For example, the simple task of viewing the resulting volume requires specialized 3D rendering and multiplanar reconstruction techniques.

A common task for a radiologist is to segment some feature within the 3D volume. One example would be indicating all of the voxels of a 3D volume that make up a tumor. This would be important to help measure the tumor and track its change over time. Another example would be segmenting the volume of the left and right ventricles of the heart along with the myocardium at end systole and end diastole in order to determine heart function.

In order to deal with the challenges presented by trying to work in three dimensional space, usually using two dimensional tools such as a computer screen and mouse, various techniques have been developed.

A radiologist may characterize a tumor based on one or more simple measurements, such as the tumor's diameter, implemented as a simple linear measurement. Such measures are not as ideal as keeping track of all the voxels in a tumor, but are relatively simple to implement.

Similarly, it is very common to segment features such as the left ventricle of the heart by establishing a set of regularly spaced 2D slices through the feature and then creating contours on each of the slices which can then be connected to produce a representation of the three dimensional segmented region. This technique works well for some shapes, such as the left ventricle, although the process of drawing contours on many slices can be time consuming. Other anatomy features have more complex shapes and are not easily represented by a series of contours, making their segmentation much more difficult.

One or more implementations of the present disclosure are directed to systems, methods and articles that allow a user to interact with 3D imaging data. In at least some implementations, the system allows a user to move an adjustable radius sphere (or cylinder), also referred to herein as an editing tool, within a volume in order to add voxels to a segmentation. The action can be thought of as using the sphere to paint the voxels of interest. One way to visualize a 3D volume is to produce a multiplanar reconstruction (MPR) of the volume, creating a 2D image representing a slice through the volume at some arbitrary position and orientation. The placement and movement of the sphere may be controlled by the user clicking and dragging (e.g., via a mouse or other pointer) on such an MPR representation of the volume. By alternating between adjusting the position and orientation of the MPR and using an editing tool of the system, the user is able to quickly segment a region of interest as defined by the current application. As the user edits the segmentation, the editing tool may be displayed to the user as a circle on the MPR. The current extent of the segmentation may also be displayed to the user by constantly updating the MPR as the user makes an edit and highlighting the MPR pixels that fall within the segmentation.

While a sphere is an appropriate shape for adding voxels to a segmentation to fill a region of the volume, a sphere may not work well for removing voxels in a well-controlled manner. For this purpose, the application may create an infinitely long cylinder with the axis of the cylinder perpendicular to the plane of the MPR with which the user is interacting. The cylinder then acts like a "knife" that can effectively cut away parts of the segmentation.

The application maintains a list of independent segmentations and provides the ability to distinguish different types of segmentations as defined by the current task. For each segmentation the application also displays the total volume of the segmented voxels and other measurements of the segmentation's physical extent.

The following provides a description of one possible implementation of the present disclosure.

The user is able to view either a single MPR of the volume or a collection of three orthogonal MPRs along with a 3D rendering of the volume. As with most medical image viewing software, controls are provided to easily manipulate the position and orientation of the MPRs so that the user can get the desired view of the anatomy feature of interest.

Figure 36:
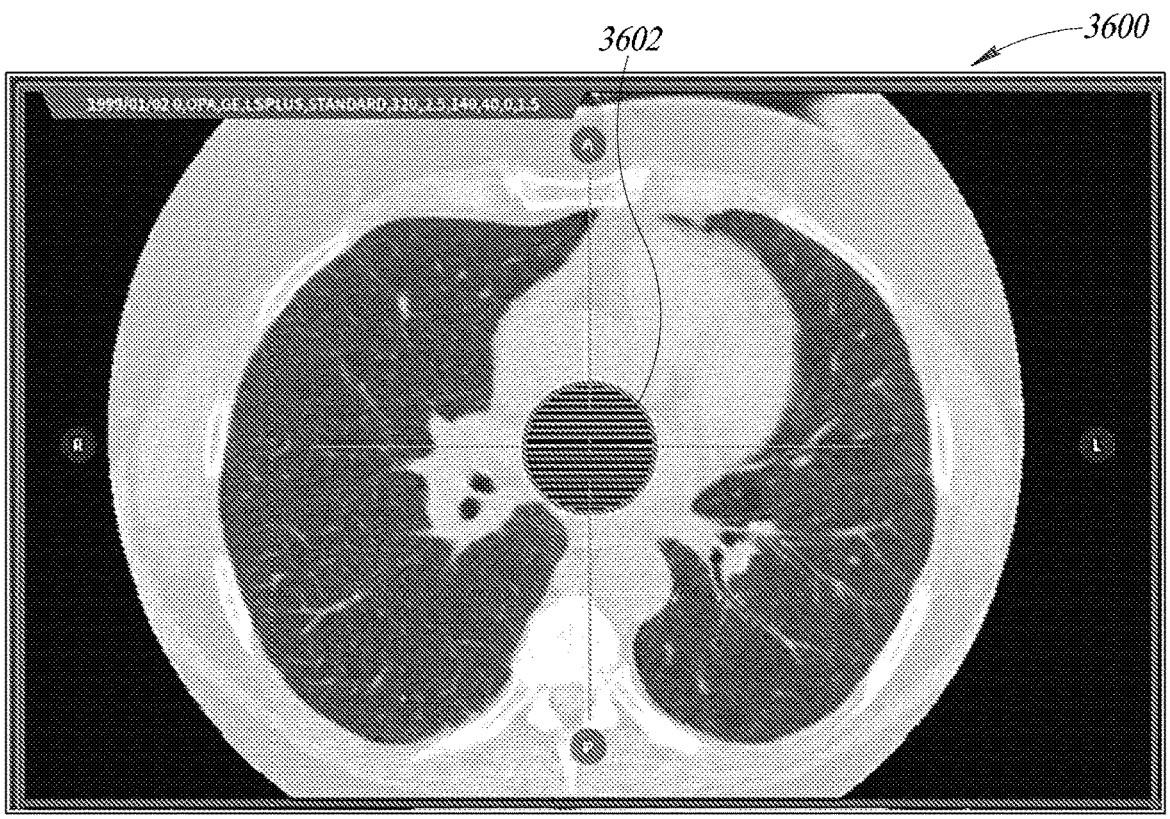
FIG. 36 is a screenshot of a user interface of a three-dimensional voxel segmentation tool, according to one non-limiting illustrated implementation.
Figure 37:
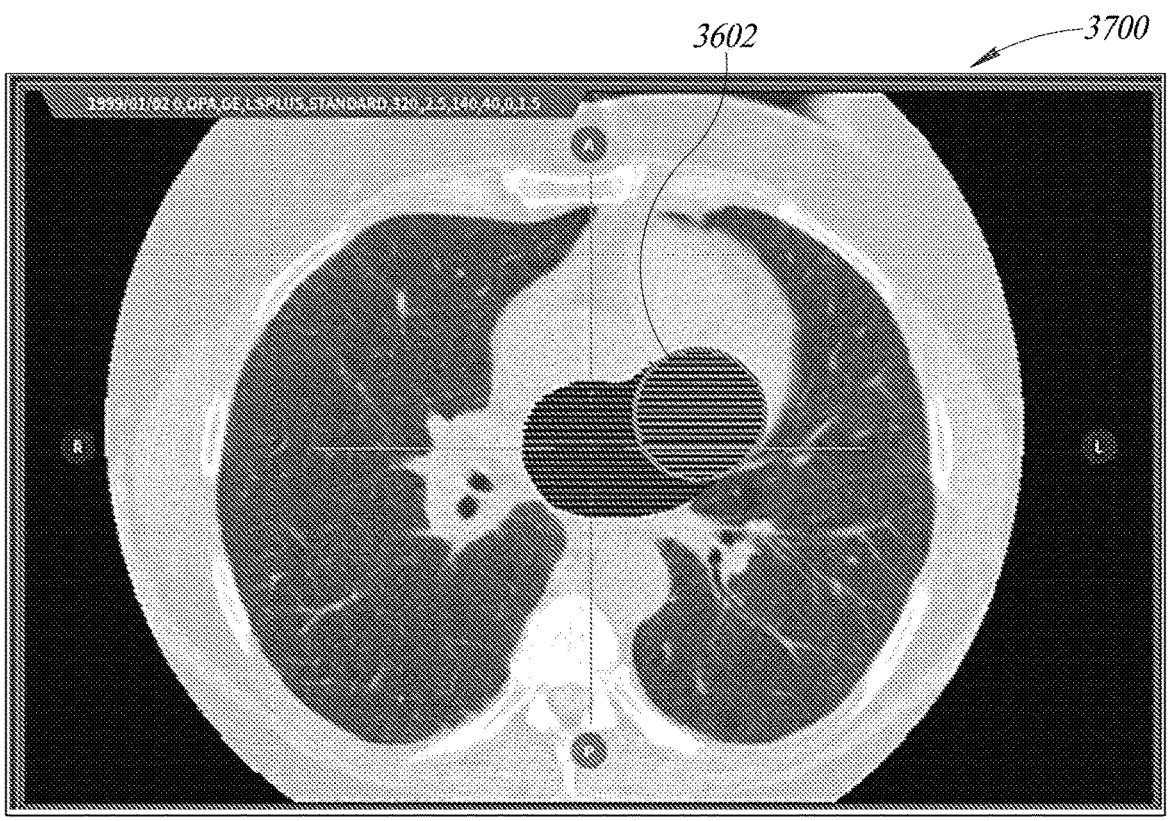
FIG. 37 is a screenshot of a user interface of a three-dimensional voxel segmentation tool, showing hove moving a pointer adds voxels to a segmentation, according to one non-limiting illustrated implementation.
Figure 38:
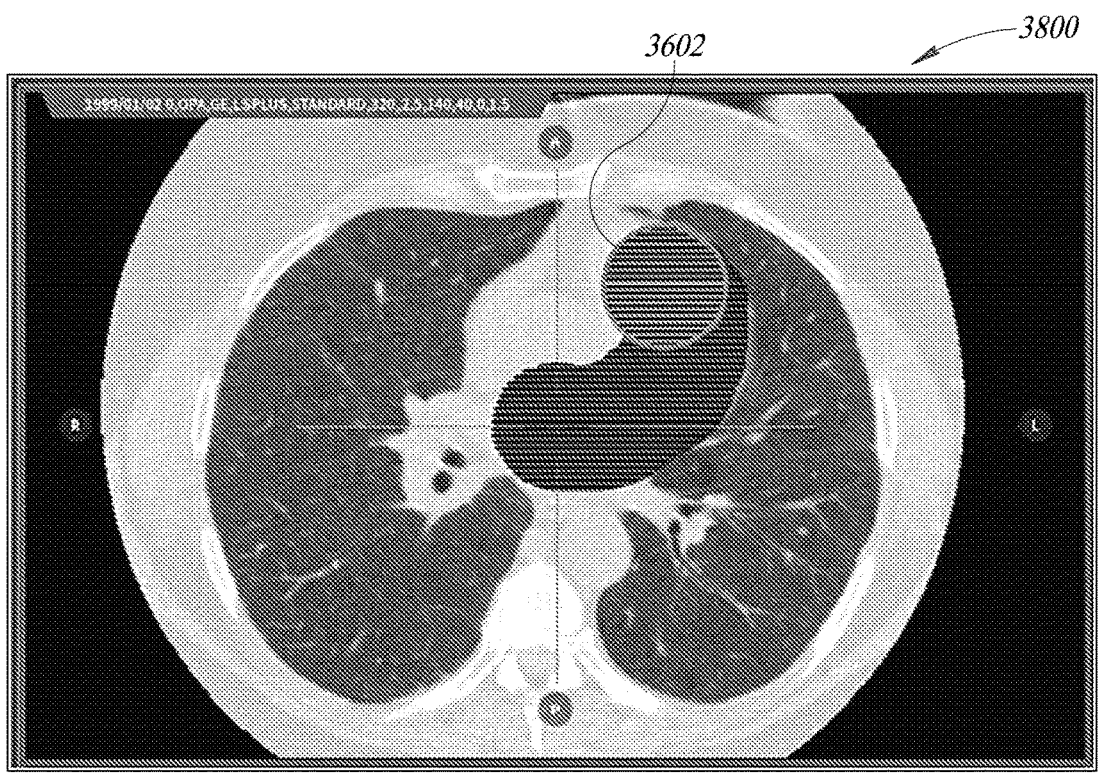
FIG. 38 is a screenshot of a user interface of a three-dimensional voxel segmentation tool, showing how a segmentation grows as a sphere follows movement of a pointer until the pointer is deactivated, according to one non-limiting illustrated implementation.

A tool is then provided that allows the user to create a 3D segmentation by clicking and dragging on one of the displayed MPRs. Voxels are added to the segmentation by moving an editing tool (e.g., a sphere) through the volume. As shown in a screenshot 3600 of FIG. 36, in at least some implementations, when a user clicks on some point within one of the MPRs, a sphere 3602 is initialized at that point within the 3D volume. The intersection of the MPR with the sphere is displayed to the user as a circle on the MPR itself, providing feedback to the user. As the sphere is moved through the volume guided by the user dragging the sphere's center point over the MPR, the voxels that come in contact with the sphere are added to the segmentation. This feature is shown in the screenshot 3700 of FIG. 37 and the screenshot 3800 of FIG. 38. The segmentation itself keeps track of all the voxels that it contains and is typically implemented by marking a mask of the volume's voxels. The segmentation grows as the sphere follows the mouse movement until the mouse button is released.

As the current segmentation is edited, the MPRs are continually updated in order to display the intersection of the MPR with the segmented volume. This may be done by applying a color highlight to intersecting pixels of the MPR. Because MPRs are only capable of displaying 2D cross sections of the resulting segmentation, it can be advantageous for the radius of the editing sphere to be easily adjustable to so that it is an appropriate size for the feature being marked. It is also very useful to have a tool that allows the user to easily rotate the orientation of the MPRs around a center point, which can be placed within the segmentation, so that the user can quickly get an idea of how well the segmentation is proceeding and quickly find new orientations where the segmentation needs further edits.

Figure 39:
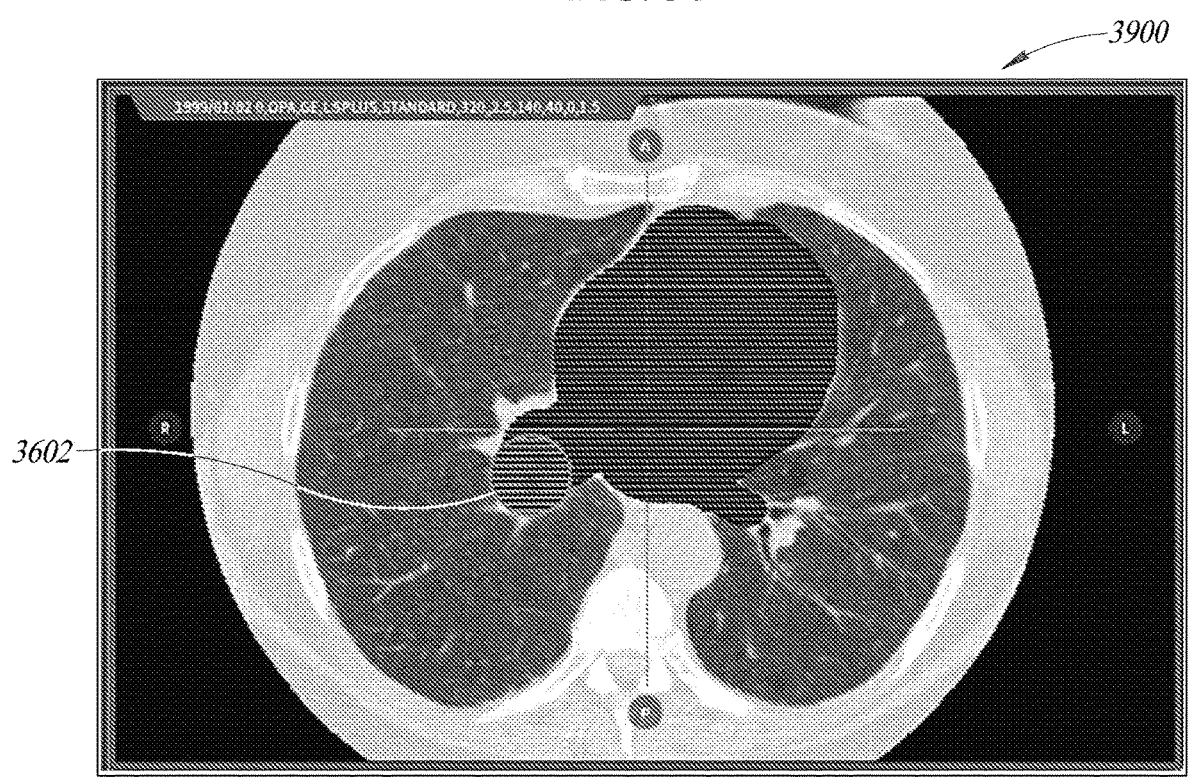
FIG. 39 is a screenshot of a user interface of a three-dimensional voxel segmentation tool, showing that selecting a point inside an existing segmentation initializes a tool that adds voxels to the segmentation, according to one non-limiting illustrated implementation.
Figure 40:
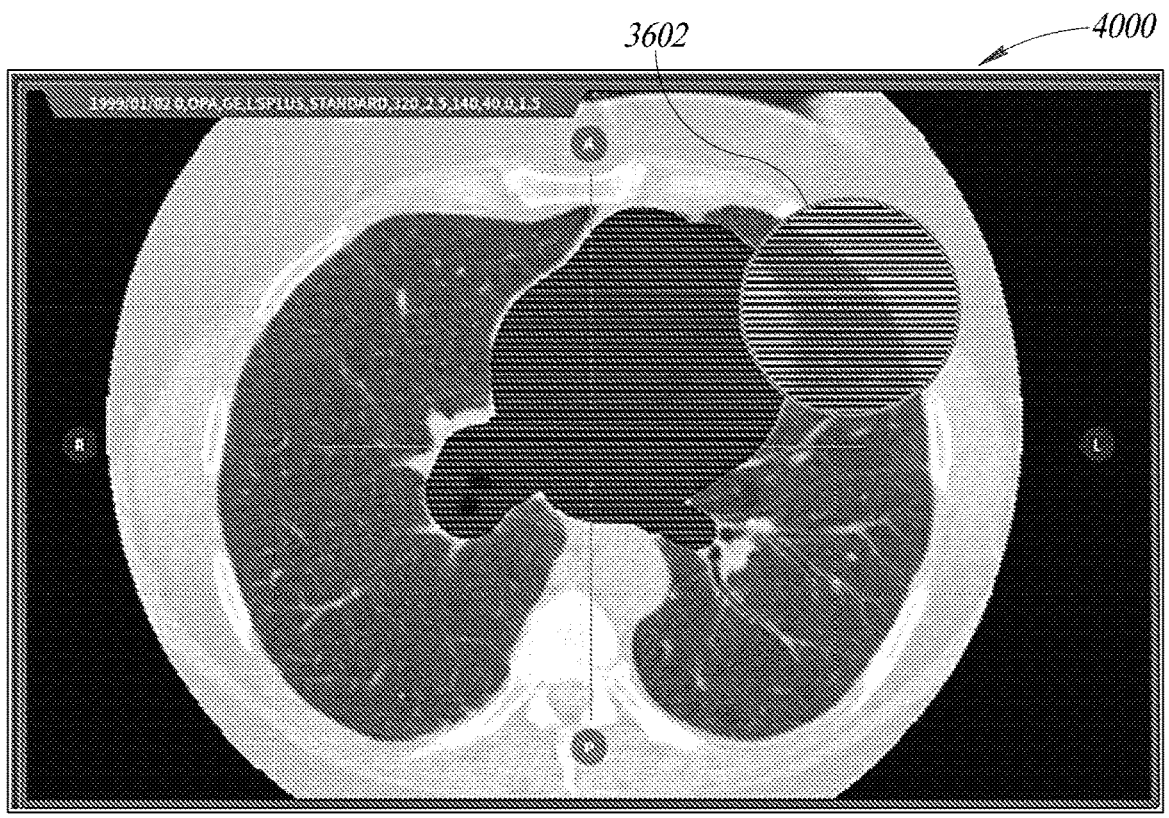
FIG. 40 is a screenshot of a user interface of a three-dimensional voxel segmentation tool, showing that selecting a point outside an existing segmentation initializes a tool that removes voxels from the segmentation, according to one non-limiting illustrated implementation.

In addition to being able to add voxels to a segmentation, the system may allow a user to easily remove voxels from a segmentation in order to make corrections. In this particular implementation, a user indicates their desire to add more voxels to an existing segmentation by placing the initial click of the drag operation inside the segmentation itself, as shown in the screenshot 3900 of FIG. 39. In a similar manner, placing the initial click of the drag operation outside the segmentation triggers a removal or trimming operation, as shown in the screenshot 4000 of FIG. 40.

Figure 41:
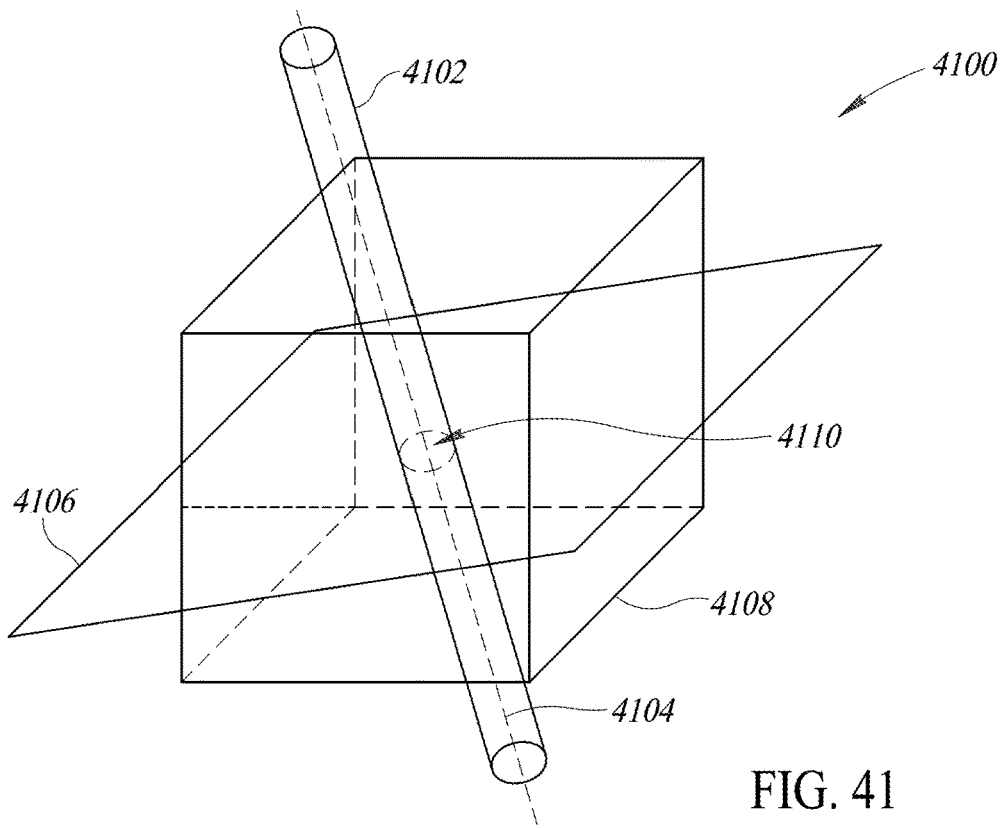
FIG. 41 is a schematic diagram that illustrates an adjustable radius editing cylinder that may be used by the three-dimensional voxel segmentation tool to modify segmentations, according to one non-limiting illustrated implementation.

While a sphere is a suitable shape for adding voxels to a segmentation, a sphere may not be particularly well-suited for removing voxels. As shown in a diagram 4100 of FIG. 41, when a user indicates that voxels are to be removed (e.g., by placing the initial click of the drag operation outside the segmentation), in at least some implementations the sphere is replaced with an adjustable radius cylinder 4102, the axis 4104 of which is perpendicular to the MPR 4106 with which the user is currently interacting. The representation of the cylinder on the MPR may still be a circle 4110 of the same radius as when the editing operation uses a sphere, but the cylinder is projected over the entire depth of the volume 4108, forming, in essence, a "knife" that is used to cut or trim the segmentation over its full depth. In this way removal of voxels from the segmentation becomes a predictable and controllable operation even under the constraint that the user is only able to see the result of the immediate operation on a 2D plane.

Figure 42:
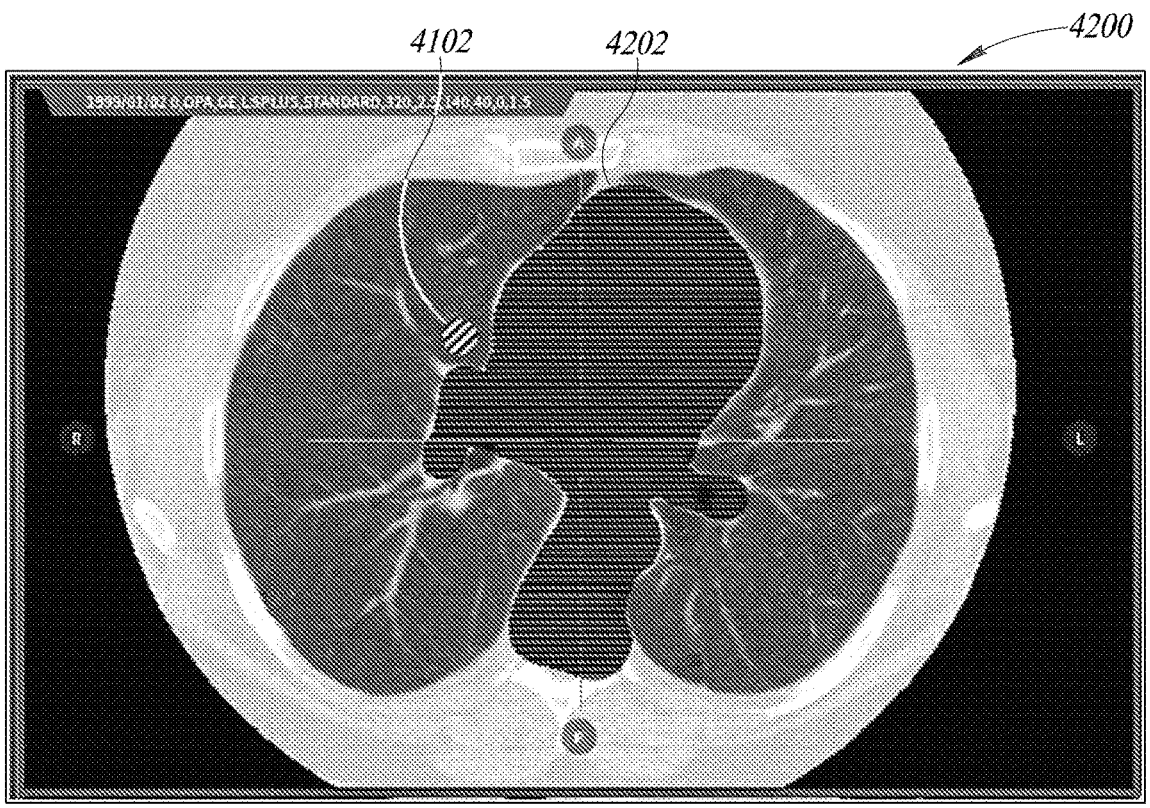
FIG. 42 is a screenshot of a user interface of a three-dimensional voxel segmentation tool, showing an editing cylinder approaching an existing segmentation, according to one non-limiting illustrated implementation.
Figure 43:
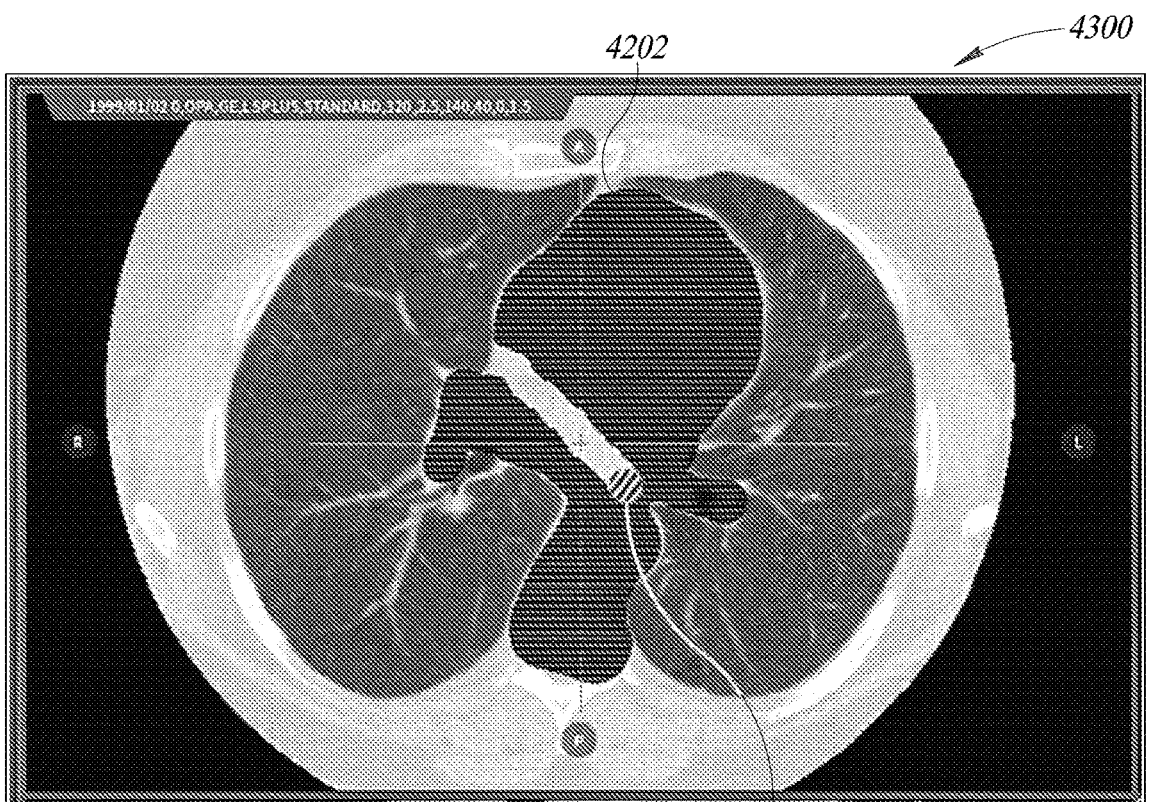
FIG. 43 is a screenshot of a user interface of a three-dimensional voxel segmentation tool, showing that the editing cylinder has cut most of the way through a segmentation, according to one non-limiting illustrated implementation.
Figure 44:
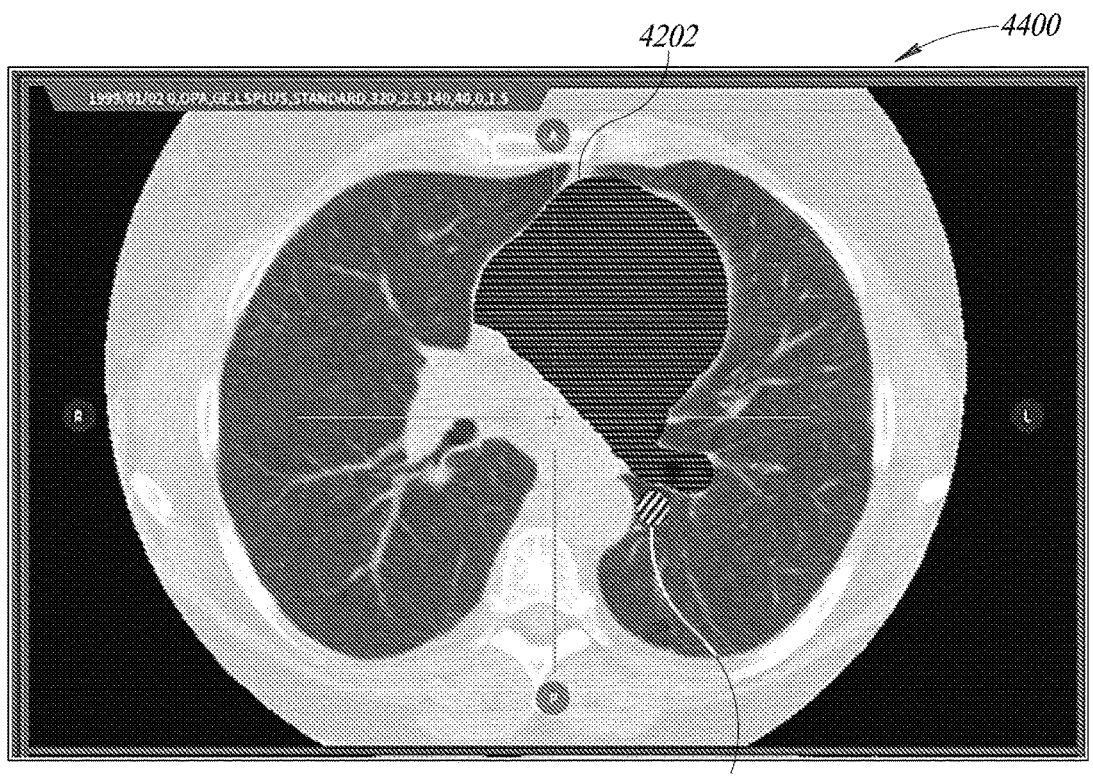
FIG. 44 is a screenshot of a user interface of a three-dimensional voxel segmentation tool, showing that the editing cylinder has cut all of the way through a segmentation resulting in the removal of a small connected region, according to one non-limiting illustrated implementation.

When doing this removal operation, it is very easy to deliberately or accidentally isolate different regions of an existing segmentation, for example, the user may use a small radius to cut a segmentation in half. When this happens, in at least some implementations, the system locates and keeps the largest connected resulting region of the segmentation and eliminates all resulting regions that have been cut off from it. This is done so that the end result is guaranteed to be a single connected region, which is advantageous for many uses of the segmentation tool. Allowing only a single connected region may also be advantageous because it helps the user keep control of the segmentation given that they cannot see all of the entire 3D segmentation at the same time. That is, it helps avoid leaving random small disconnected bits while the user is deleting or trimming part of the segmentation. FIG. 42 shows a screenshot 4200 as the editing cylinder 4102 approaches an existing segmentation 4202, FIG. 43 shows a screenshot 4300 as the editing cylinder 4102 has cut most of the way through the segmentation 4202, and FIG. 44 shows a screenshot 4400 as the editing cylinder 4102 has cut all the way through the segmentation 4202 resulting in the removal of the smaller connected region from the segmentation.

In order to accommodate the need to be able to segment multiple regions, the functionality may be organized as a list of independent, possibly overlapping, segmentations, each of which defines a single connected region. Each region may be assigned a code, which is used to control the color of the segmentation when it is displayed to the user. In addition, each segmentation may be labeled with a type defined by the specific application or tool that generated the segmentation, making it easy for each application or tool to find and control its own segmentations when a study is reloaded at a later date. A control is provided to the user that allows them to toggle on and off the display of an individual segmentation or a whole group of segmentations.

Figure 45:
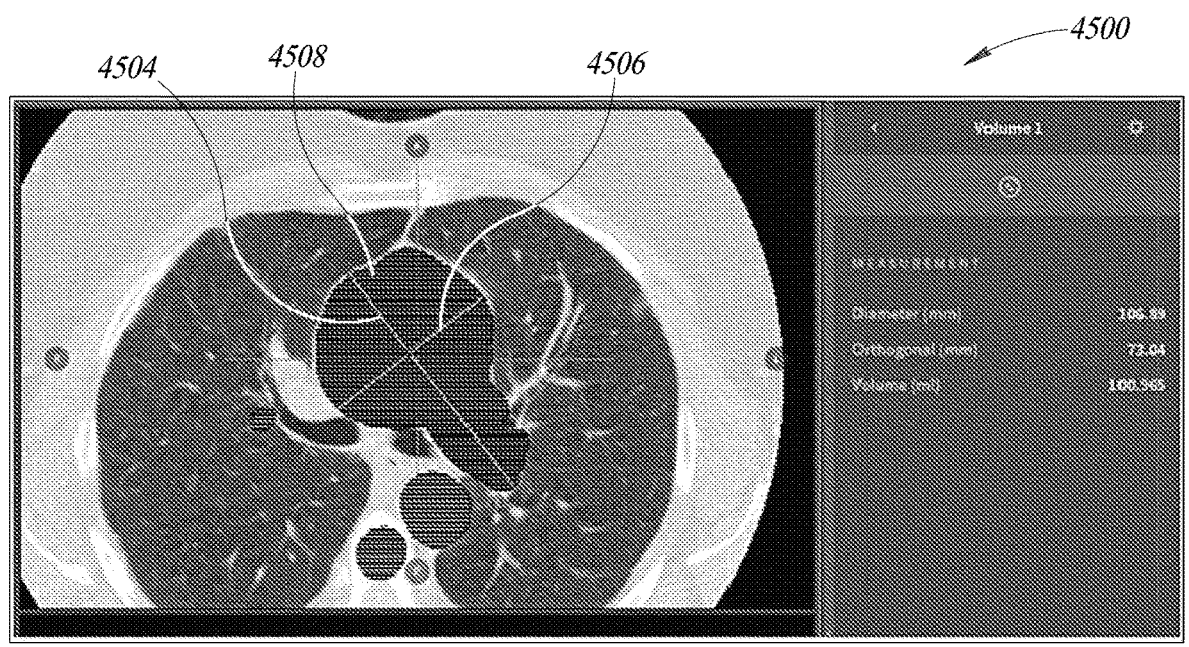
FIG. 45 is a screenshot of a user interface of a three-dimensional voxel segmentation tool, showing measurement details that are displayed for a selected segmentation, according to one non-limiting illustrated implementation.

FIG. 45 is a screenshot 4500 of the MPR that displays the regions covered by the individual segmentations shown in a list on the right hand side. The application further displays values associated with the physical extent of the segmentation, such as volume of the segmentation, the longest diameter of the segmentation, etc., as shown in the box 4502 on the right side of the screenshot 4500. In at least some implementations, the MPR displays the major diameter and the orthogonal diameter as lines 4504 and 4506, respectively, on a selected segmentation 4508.

When a segmentation is to be edited, it may first be put into a "selected" state, de-selecting any previously selected segmentation. In this way, the user is able to use the tool to interact with only a single segmentation at a time without needing to worry about accidentally editing neighboring or overlapping segmentations.

D. SYSTEMS AND METHODS FOR INTERACTION WITH MEDICAL IMAGE DATA

Current Clinical Practice for Radiological Estimation of Lesion Malignancy

One of the most important tasks that radiologists need to perform is the review of medical images, including magnetic resonance (MR) or computed tomography (CT), of patients who may have cancer. These patients may have imaging performed for a variety of reasons: they may be participating in cancer screening; they may have an unidentified mass from a clinical examination; they may have known cancer and are being imaged to track progression. As part of the review, the radiologist may discover potentially malignant lesions. They then need to make an assessment of the likelihood of malignancy of the lesions. Such an assessment will then lead to decisions for follow-up care for the patient, which may include any of the following: no treatment, follow-up imaging, biopsy, cancer treatment (such as radiation, surgery or chemotherapy) or others.

Because a lot of these assessments are subjective, the field of radiology has developed several standards for grading the findings in medical images. Depending on the type of cancer, these standards often include a combination of features such as size measurements, intensity of the pixels in images, response to contrast, growth rate, and diffusion properties amongst others. Some of these gradings are used for screening purposes, such as Lung-RADS (Lung Screening Reporting and Data System), which is used to assess the likelihood that a nodule found during a lung screening is malignant, and others are used to assess treatment response or disease progression, such as RECIST (response evaluation criteria in solid tumors), which uses linear dimensions to assess the growth or shrinkage of solid tumors.

These algorithms for calculating the score of a finding can be simple or complex, and the features can be easy to pinpoint or they may require an expert. In all cases, significant inter-reader variability exists when different clinicians assess the same scan, complicating communication with other physicians and decreasing the quality of the diagnostic decisions that are based on these variable assessments.

To make matters worse, radiologists today often spend time on very low-value tasks, such as aligning images from different series so they can compare findings over time, and opening scans on different software packages to make a complete assessment as imaging software has traditionally been applied for very specific tasks, such as measuring the volume of a finding, detecting disease or visualizing complex scans.

Figure 46A:
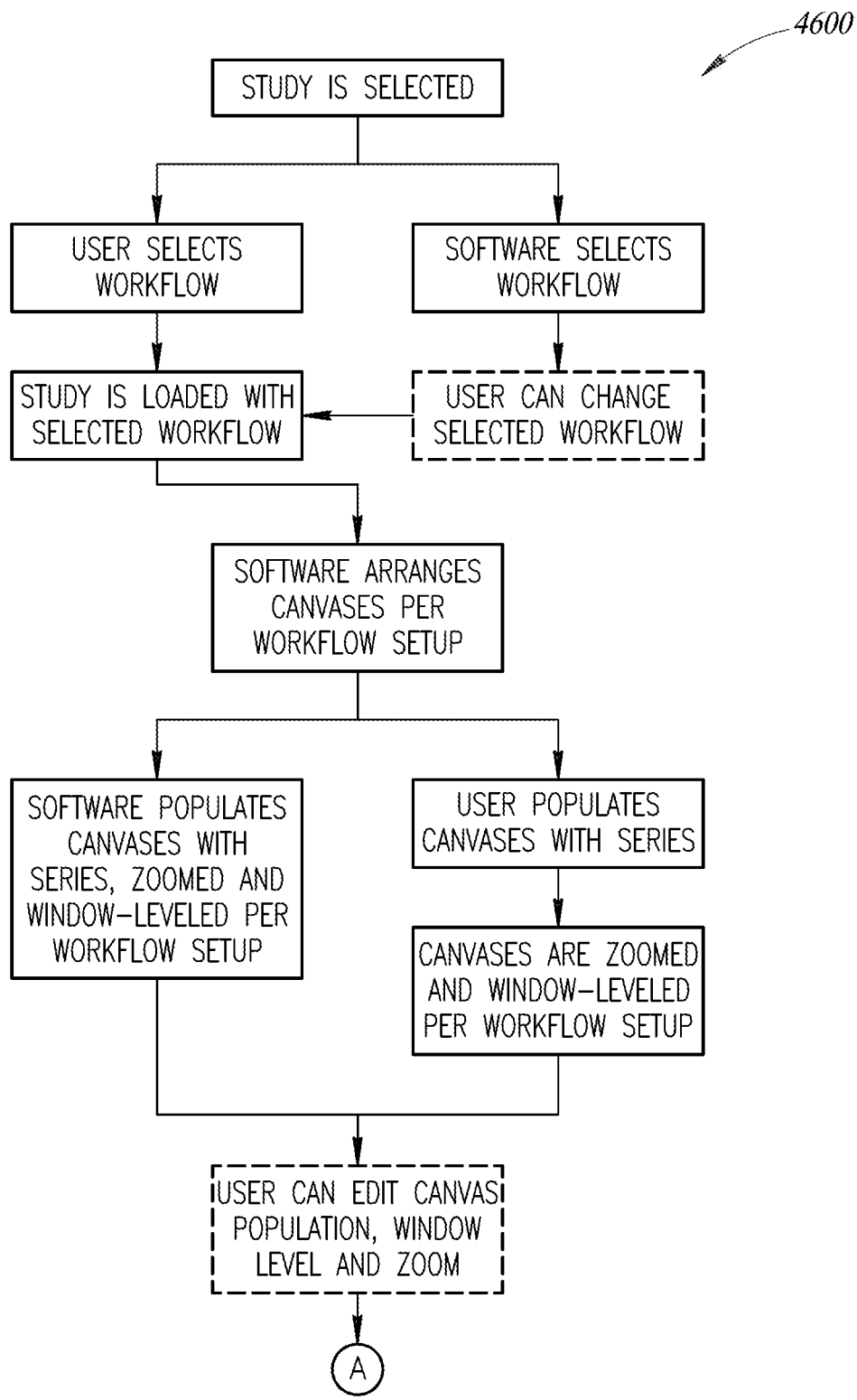
FIGS. 46A and 46B are a flow diagram of a method of operating a computer based system to interact with medical image data, according to one non-limiting illustrated implementation.
Figure 46B:
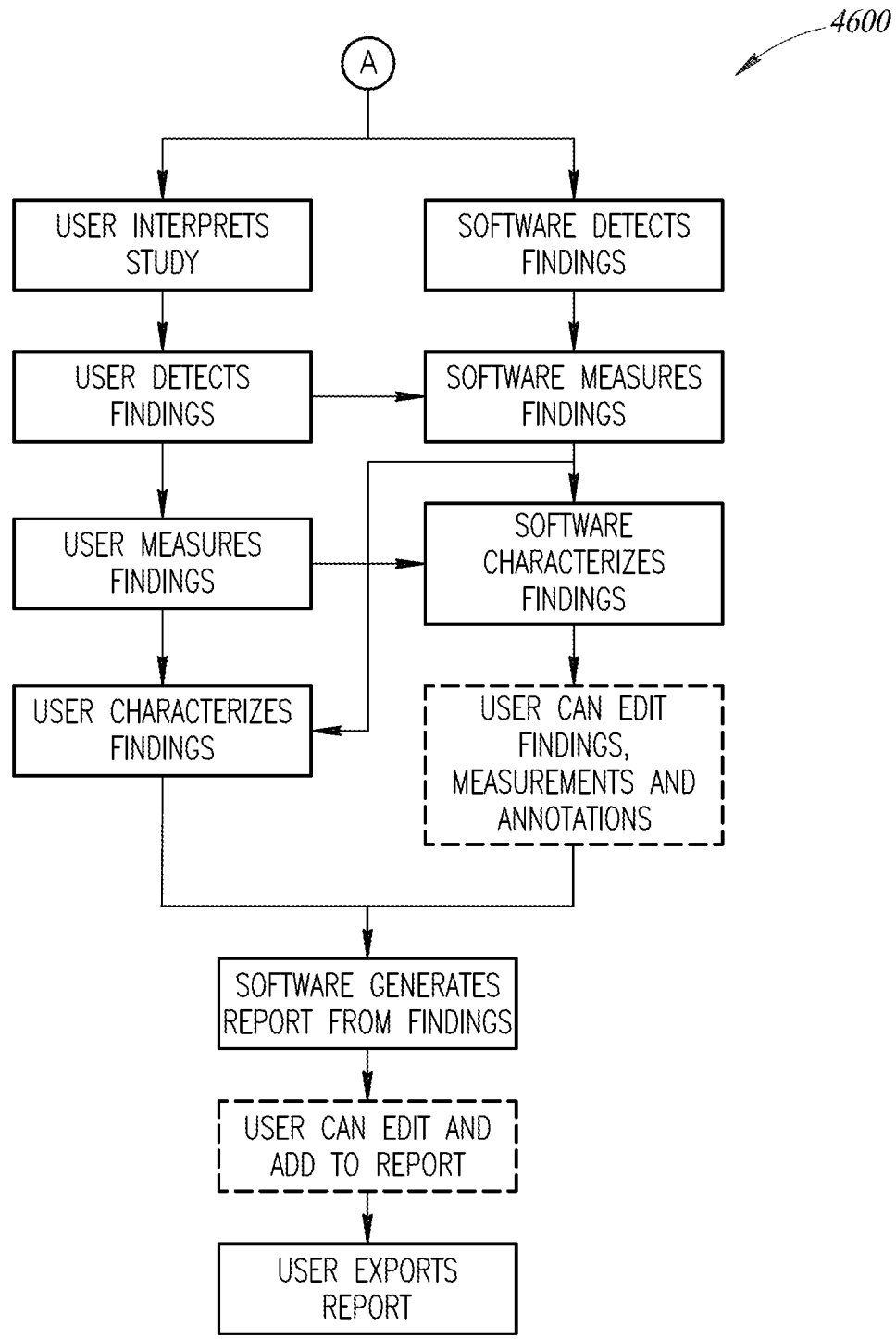

Implementations of the present disclosure are directed to system, methods and articles that provide users with a case-specific graphical user interface (GUI) and workflow to assist physicians in screening for, measuring and tracking specific conditions. FIGS. 46A and 46B show a non-limiting example of a workflow 4600, according to one non-limiting illustrated implementation. The workflow for each case is comprehensive, so that users can use a single piece of software for the tasks they need to perform on the scan. Workflow features may include automated features that can be manually overridden or also manually created including, but not limited to, series selection, image set-up, finding detection, finding measurement, tracking findings between scans, providing a GUI to annotate different features for each finding or the entire case, and reporting scores, findings and a case summary. The system offers unprecedented flexibility for combining automated and manual features, and editing the output of automated features.

1st Embodiment (CT Example): Lund Augmented Workflow

GUI that comprises automated and manual tools for chest CT analyses

Setup

Figure 47:
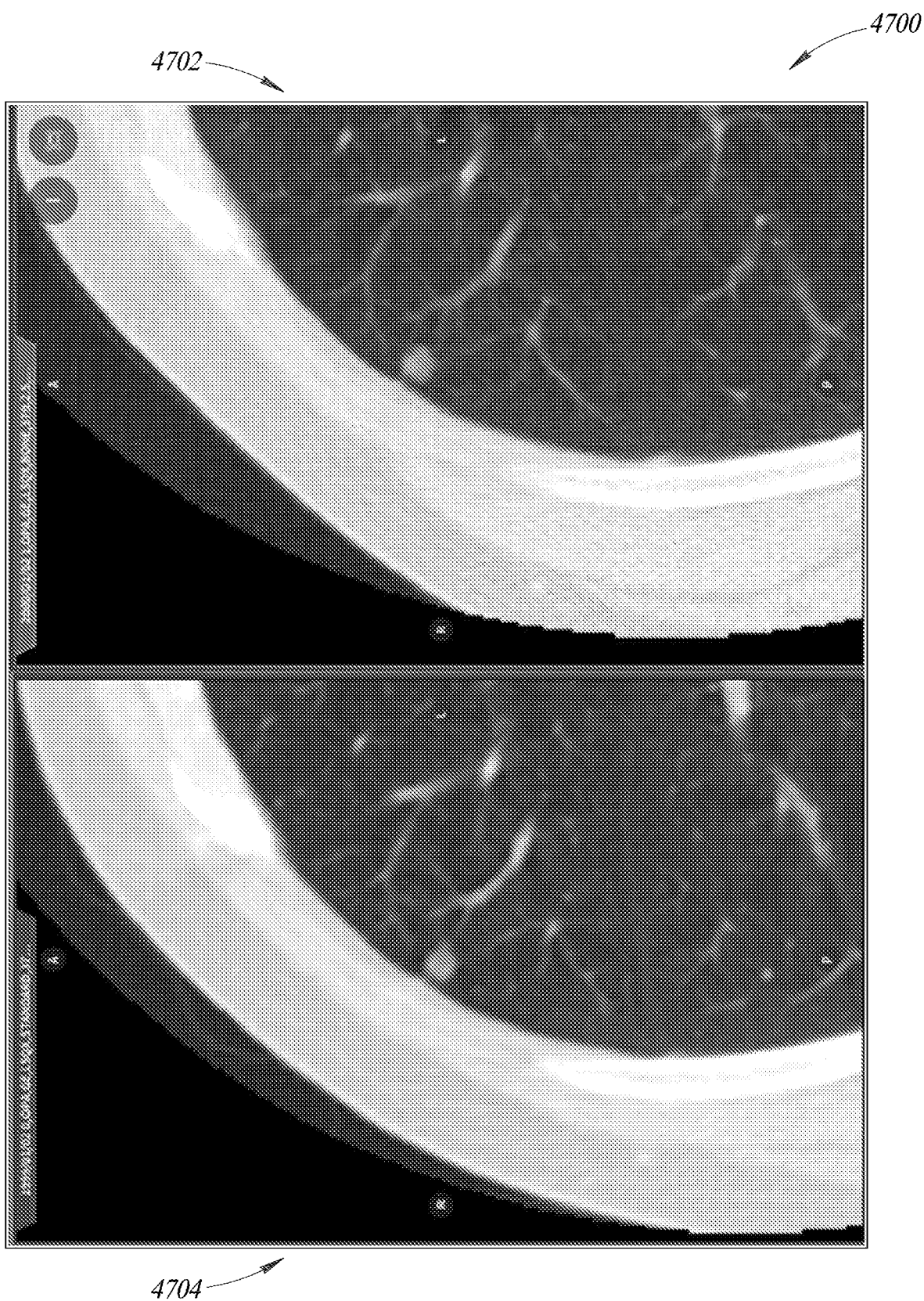
FIG. 47 is a screenshot of a user interface that shows two studies that are set up to show the same anatomy in scans taken at different times, according to one non-limiting illustrated implementation.

FIG. 47 shows a screenshot 4700 of an example GUI that allows for several lung CT studies to be displayed next to each other and be co-registered so that the same anatomy in the scans shows at the same time (e.g., 4702 and 4704). The image brightness and contrast may be automatically adjusted for optimal lung reading. Furthermore, this user interface can display several studies of this type at the same time in order to make it easy for the physician to compare images from the same patient over time. In both cases, the physician can scroll through studies, zoom, and move images to see the same anatomy in all of the different studies simultaneously. The system also offers manual and automated tools to level the brightness and contrast of the image based on the workflow selected.

Detection

The system is built to automatically detect and measure findings in the lung. These findings may comprise lung nodules, pneumothorax, fibrosis, COPD, measurements of surrounding organs or other incidental findings such as cardiac calcium levels and bone density. The detection of these different findings can apply a variety of thresholding, density or machine learning methods and the output of the findings may be editable by a user. The system also allows for manual detection of these findings. The software can also apply algorithms to detect key anatomical landmarks comprising vasculature, bronchi and lung segments.

Measurement and Quantification

The system can automatically measure the volume of the nodules that were detected either automatically or manually. From the volume of each nodule, the maximum diameter in the axial plane and its orthogonal diameter are mathematically calculated and reported. All of these measurements can be edited by the user. Furthermore, from the volume of each nodule, the density of the nodule can also be calculated and displayed in an editable fashion.

Figure 48:
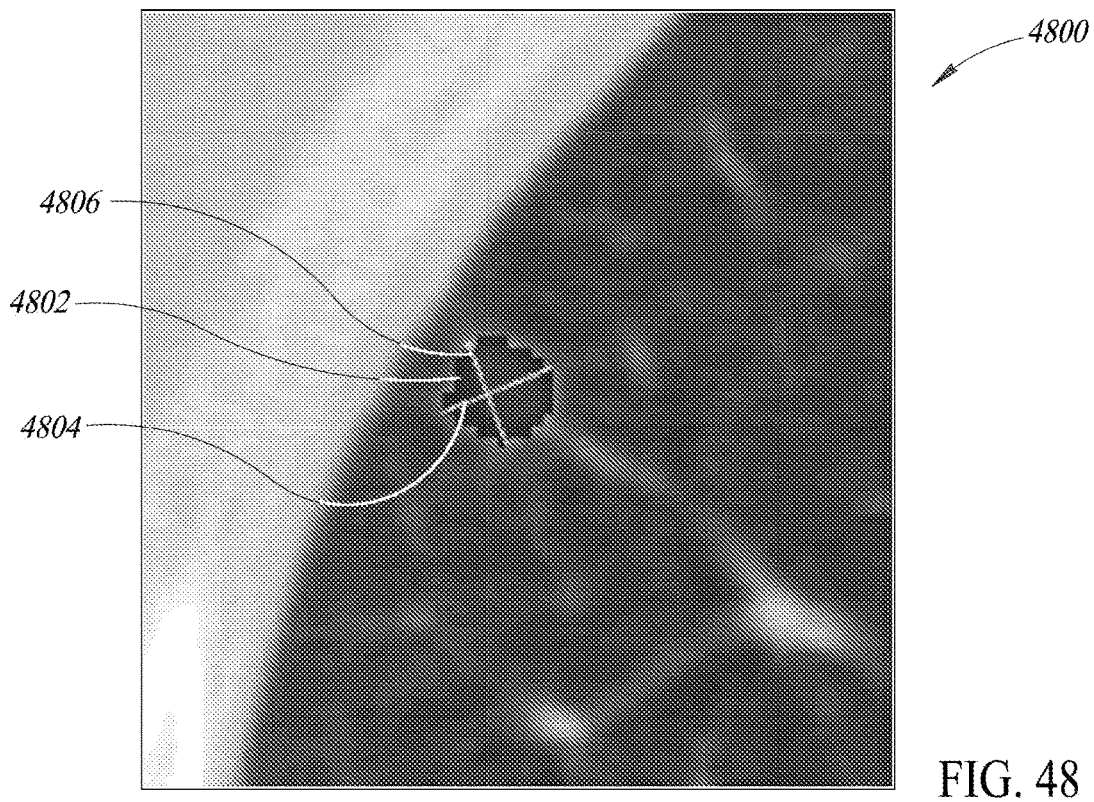
FIG. 48 is a screenshot of a user interface that shows the volume of a lesion and calculation of maximum linear dimension and maximum orthogonal dimension, according to one non-limiting illustrated implementation.

FIG. 48 shows a screenshot 4800 that depicts a lesion 4802, a maximum linear dimension 4804 of the lesion, and a maximum orthogonal dimension 4806 of the lesion.

Scoring

The system can automatically calculate different scores pertaining to lung nodules, comprising Lung-RADS, RECIST and Fleishman groupings, for example, from the measurements and quantification above. The system clearly shows each of the features, whether it was present or not present, and which Li-RADS score was selected. All of these annotations can be edited by the user, and the system automatically re-calculates the score and/or the features to ensure congruency.

The system may also allow clinicians to input each feature manually and it calculates the sores without automation.

Tracking

The system can track anatomical findings between scans of the same patient taken at different time points. Once two findings in scans are linked, these findings can also be used for image setup and layout.

Figure 49:
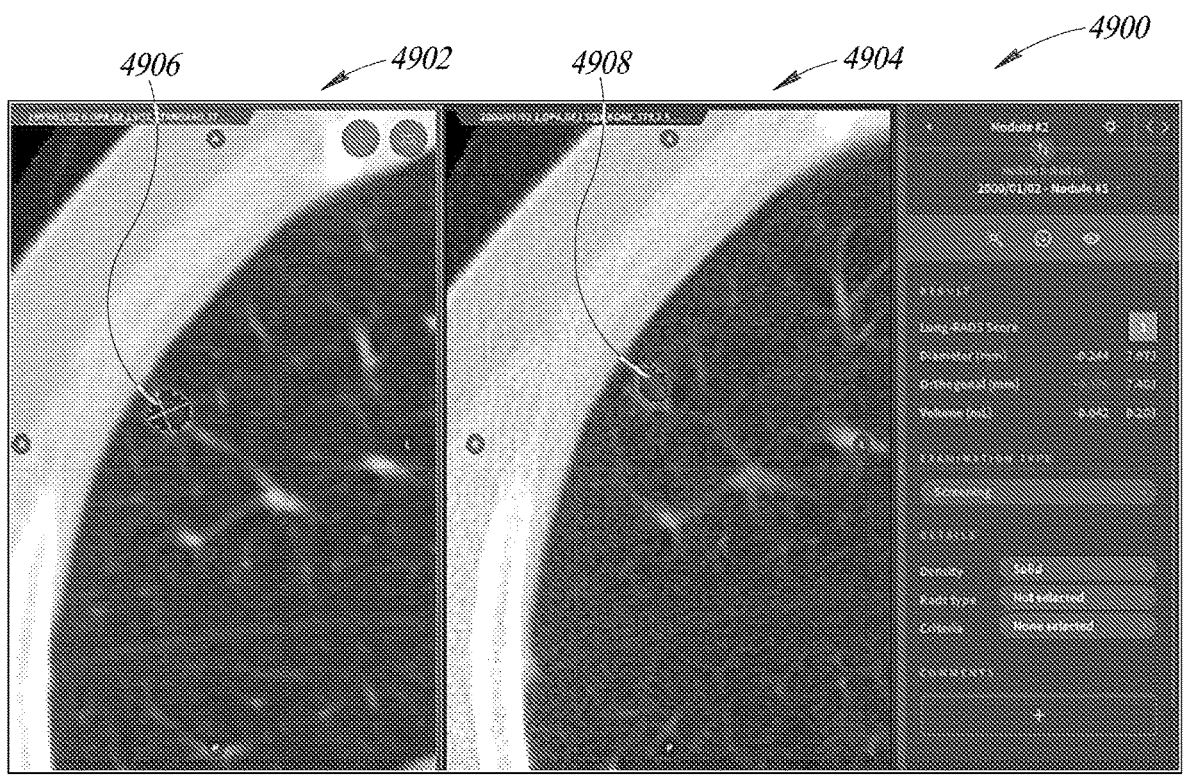
FIG. 49 is a screenshot of a user interface that shows linked findings between two scans, according to one non-limiting illustrated implementation.

FIG. 49 shows a screenshot 4900 of linked findings, in particular, a lesion 4906 in a left image 4902 and the lesion 4908 shown in the right image 4904.

A finding that was detected or confirmed by a physician may be referred to as a first finding, and a finding that was found by the system may be referred to as a second finding. The system can measure the second linked finding in the same way that the first finding was measured. Measurement may comprise linear dimensions, areas, volumes, and pixel density. These measurements are then compared mathematically to assess changes in size or presentation of the finding, and calculate growth or shrinkage of a finding over time.

Additionally, the system offers an interface that allows users to edit the linkages between findings, where linkages can be added between detected findings or where automated linkages can be broken. Once the linkages are edited, the software may re-calculate the measurements and their comparisons for each new pair of linked findings.

Reporting

The system can automatically report findings and their characterizations based on standard reporting templates and inputs created by both automated systems or users. The automatic report can be edited and supplemented by the user.

In one case, the report is created as a simple paragraph with text describing the findings. This can be done by populating fields in a paragraph with the findings, or via natural language processing (NLP) methods of creating text. The automatic report can be structured so that findings are presented based on urgency and severity. The automatic report can also be a graphical report containing tables and images that describe the evolution of the findings over time.

2nd Embodiment: Liver Augmented Workflow

GUI that comprises automated and manual tools for setting up, interpreting and reporting findings in abdominal MRI scan or an abdominal CT scan focused on hepatocellular carcinoma (HCC).

Setup

Figure 50:
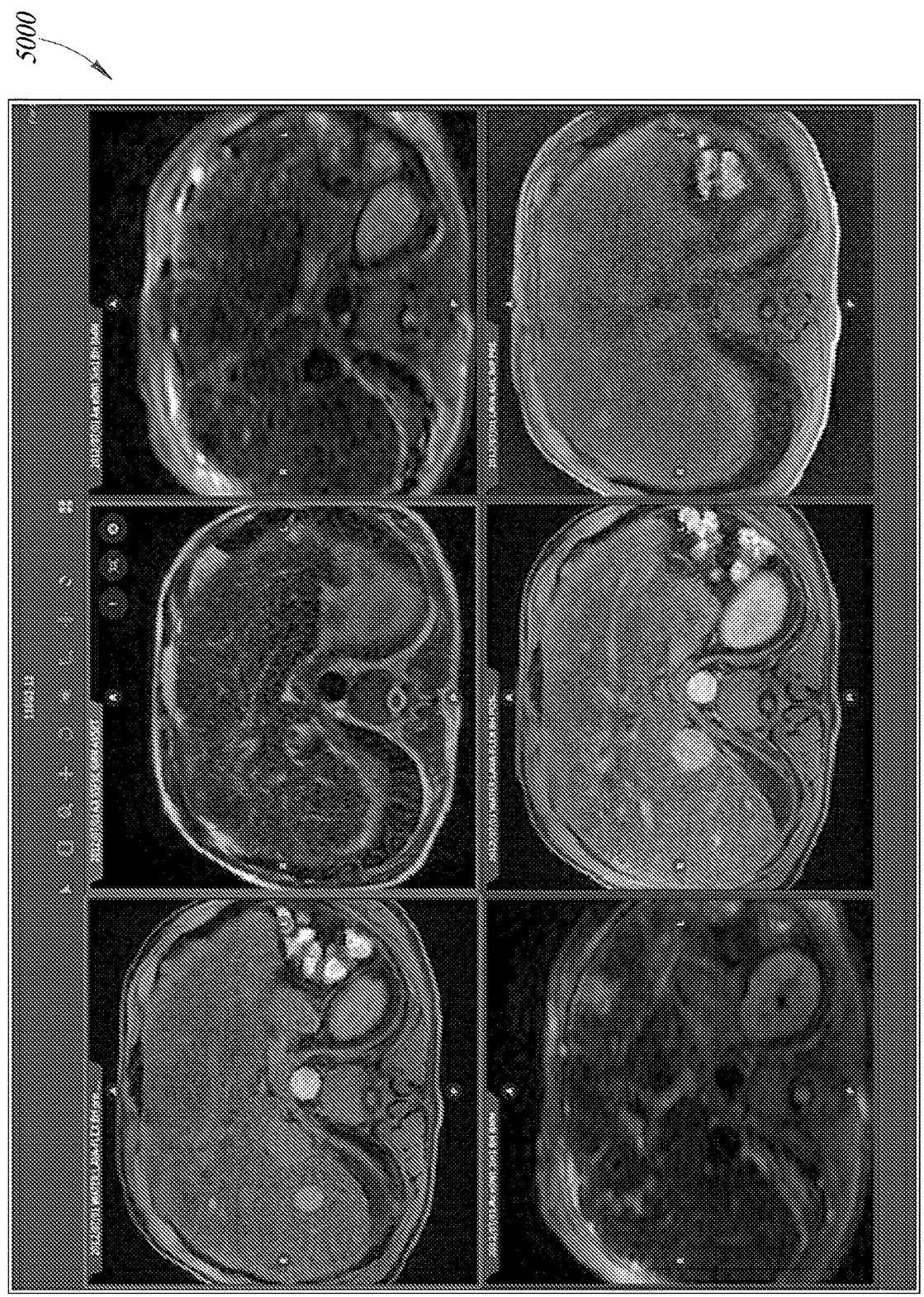
FIG. 50 is a screenshot of a user interface that provides an example of multiple series of a study that are aligned and shown simultaneously, according to one non-limiting illustrated implementation.

FIG. 50 is a screenshot 5000 of a GUI that allows for several liver series to be displayed next to each other and be co-registered so that the same anatomy in the scans shows at the same time. Which images go into the different canvases can be done automatically, or manually. In the case of the automatic setup, the series displayed will be those that inform LI-RADS scoring. Specifically, the scans could be acquisitions done prior during and after contrast injection. Then the images displayed comprise:

1. Prior to contrast entering the liver
2. As contrasts enters the liver
3. As contrast exits the liver
4. One or more scans after contrast has exited the liver Furthermore, this user interface can display several studies of this type at the same time in order to make it easy for the physician to compare images from the same patient over time. In both cases, the physician can scroll through studies, zoom, and move images to see the same anatomy in all the different studies simultaneously.

The system also offers manual and automated tools to level the brightness and contrast of the image based on the workflow selected.

Detection

The system is built to automatically detect and measure findings in the liver. These findings comprise liver lesions, fat content, fibrosis, measurements of surrounding organs and other incidental findings. The detection of these different findings can apply a variety of thresholding, density or machine learning methods, and the output of the findings is editable by a user. The system also allows for manual detection of these findings. The system can also detect key liver landmarks comprising vasculature and liver segments.

Measurement

The system can automatically measure the volume of the liver, as well as the volume of the lesions that were detected either automatically or manually. From the volume of each lesion, the maximum diameter in the axial plane and its orthogonal are mathematically calculated and reported. All of these measurements can be edited by the user.

Figure 51:
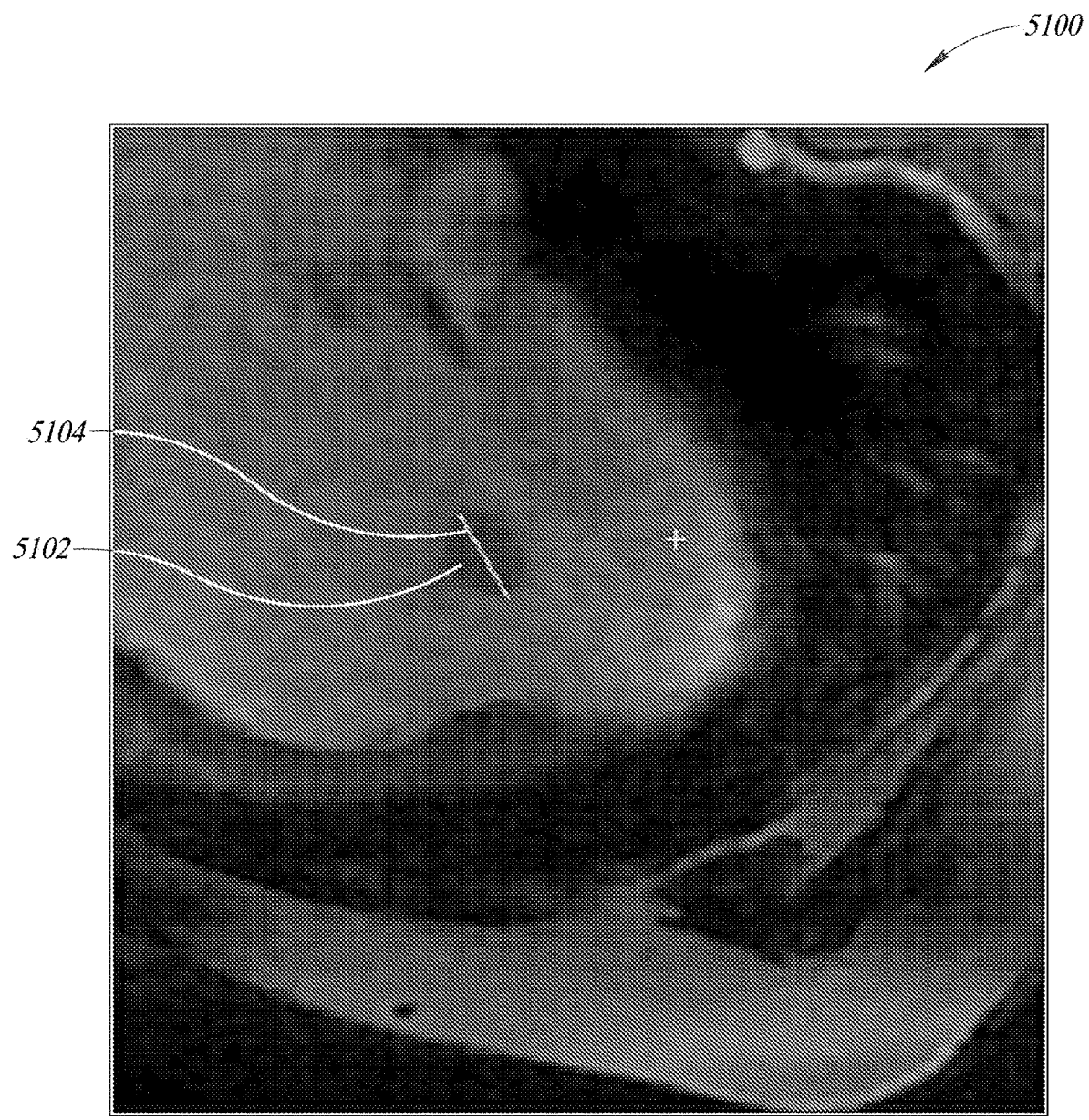
FIG. 51 is a screenshot of a user interface that shows segmentation of a liver and calculation of the longest linear diameter, according to one non-limiting illustrated implementation.

As an example, FIG. 51 shows a screenshot 5100 of segmentation of the liver and calculation of the longest linear diameter 5104 of a lesion 5102. Other measurements the system can capture comprise of liver fat content, fibrosis and texture, as well as measurements of surrounding organs and tissues.

Annotation and Scoring

The system can automatically define features of liver lesions in the different series, comprising enhancement, washout, and corona presence, and then calculates the corresponding LI-RADS score. The system clearly shows each of the features, whether it was present or not present, and which LI-RADS score was selected. All of these annotations can be edited by the user, and the system automatically re-calculates the score and/or the features to ensure congruency.

The system also allows clinicians to input each feature manually and it calculates the LI-RADS score without automation. Alternatively, the user can select the score directly from the score table and fill in only the necessary number of features. These features are illustrated in a GUI 5200 shown in FIG. 52.

Tracking

The system can track anatomical findings between series of the same patient taken at different time points. Once two findings in scans are linked, these findings can also be used for image setup and layout.

A finding that was detected or confirmed by a physician may be referred to as a first finding, and a finding that was found by the system may be referred to as a second finding. The system can measure the second linked finding in the same way that the first finding was measured. Measurement may comprise linear dimensions, areas, volumes, and pixel density. These measurements are then compared mathematically to assess changes in size or presentation of the finding, and calculate growth or shrinkage of a finding over time.

Additionally, the system offers an interface that allows users to edit the linkages between findings, where linkages can be added between detected findings or where automated linkages can be broken. Once the linkages are edited, the software may re-calculate the measurements and their comparisons for each new pair of linked findings.

Reporting

The system can automatically report findings and their characterizations based on standard reporting templates and inputs created by both automated systems or users. The automatic report can be edited and supplemented by the user.

Figure 53:
FIG. 53 is a screenshot of a user interface that includes an excerpt of an automated report that collects all characteristics of each finding, according to one non-limiting illustrated implementation.

In one case, the report is created as a simple paragraph with text describing the findings. This can be done by populating fields in a paragraph with the findings, or via NLP methods of creating text. The automatic report can be structured so that findings are presented based on urgency and severity. The automatic report can also be a graphical report containing tables and images that describe the evolution of the findings over time. FIG. 53 is a GUI 5300 that shows an excerpt of an automated report that collects all characteristics of each finding.

E. AUTOMATED THREE DIMENSIONAL LESION SEGMENTATION

Identification of regions of interest in image data can occur either manually or with the help of semi- or fully-automated software. Use of semi- or fully-automated software for finding possibly malignant regions of interest (lesions) represented in a scan is commonly referred to as computer aided detection (CAD or CADe).

The lesions in both lung and liver scans require further analysis and study, both qualitatively and quantitatively. Qualitative assessments include the texture, shape, brightness relative to other tissue, and change in brightness over time in cases where contrast is injected into the patient and a time series of scans are available. Quantitative measurements commonly include the number of possibly malignant lesions, longest linear dimension of the lesions, the volume of the lesions, and the changes to these quantities between scans. It is also possible to quantitatively assess texture, shape, and brightness with specialized software.

Careful manual quantitative assessment of lesions is tedious and time consuming; the help of semi- or fully-automated software can help expedite the process.

Limitations of Manual Quantification of Lesions

Manual quantification of important characteristics of lesions can take minutes per lesion. For example, quantifying volume manually in most software requires drawing 2D contours surrounding the lesion on every slice that intersects the lesion; for larger lesions, this may mean drawing contours on 15+ slices. Quantifying features about the lesion, such as the shape, margin, opacity, heterogeneity, location within the body, relationship to surrounding lesions, and tissue properties surrounding the lesion also take significant clinician time.

Limitations of On-Demand Quantification of Lesions

Machine learning models allow for automatic measurement of many quantities of interest. However, accurate machine learning models, such as those based on convolutional neural networks (CNNs), can be slow to run and expensive to have ready at a moment's notice for on-demand inference. Models that are more computationally efficient than CNNs exist, but those algorithms tend to have significantly poorer accuracy than CNNs. See, e.g., Russakovsky, Olga, et al. "Imagenet large scale visual recognition challenge." International Journal of Computer Vision 115.3 (2015): 211-252.

Limitations of CAD-Based Lesion Detection and Segmentation

Computer aided detection (CAD) can be used to both detect and segment potentially cancerous lesions. With such a system, a clinician invokes the CAD algorithm and lesions are detected and shown to the clinician, possibly along with their segmentations. One major disadvantage of this system is that clinicians may grow accustomed to the detection technology and come to rely on it, causing degradation of their own skills. Evaluation of the CAD systems therefore often requires onerous clinical trials to prove accuracy and efficacy, making them particularly expensive to develop. A system that automatically detects and segments lesions without degrading clinician skills or requiring such a burden of proof of accuracy would have significant advantages over a full CAD system.

1st Embodiment

Overview

Figure 54:
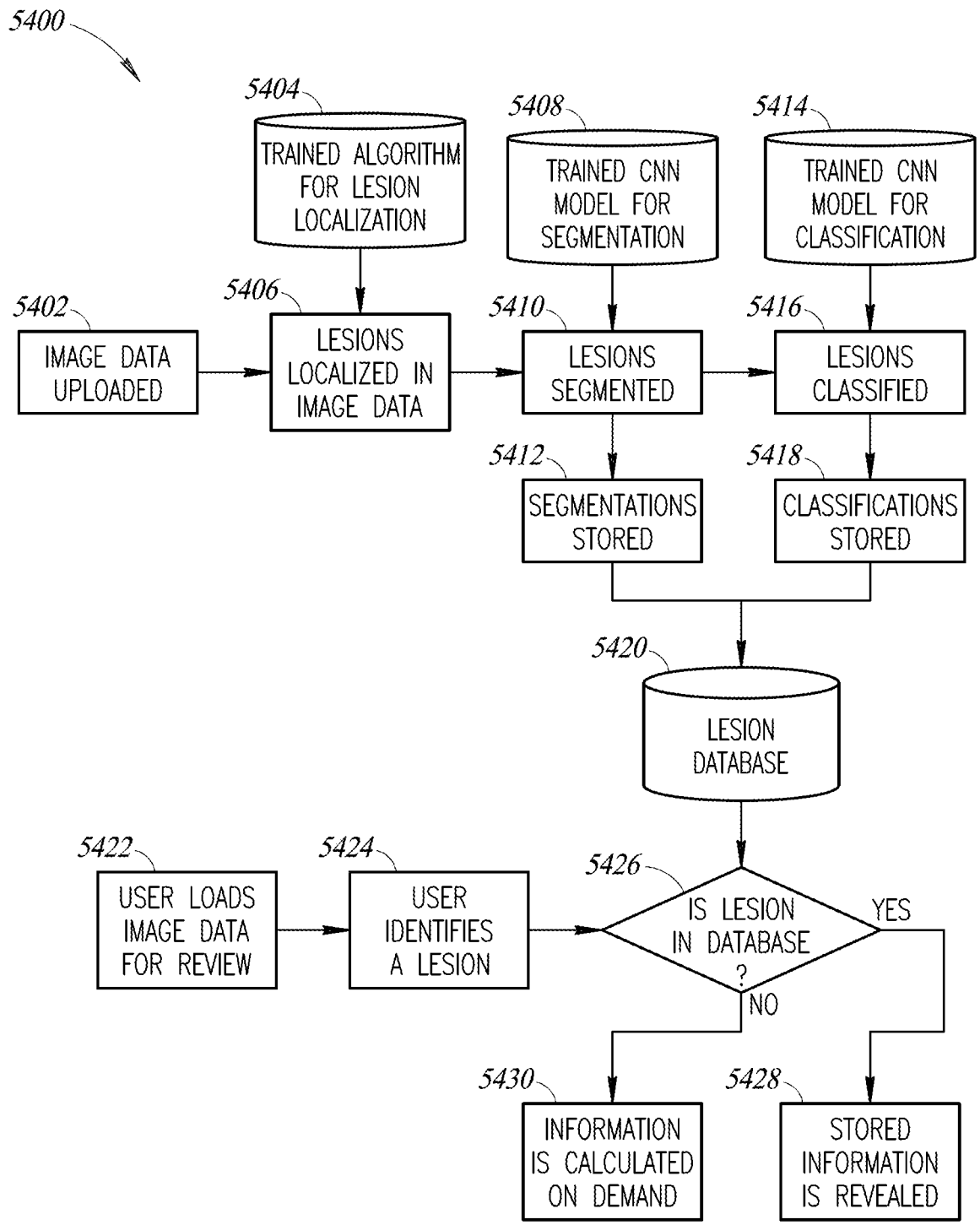
FIG. 54 is a flow diagram of a method of operating a computer-based system to perform automated three-dimensional lesion segmentation, according to one non-limiting illustrated implementation.

FIG. 54 is a flow diagram of a process 5400 of operating a processor-based system to store information about a pre-localized region of interest in image data and to reveal such information upon user interaction, according to one illustrated implementation. The process 5400 begins at 5402 when image data is uploaded to a processor-based system. A pre-trained algorithm for lesion localization stored in a database at 5404 is used to localize lesions in the image data at 5406. This pre-trained algorithm may include one or more machine learning algorithms, such as, but not limited to, Convolutional Neural Networks (CNNs). In at least one implementation of the current disclosure, two unique CNNs are joined end to end; the first CNN proposes locations of potential lesions with a focus on high sensitivity, and the second CNN sorts through these proposed lesions and discards results determined to be false positives.

A pre-trained CNN model for segmentation of lesions at 5408 is used to segment the lesions at 5410. This CNN model evaluates image patches centered on the localized lesion locations 5406 and calculates the segmentation of the lesion represented in the image data. In at least one implementation, this CNN model 5408 is trained and evaluated on image/segmentation pairs in an end-to-end fashion in 3D such that for every 3D input of image data, a 3D segmentation is produced. In other implementations, the segmentation model operates on individual 2D slices of the 3D lesion. In at least one implementation, the image data are resampled to have isotropic world spacing along each pixel dimension; other implementations do not resample the image data.

The segmentations are stored at 5412 in a database at 5420. These segmentations may be stored as serialized Boolean arrays, but other lossless means of storing the data, such as, but not limited to, Hierarchical Data Format (HDF) files and lossless-specific Joint Photographic Experts Group (JPEG) files, may also be used. In at least one implementation, the Boolean arrays are stored with a key that is a concatenation of the series unique identifier and lesion world center location in x, y, and z, but other keys, such as those that utilize the study unique identifier or lesion position in pixel space, may also be used.

In at least one implementation, a pre-trained CNN model for classification of lesions at 5414 is used to classify lesions at 5416. This CNN model evaluates image patches centered on the proposed location at 5406 and infers metadata about the lesion in question. This metadata can include, but is not limited to, the features of the lesion, including one or more of size, shape, margin, opacity, or heterogeneity, the location of the lesion within the body, the relationship to surrounding lesions and tissue properties surrounding the lesion, the malignancy, or the cancerous subtype of the lesion. The CNN model optionally uses the segmentation generated by the CNN model at 5410 and stored at 5412 to help the classifications.

The classifications are stored at 5418 in a database at 5420. In at least one implementation, the metadata arrays are stored with a key that is a concatenation of the series unique identifier and lesion world center location in x, y, and z, but other keys, such as those that also utilize the study unique identifier or lesion position in pixel space, may also be used.

The user loads image data for review at 5422 to look for lesions. Doctors often look for lesions by slice-scrolling through axial slices of the image data, but reading the scan in a coronal or sagittal reformat is not uncommon. After visual identification of the lesion, the user identifies the lesion to the software at 5424. The identification of the lesion can occur via means including, but not limited to, a click or tap within the pre-generated segmentation mask, a mouseover of the pre-generated segmentation mask, or a click-and-drag selection surrounding all or part of the pre-generated segmentation mask.

The presence of the lesion is the database is assessed at 5426; in at least some implementations, the lesions' presence is assessed by checking whether the lesion unique identifier is present as a key in the database. If the lesion is determined to be present in the database, all stored information, including but not limited to the segmentation and classifications of the lesion, are revealed. In at least some implementations, if the lesion is determined to not be present in the database at 5426, information including one or more of the segmentation and classifications is calculated on demand using the trained CNN models at 5408 and 5414.

In at least some implementations, multiple related series of image data may be available. Those series may have been acquired in a single imaging session, they may be acquired across multiple imaging sessions (e.g., separated by hours, days or years), or some combination of the two. If the images were acquired in a single imaging session, they may be, for example, images taken of the same anatomy with using different MRI pulse sequences or CT doses, images taken of the same anatomy over the course of a contrast perfusion study, or images taken of different, nearby anatomical sections. When multiple series are available, the user may be interested in having information revealed for the same lesion on multiple series, or on the optimal series, where the optimal series may or may not be the series with which the user chooses to interact. The notion of optimality is task dependent, and may take on different definitions, including, but not limited to: the series of highest quality; the series with fewest artifacts; the series on which the lesion can most accurately be assessed; the series for which clinical guidelines or other standards recommend assessing the lesion; the series that has been acquired most recently; the series that has been acquired least recently; or any combination of the above.

In at least some implementations, under the circumstances described above, or under similar circumstances, the indication of a lesion by the user in one series may reveal stored information in one or more series, possibly including the series in which the user indicated the lesion.

F. AUTONOMOUS DETECTION OF MEDICAL STUDY TYPES

A Method of Auto-Triaging Medical Data for Machine Learning Analysis

In healthcare, massive amounts of data are being generated every second. At a healthcare facility, all of this data is typically stored in separate repositories and not leveraged holistically to improve patient care. The method described herein auto-triages disparate data streams (e.g., EMR data, imaging data, genotype data, phenotype data, etc.) and sends the data to the right algorithms and/or endpoints for processing and/or analysis. Since there are so many algorithms that are specific to an application and/or organ, not all of these algorithms can be executed on all of the data being generated within a healthcare system; this would be too costly and results would take too long to generate. Sometimes results need to be ready immediately since every second counts (for example for stroke patients). It can take up to 10 minutes to run a machine learning (ML) algorithm on one study. If there are several ML algorithms, the time and cost to try every combination may not be clinically feasible.

Figure 55:
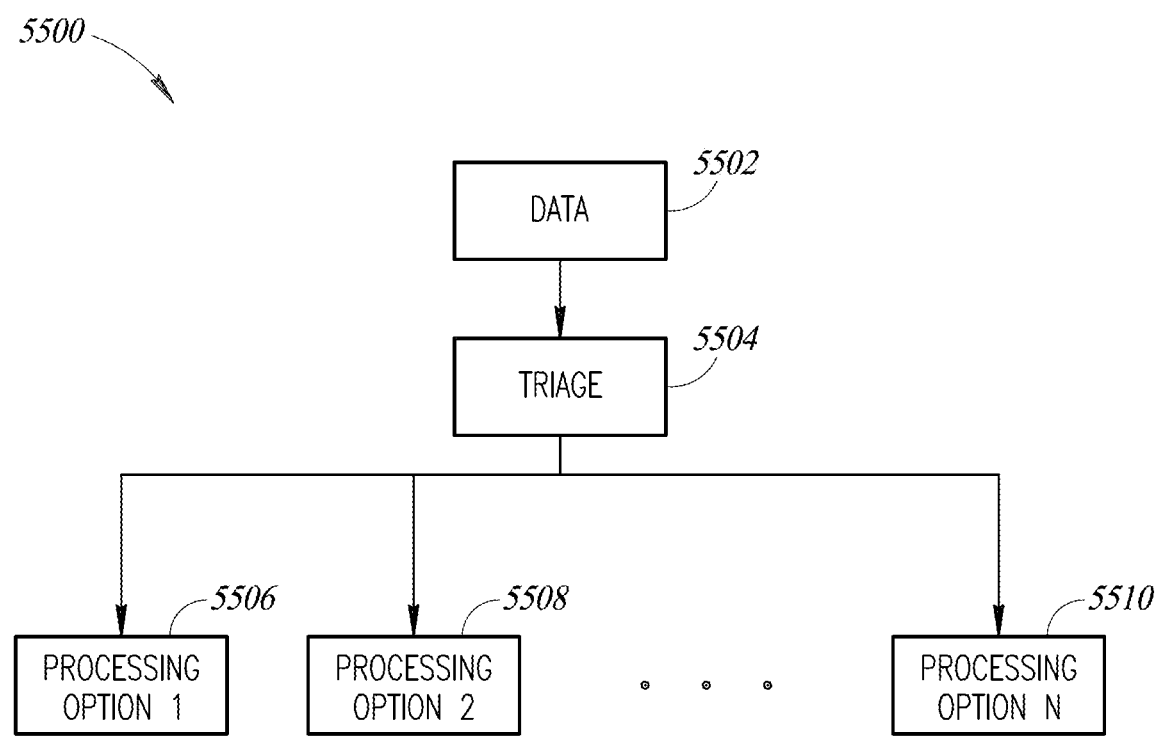
FIG. 55 is a flow diagram that depicts a high level overview of a method of operating a computer-based system to perform automated three-dimensional lesion segmentation, according to one non-limiting illustrated implementation.

FIG. 55 shows a high-level method 5500 of at least one implementation of the system. Data 5502 is sent to a triage system 5504. The triage system 5504 analyzes the data 5502, and based on its content, invokes one or more of N appropriate processes, 5506, 5508, 5510. In order to auto-triage data, diagnostic and/or non-diagnostic data may be used as input into an algorithm (referred to herein as the "auto-triager") executable on the system. In at least one implementation, the output of the auto-triager is a set of locations/destinations for the incoming diagnostic and/or non-diagnostic data. The locations/destinations could be another algorithm, a repository, or a tag associated with the data, for example.

Specifically, in imaging, DICOM is the standard used to transmit and store medical images. In at least some implementations, based on the DICOM headers for a given study, the auto-triager determines what body part/organ or specialty the data is relevant for (e.g., cardiac, neuro, thoracic, abdominal, pelvic, etc.). At least some implementations determine the imaging modality (e.g. MR, CT, PET, etc.) of the study. After determining the relevant information about the study, in at least some implementations, the auto-triager lets the next processing step in the process know that a subset and/or all of the potential processing algorithms are required to analyze a study. In at least some implementations, the auto-triager can be used to do any of: facilitate loading of the appropriate workflow when the user opens the study; or determine which machine learning model(s), if any, to run on series within the study.

In the case of a medical imaging platform that has two or more applications (or modules or machine learning algorithms), it is helpful for a reproducible imaging pipeline to be established to ensure the right data is being processed at the right time using the right machine learning algorithms. Typical medical imaging datasets have the following hierarchy, where each item in the list contains one or more instances of subsequent items in the list: patient, study, series, instance.

With this hierarchy, typically there is one or more studies per patient, one or more series per study, and one or more instance or image per series. With all of this data, it is very important to ensure that the right data is processed using the correct algorithm. There may be two types of image processing pipelines, 1) Offline or Batch and 2) Interactive.

An offline or batch imaging pipeline may include one or more of the following acts:
1. Raw image created by scanner (e.g. modality).
2. Raw image converted to bitmap image using some sort of reconstruction technique.
3. Bitmap image sent to an algorithm for processing. Processing may include producing a text and/or image report.
4. Report sent to people (e.g., clinicians, patients, etc.) and/or archiving (e.g., EMR, PACS, RIS, etc.).

An interactive imaging pipeline may include one or more of the following acts:
1. Raw image created by scanner (e.g. modality).
2. Raw image converted to bitmap image using some sort of reconstruction technique.
3. Bitmap image sent to a visualizer (e.g., PACS, advanced visualization software, workstation, cloud based software etc.).
4. Optional: Visualizer receives data and optionally attempts to process this data (e.g., to automate the interpretation and reading, or to speed loading).
5. User loads data (e.g. study, image, etc.) using a user selected application (also referred to as a workflow or module).
6. User clicks to do something manually and/or tells the system to do something automatically by explicitly telling it what to do (e.g., compute volume of heart)
7. Optional: user opens study, validates and optionally adds more content, creates report
8. Report sent to people (e.g., clinicians, patients, etc.) and/or archiving (e.g., EMR, PACS, RIS, etc.).

For the processing acts of either interactive mode or batch mode processing, it is important that the correct processing is performed on the right set of data. Processing may include format optimization (e.g., for computing analytics, such as derivatives), storage optimization, loading optimization, rendering optimization, computing heuristics (e.g., average window width/window level), as well as performing machine learning to automate the task of interpreting a study. Many of these processing techniques may be generic (e.g., applied to all studies independent of modality, organ, patient), and thus there may be no need to differentiate studies. But machine learning, on the other hand, can be quite expensive and may be very specific to the type of modality, organ, patient demographic, etc.

Many implementations of the auto-triaging algorithm are possible. Below is a description of several non-limiting example implementations in the case of medical imaging data. The various implementations may be combined in any suitable manner to provide further implementations.

A first implementation is an auto-triager based on using the either public and/or private DICOM tags. The algorithm uses DICOM tags (e.g., the default DICOM tags) to route to a machine learning algorithm. For example, if modality for a study is "MRI" and body part is "Heart", the algorithm routes this study to a heart MRI machine learning algorithm and/or a heart visualizer, for example.

A second implementation is an auto-triager that uses both the pixel data and/or DICOM tags. This method uses heuristics in the pixel data to try to detect what is in the image. An example of this is a 3D face detector. If a face is detected, then the study is most probably a head scan. The auto-triager may then route this study to a neuro machine learning algorithm and/or a neuro visualizer, for example.

A third implementation is an auto-triager that triages the incoming data based on custom rules, optionally combined with any of the methods described herein. Each institution may use custom routing rules to send data to the correct location. This method uses data transfer information, such as Application Entity (AE) title, host, port, IP address, etc., to route data based on custom rules per organization.

A fourth implementation is an auto-triager that triages data using machine learning and/or deep learning. The machine learning algorithm may be trained on an annotated dataset of images. The annotations may include a label of body part, specialty, workflow, and/or additional diagnostic information contained in the data. Once the machine learning/deep learning model is created, that model may be used to run inference on any new incoming unannotated data.

Optionally, once a study has been triaged (e.g., the organ(s), modality, and/or the correct application is selected), additional analysis, which may include dedicated machine learning algorithms, of the series and images within that study may be performed using heuristics based on many features of the study, including but not limited to the following: tags within the DICOM data (e.g. FrameOfReferenceUID); same slice spacing; same number of images; a set of rules per sequence (e.g., ProtocolName or private DICOM tags); or any combination of the above

G. PATIENT OUTCOMES PREDICTION SYSTEM

Terms

CNN—Convolutional Neural Network
CT—Computed Tomography
Database—Any nontransitory processor-readable storage medium, including but not limited to a relational database (e.g., MySQL), a "NoSQL" database (e.g., MongoDB), a key-value store (e.g., LMDB), or any centralized or distributed file system
Epoch—Date from which predictions are made; for example, whether a patient will suffer "cancer associated death within the next 365 days," the epoch is the date on which that prediction is made and when the countdown to 365 days begins.

Once a diagnosis of cancer is confirmed for a patient, such as through histopathological or molecular analysis of biopsy specimens, it is critical to determine the most appropriate treatment for the patient. Treatment decisions are traditionally made by oncologists, with additional insight provided on a case-by-case basis by radiologists, surgeons and radiation oncologists. One big challenge for this system is the lack of conveniently availability historical information about similar patients, treatments they received, and their clinical outcomes. Clinicians rely on their memory of similar cases and on papers from medical journals to determine their treatment decisions but these sources of information are generally incomplete and subject to biases. Treatment decisions are particularly ambiguous for late stage cancer patients, due to the many different ways that cancer can spread and the varying ability for individual patients to handle aggressive treatments.

Clinicians would greatly benefit from a system that can provide, on demand, treatment guidance that draws on a large, objective database of patients with similar cancers, the treatments they received, and the resulting outcomes. Such a system could be used to compare different treatments and their likely outcomes for the given patient in order to choose the best treatment for the given patient.

Such a treatment planning system has traditionally been challenging to create due to the heterogeneity of electronic medical records and the lack of sophisticated models that can extract relevant features from image data. However, the availability of large, well-curated, longitudinal data sets, such as the National Lung Screening Trial [NLST 2011], as well as the advent of modern convolutional neural networks [Russakovsky 2015] that can be used for image feature extraction now allows these challenges to be overcome.

System Overview

One implementation of the full system for predicting patient outcomes is described below in two separate phases: the "training" phase, in which the models and databases that will be used in operation of the system are developed and the "inference" phase, in which a user interacts with the system to retrieve predicted outcomes for a patient.

Figure 56:
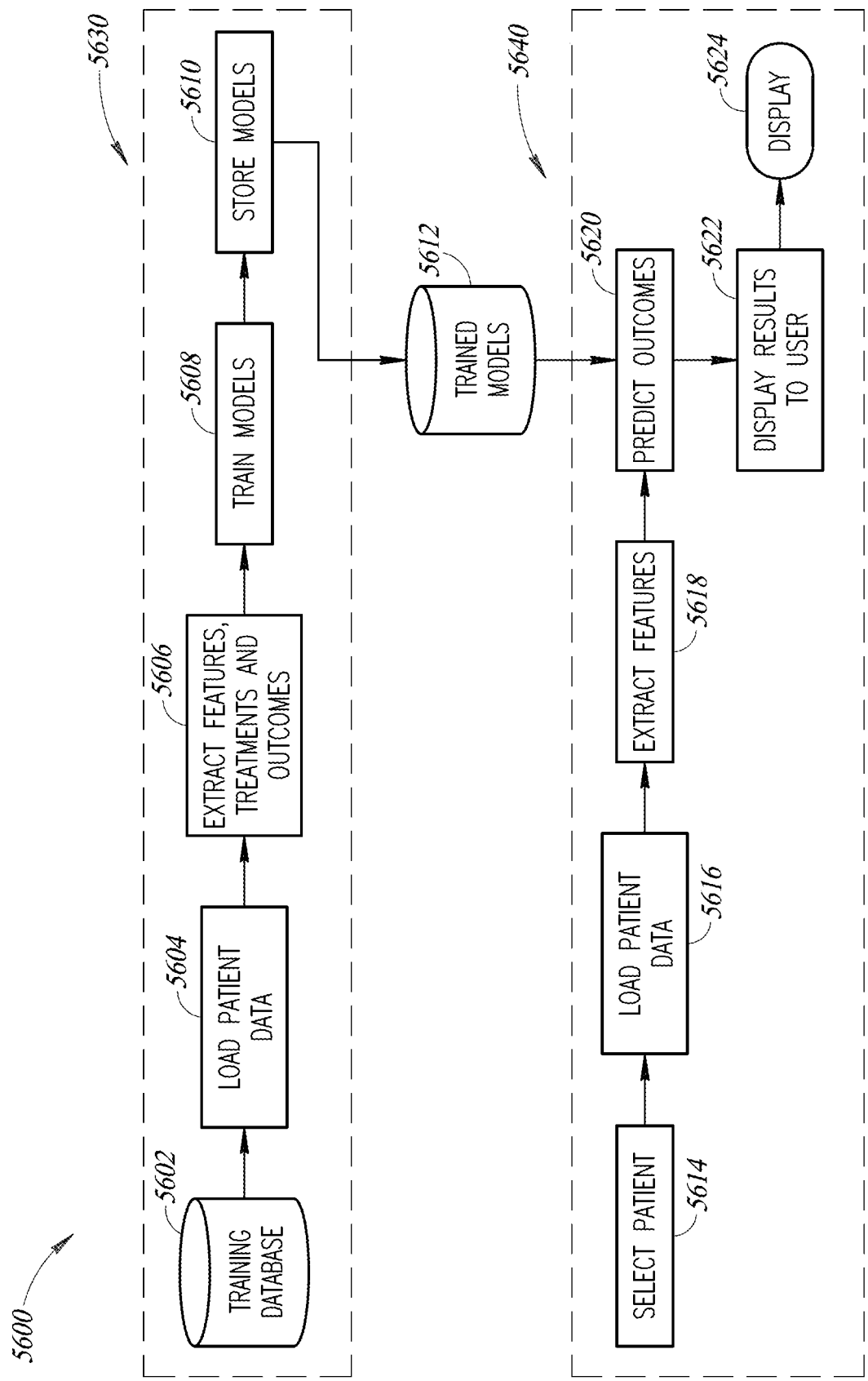
FIG. 56 is a high level flow diagram of a patient outcomes prediction system, according to one non-limiting illustrated implementation.

FIG. 56 shows one implementation of a system 5600, including both a training phase 5630 and an inference 5640 phase. In the training phase 5630 of this implementation, training data is stored in a training database 5602. This training data is derived from patients with known or suspected diagnosis of cancer and for whom clinical outcomes are known.

Training data is loaded at 5604 from the database 5602 and features, treatments, features and outcomes are extracted at 5606. Features and treatments are used as inputs to the machine learning models and outcomes are used as labels or targets for the models. One or more machine learning models are trained at 5608 and subsequently stored at 5610 to a database 5612 of trained models. More details of some implementations of training are described below.

In the inference phase 5640 of this implementation, initially a patient is selected for whom inference is to be performed at 5614. Patient data is loaded for the selected patient at 5616 and features are extracted at 5618 in the same manner as they were extracted during training at 5606. Inference is performed with the trained machine learning models 5612 and input features 5618 to predict outcomes for the patient under one or more different treatment scenarios 5620. The results of inference are then displayed to the user 5622 on a display 5624. More details of some implementations of inference are described below.

Training

Figure 57:
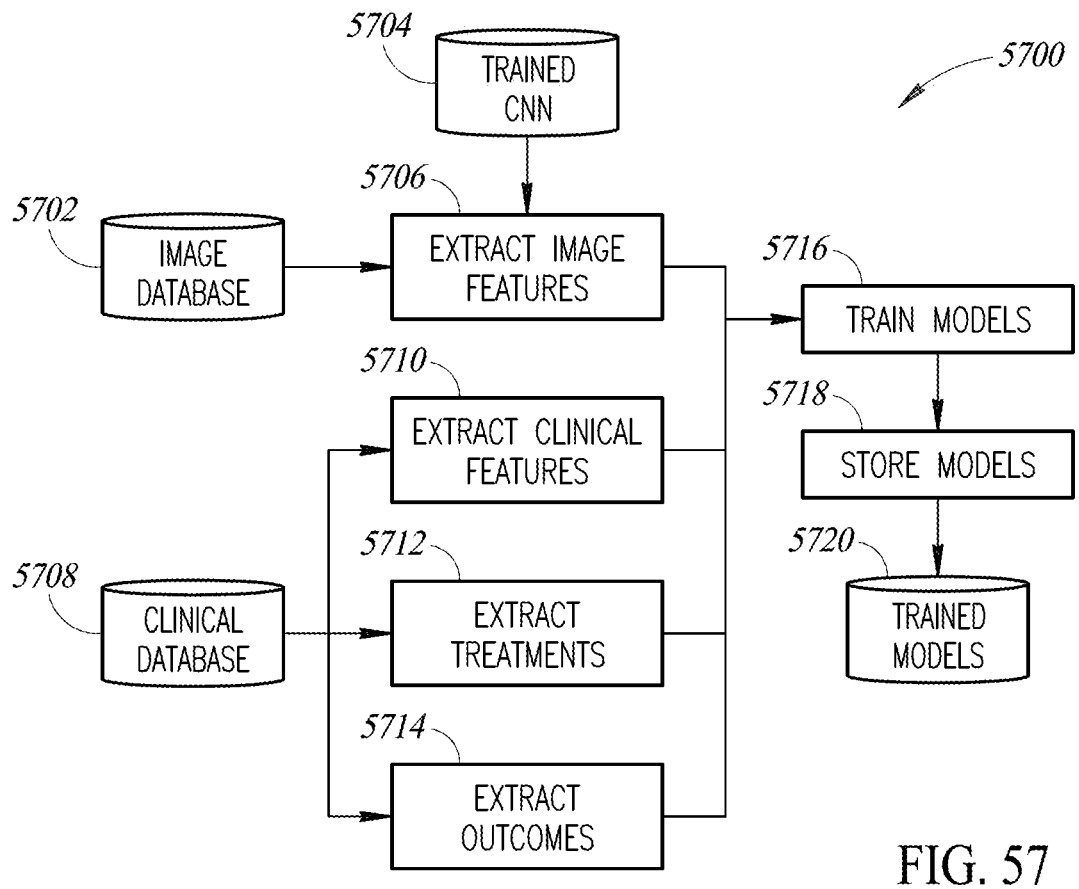
FIG. 57 is a flow diagram of a method training models in a patient outcomes prediction system, according to one non-limiting illustrated implementation.

FIG. 57 shows a method 5700 according to one implementation of the training phase 5630 of the system 5600. In at least some implementations, images from patients are loaded from an image database 5702 and a trained convolutional neural network (CNN) 5704 is used to extract image features at 5706. Images from the image database 5702 are associated with patients with a known or potential diagnosis of cancer. The images may have been acquired either before or after a cancer diagnosis was made or suspected; e.g., images acquired a year prior to a cancer diagnosis or a year after a cancer diagnosis may be used in order to analyze longitudinal changes and the rate of growth of suspected cancerous lesions.

The CNN used for feature extraction may be any of a variety of forms of CNN, including but not limited to: a classification network; an object detection network; a semantic segmentation network; or any combination of the above.

For implementations for which the trained CNN is a classification network, the CNN may have been trained to predict one or more of a variety of different objectives from patient medical images, including but not limited to: features of potentially cancerous lesions, e.g., size, shape, spiculations; features of the surrounding organ, e.g., texture, other (possibly non-cancer) disease; lesion malignancy; changes to any of the above metrics over time, using images acquired over time (e.g., over the course of days, months or years); image provenance, such as whether the image is from a true radiological exam or whether it is from a system that generates fabricated images; or any combination of the above.

CNNs are typically composed of many (e.g., significantly more than two) layers; some recent networks have 1000 or more layers [He 2016]. The input to the first layer is typically the overall network input (e.g., an image of a lesion that may or not be malignant) and the output of the final layer is typically the metric of interest (e.g., the scalar probability that the lesion is malignant). Intermediate layers are typically considered "hidden" and are used only for internal network calculations. However, the outputs of these intermediate layers contain a representation of the input that is relevant for quantifying its properties (e.g., malignancy), so it is reasonable to think of the outputs of intermediate layers as relevant "features" of the lesion; hence, these outputs are often called "feature maps." These feature maps can be used as features to help predict objectives for which the model was not explicitly trained.

In at least some implementations, the feature extraction act 5706 involves performing a forward pass through the CNN and extracting features from the outputs of intermediate CNN layers. The final output of the CNN (e.g., the probability of malignancy) can also be used as features, either in lieu of or alongside features from intermediate layers. Some types of classification CNNs (e.g., models that predict the lesion subtype) may have multiple final outputs, any or all of which may be used as features.

In at least some implementations, data from a clinical database 5708 is used in the training process. From the clinical database, clinical features 5710, treatments 5712 and outcomes 5714 are extracted. Many different clinical features 5710 can be used, including but not limited to: patient demographic information (e.g., age, sex, race, ethnicity, weight or height); patient's current and past medical history and conditions (e.g., previous diseases, previous cancers, hospitalizations, treatments, procedures, alcohol, tobacco or drug use, exposure to carcinogenic substances, comorbidities); family medical history; diagnostic information relating to the current known or potential cancer (e.g., cancer stage, grade or subtype, lesion size, molecular expression data, molecular sequencing data, information about metastases, location in the body, relationship to other structures within the body); or any combination of the above.

Many different treatments 5712 can be used. Treatments used will be those that are relevant for the particular form of cancer for which the system is designed. At least one implementation of this system is designed to predict outcomes for lung cancer patients, in which case, treatments may include without being limited to: chemotherapy (possibly including the specific drugs, session duration and interval, etc.); lymphadenectomy; lobectomy; radiation (possibly including the specific site, dose, session duration and interval, etc.); resection; pneumonectomy; or any combination of the above.

For cancers other than lung cancer, analogous treatments for the appropriate cancer site may be included.

Many different outcomes 5714 can be used as the model's predictive target, including but not limited to: cancer-associated death; death from any cause; disease-free survival; time until next cancer-related hospital admission; time until next hospital admission from any cause; pathological complete response after treatment; post-treatment recovery time; or any combination of the above.

For outcomes that are events, the outcome may take on any of several forms, including but not limited to: the binary occurrence of the event in some fixed number of days from the epoch (where the epoch is the date on which the prediction is made); the expected number of days before the event occurs; given a definition of several populations with different distributions of when the event may occur (e.g., with different Kaplan-Meier survival curves): the population in which the given patient is most likely to belong; or any combination of the above.

For example, if the outcome is "whether the patient dies as a result of cancer in the next 365 days," then the prediction could be either True or False, or it could be a probability of the event occurring from 0 to 1. Alternatively, if the outcome is "when the patient will die as a result of cancer," then the prediction could be an expected number of days.

In this implementation, a given patient involved in training will have at least some data from each of the following categories of data: features, treatments and outcomes. Both features and treatments are inputs to the model, while outcomes are the output of the model. Under this formulation, the model expresses the fact that "this patient, with these features, under the condition that they receive this treatment, is likely to experience these outcomes."

In this implementation, one or more models are trained at 5716 to predict patient outcomes. One or more models may be combined into an ensemble of models. Each model may be any machine learning model that accepts structured features and performs classification or regression, including but not limited to: random forests; gradient boosted decision trees; multi-layer perceptrons; or any combination of the above.

After the models are trained, they are stored at 5718 to a database 5720 for subsequent inference.

In at least some implementations, any of image features 5706, clinical features 5710, treatments 5712 or outcomes 5714 may be extracted and stored in a database prior to training the models 5716 such that they do not need to be extracted while the model is being trained.

In at least some implementations, images are not used in the training process and blocks 5702, 5704 and 5706 are not present. In at least some implementations, clinical features are not used in the training process and block 5710 is not present. In at least some implementations, features are used as inputs without treatments, in which case block 5712 is not present.

At least one implementation of a system is designed as follows. The system predicts lung cancer-associated mortality for lung cancer patients. The model 5716 is trained with a set of patients, each of which has some associated features and some associated treatments that they received. The features include demographic features of the patients (age, sex, etc.), features from histopathological assessment of lesion biopsy (tumor stage, grade, presence of lymph node metastases), features related to medical procedures and complications in the preceding 12 months, and image features from the most recent thoracic CT exam (current tumor size, change in tumor size since the previous thoracic CT exam, CNN-extracted features for a CNN that was trained to distinguish lesions from blood vessels in CT images e.g., following [Berens 2016]). The outcome associated with each patient is lung cancer-associated death within 365 days of the epoch. The epoch is the date of lung cancer diagnosis. Treatments are all treatments received by the patient between the epoch and 365 days after the epoch. The model is a random forest classification model. As described in the preceding sections, any or all of these specific design decisions may be altered in other implementations.

Inference

Figure 58:
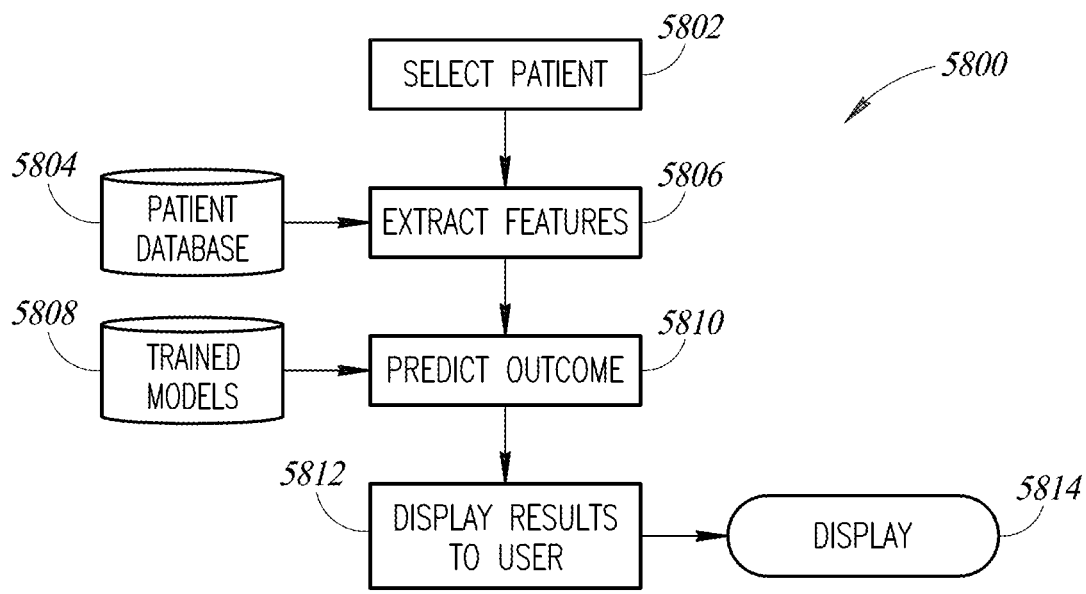
FIG. 58 is a flow diagram of a method of implementing a model inference process in a patient outcomes prediction system, according to one non-limiting illustrated implementation.

FIG. 58 shows a method 5800 of one implementation of the inference phase 5640 of the system 5600. Initially a patient is selected at 5802. In at least some implementations, the patient may be selected by a user; in other implementations, the patient is selected by an automated system. Using data from a patient database 5804, features are extracted for the patient at 5806. At least some of the features that are extracted 5806 are the same type of features, including one or more of image or clinical features extracted at 5706 and 5710 that are used in model training. For example, if cancer stage is a clinical feature 5710 used in model training, cancer stage may also be a feature extracted 5806 at inference time. One or more of the trained models 5808 (also 5720 in FIG. 57) that were created at training time at are loaded and used to predict outcomes 5810 using the extracted features 5806.

For implementations in which treatments 5712 were used as an input to model training, outcomes are predicted 5810 assuming that a certain treatment combination is used to treat the patient. In at least some implementations, this process is repeated for different treatment combinations. For example, outcomes may be predicted assuming treatment combination A is used, and separately, outcomes may be predicted assuming treatment combination B is used. Outcome predictions would then be separately available under the conditions that one of treatment combination A or treatment combination B is used. In this example, each of A or B may comprise one or more treatments. Those one or more treatments may or may not be administered to the patient simultaneously.

After outcomes are predicted 5810, the results are displayed to the user 5812 on a display 5814.

At least one implementation of a system is designed as follows. The system predicts lung cancer-associated mortality for lung cancer patients. A lung cancer patient is selected at 5802 with a known cancer diagnosis based on histopathological examination of a lung nodule biopsy. The features 5806 include demographic features of the patient (age, sex, etc.), features from histopathological assessment of lesion biopsy (tumor stage, grade, presence of lymph node metastases), features related to medical procedures and complications in the preceding 12 months, and features from the most recent thoracic CT exam (current tumor size, change in tumor size since the previous thoracic CT exam, CNN-extracted features for a CNN that was trained to distinguish lesions from blood vessels in CT images e.g., following [Berens 2016]). The outcome associated with the patient is lung cancer-associated death within 365 days of the epoch. The epoch is the date of lung cancer diagnosis. The models 5808 consist of a single random forest classification model. Outcomes are predicted 5810 for each of several different sets of treatments; treatment sets include chemotherapy, radiation, resection, others, and combinations of individual treatments. Because outcomes are predicted for different treatment combinations, the data provided to the user includes the likelihood of lung cancer-related mortality for each treatment combination; this is a prediction of "treatment success" (by at least one definition) for each treatment combination. As described in the preceding sections, any or all of these specific design decisions may be altered in other implementations.

Inference User Interface

Figure 59:
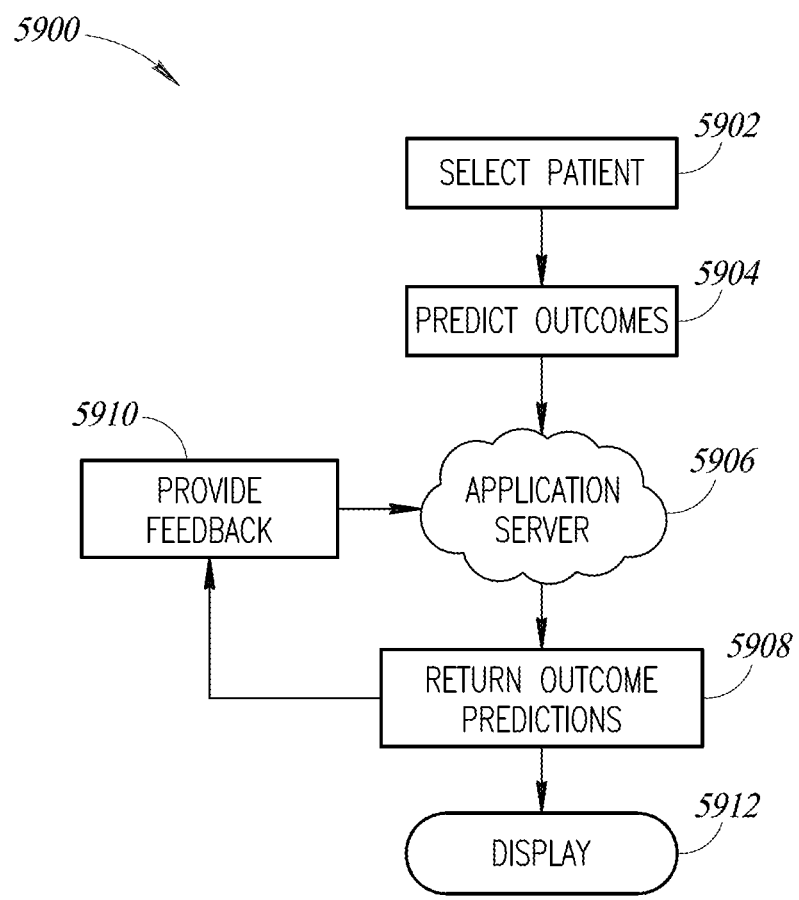
FIG. 59 is a flow diagram of a method of providing a user interface in a patient outcomes prediction system, according to one non-limiting illustrated implementation.

FIG. 59 shows one method 5900 of implementing a user interface with which the user can interact with the outcomes prediction system. Within the software application the user initially indicates the patient for whom they wish to invoke outcomes prediction 5902. The user either manually indicates that they wish to predict outcomes 5904 or the system predicts outcomes automatically. The request to predict outcomes is sent to the application server 5906 which may either be a remote server or it may reside on the user's computer. Data from which features will be extracted may either be sent to the application server 5906 along with the request, or the data may be retrieved from a separate location by the application server 5906. Outcome predictions are then returned 5908 and displayed to the user on a display 5912. The user may choose to disable or hide predictions for some treatments if they deem those treatments inapplicable to the current case.

In at least some implementations, the user has the option of providing feedback on the returned results 5910. The feedback mechanism may take on any of several forms, including but not limited to: retrospective information about the outcome of the patient (i.e., the user may indicate the true outcome after the outcome, such as lung cancer death, has already been observed); which treatments are applicable or inapplicable to the current case, and optionally, why; which prediction results they deem to be unreasonable, and optionally, why; or any combination of the above.

Figure 60:
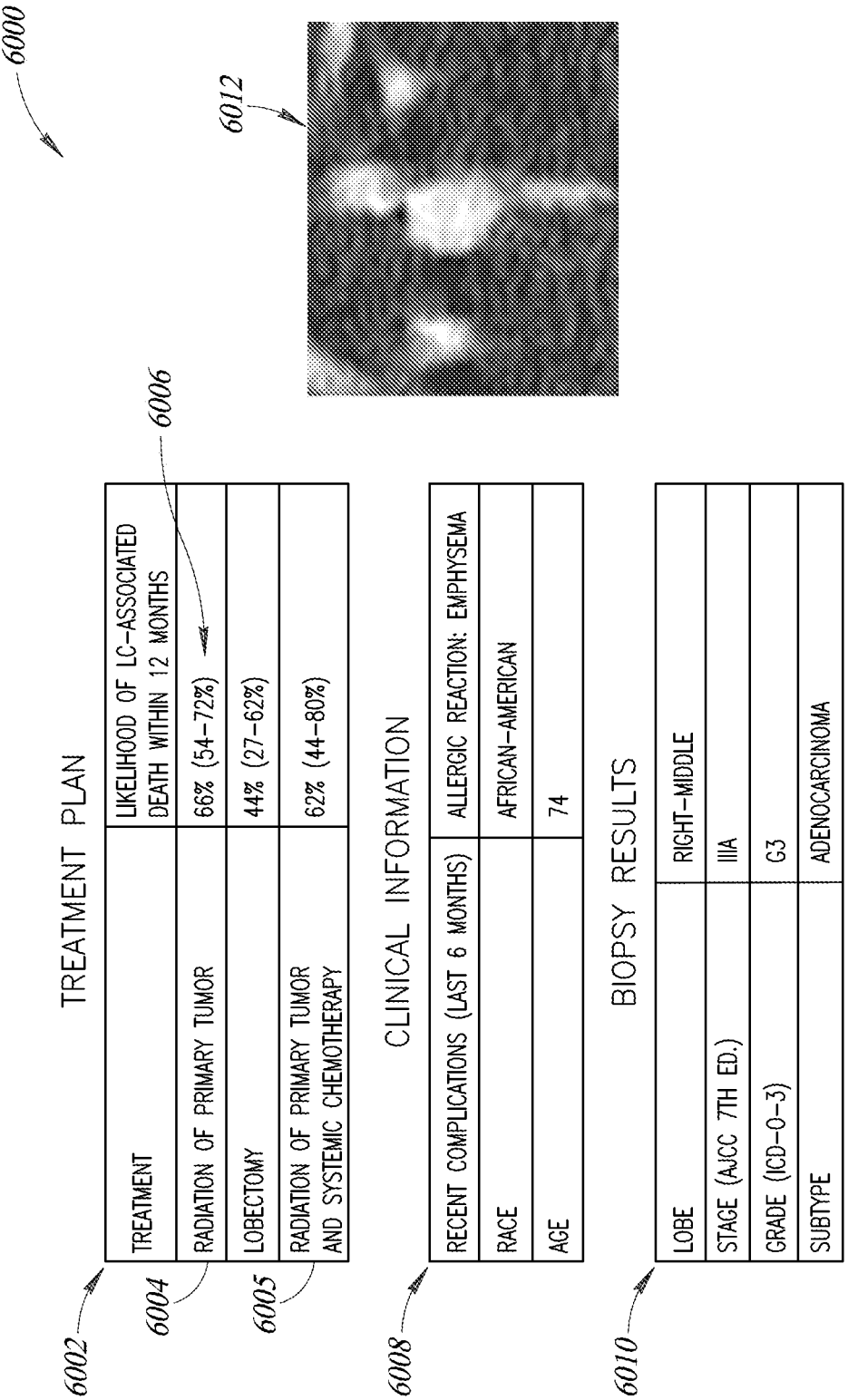
FIG. 60 is a user interface of a patient outcomes prediction system, showing prediction results, according to one non-limiting illustrated implementation.

FIG. 60 shows a GUI 6000 for displaying results. In particular, FIG. 60 shows the user interface 6000 for returned results 5912. A table 6002 of treatments along with the associated probability 6006 of lung cancer-associated death for each treatment 6004 is shown. The probability of lung cancer-associated death 6006 is derived from model output 5908. In this implementation, confidence intervals for the predicted probabilities are also shown in parentheses 6006; other implementations may not show confidence intervals, or may display confidence using a different format, such as categorical "low," "medium" or "high" confidence. Reasonable combinations of treatments (e.g., "radiation of primary tumor and systemic chemotherapy" 6005) are shown as individual rows in the table. Clinical information about the patient is also shown for reference 6008, along with histopathological biopsy results 6010. An image of the lesion 6012 is shown for reference. Some or all of this reference information could be the same information from which features are extracted for model inference. Other implementations may contain some or none of the displayed information in 6008, 6010 and 6012, or they could display additional reference information, such as molecular analysis of the biopsy result, medical history, or other information. Other implementations may show the probability of survival instead of the probability of death.

Figure 61:
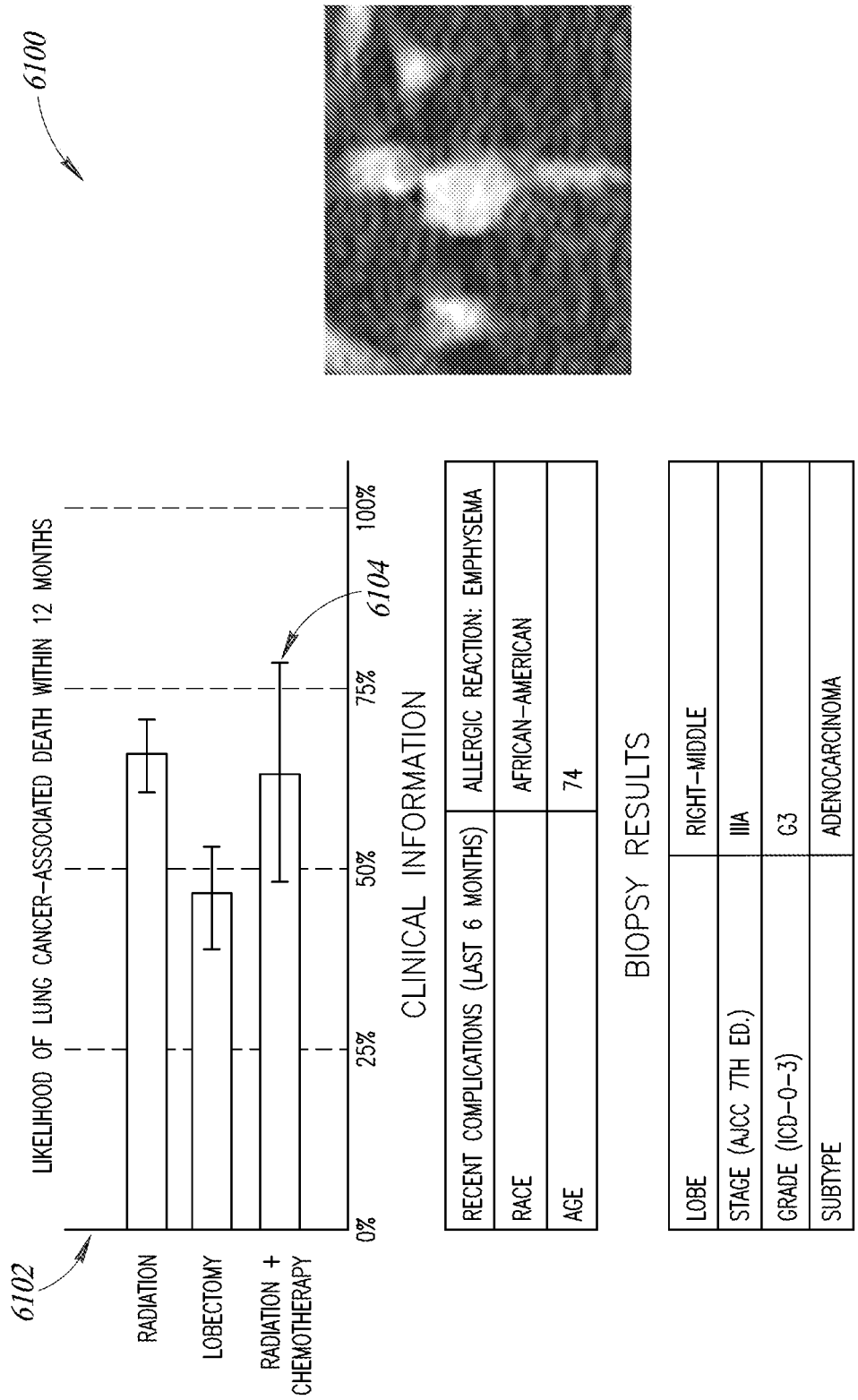
FIG. 61 is another user interface of a patient outcomes prediction system, showing prediction results, according to one non-limiting illustrated implementation.

FIG. 61 shows another implementation of a user interface 6100 for displaying results. In this implementation, outcomes are shown graphically. The probability of lung cancer-associated death is shown as a bar chart 6102, where the length of the bar is representative of the probability of death. Confidence intervals are shown as whiskers on the bars 6104. Other implementations may use other graphical chart forms, such as pie charts or line charts, for example.

H. CO-REGISTRATION

Medical imaging such as CT and MR is frequently used to create a 3D image of anatomy from a stack of 2D images, where the 3D image then consists of a three dimensional grid of voxels. While the technique is extremely powerful, its three dimensional nature frequently presents challenges when trying to interact with the data. For example, the simple task of viewing the resulting volume requires specialized 3D rendering and multiplanar reconstruction techniques.

A radiologist may want to correlate some feature within a 3D volume at one point in time to the same feature at another point in time. A radiologist may also want to correlate some feature within a 3D volume at a single time point but using multiple modalities (CT, MR, PET, NM). In order to do this, it is advantageous to align anatomical structures in one volume to the other using a geometric transform. The transform can include one or more of rotation, translation, scaling, and deformation. The determination of the transform to perform this alignment is referred to as co-registration.

An implementation is described whereby given two volumes of common anatomical structure, a transform is autonomously found that aligns the two volumes such that a feature or features common to both volumes can be easily correlated.

The following provides a description of one or more possible implementations of the present disclosure.

Given two volumes of common anatomical structure as input, a system may autonomously determine or find a transform that aligns the two volumes such that a feature or features common to both volumes can be easily correlated. First, the system, or a user thereof, may select a similarity metric to measure the quality of the transform. The metric may be configurable and may be intensity based or feature based, for example. Next, a vector of parameters that defines the transform are initialized. The number of parameters, N, determines the dimensionality of an optimization function used to determine the transform. In at least some implementations, an N dimensional search optimization space is then sampled both at regular intervals and stochastically. For example, for a parameter that specifies rotation that is specified in degrees constrained to be within ±30 degrees, the optimization space may be sampled stochastically between ±30 degrees, and at regular intervals (e.g., every X degrees between ±30 degrees, where X is an integer (e.g., 5, 10, 15)). As another non-limiting example, for a parameter that specifies a linear translation dimension that is specified in mm constrained to be within ±10 mm, the optimization space may be sampled stochastically between ±10 mm, and at regular intervals (e.g., every X mm between ±10 mm, where X is an integer (e.g., 2, 5, 10)).

The similarity between the two volumes is measured at each sample point using the selected similarity metric. For a collection of these sample points, an optimization algorithm (e.g., gradient descent) is used to find a transform that will maximize the similarity. Performing the gradient descent at multiple sample points (e.g., sample points measured at regular intervals and stochastically), mitigates the chances of landing in a poor local minimum, as the function is almost always non-convex.

Examples of similarity metrics include, but are not limited to, an intensity based metric or a feature based metric. An example intensity based metric that may be used is a sum of squared difference metric, which calculate the sum of the squared difference value for at least some (e.g., all voxels, voxels proximate one or more features) of the voxels in the two volumes. An example feature based metric that may be used is the inner product of the normalized gradient at least some of the voxels in the two volumes.

The vector parameters determining the transform may, in a rigid case, be a translation in 3D space and a rotation in 3D space, represented by six values. In an elastic case, the vector parameters may be a 3D spline of 3D vectors that define how regions of one volume need to move to be co-registered with a second volume. In an elastic case, the number of parameters may be numerous (e.g., tens, hundreds, thousands).

Example Processor-Based Device

Figure 62:
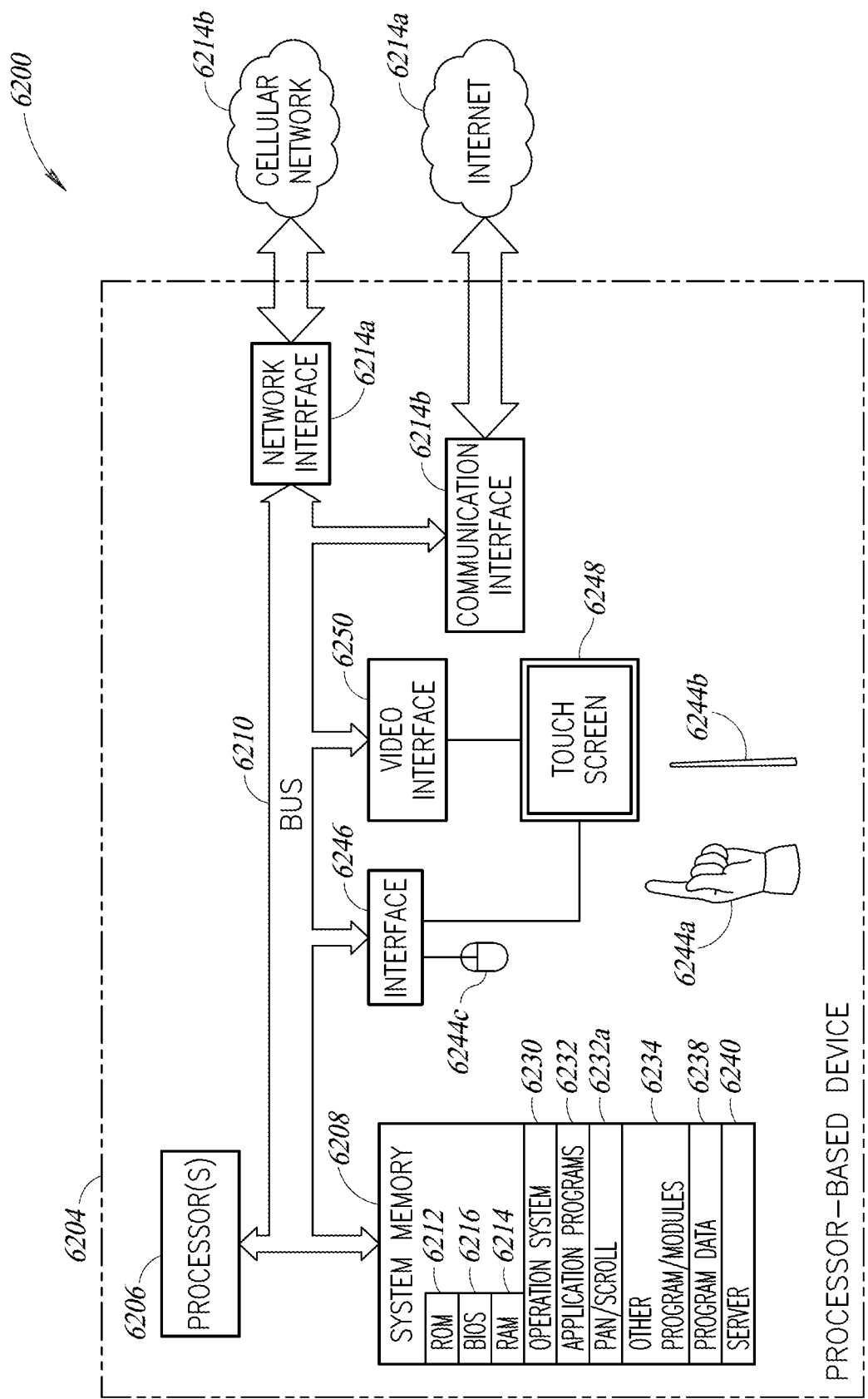
FIG. 62 is a block diagram of an example processor-based device used to implement one or more of the functions described herein, according to one non-limiting illustrated implementation.

FIG. 62 shows a processor-based device 6204 suitable for implementing the various functionality described herein. Although not required, some portion of the implementations will be described in the general context of processor-executable instructions or logic, such as program application modules, objects, or macros being executed by one or more processors. Those skilled in the relevant art will appreciate that the described implementations, as well as other implementations, can be practiced with various processor-based system configurations, including handheld devices, such as smartphones and tablet computers, wearable devices, multiprocessor systems, microprocessor-based or programmable consumer electronics, personal computers ("PCs"), network PCs, minicomputers, mainframe computers, and the like.

The processor-based device 6204 may include one or more processors 6206, a system memory 6208 and a system bus 6210 that couples various system components including the system memory 6208 to the processor(s) 6206. The processor-based device 6204 will at times be referred to in the singular herein, but this is not intended to limit the implementations to a single system, since in certain implementations, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, 68xxx series microprocessors from Motorola Corporation.

The processor(s) 6206 may be any logic processing unit, such as one or more central processing units (CPUs), microprocessors, digital signal processors (DSPs), application-specific integrated circuits (ASICs), field programmable gate arrays (FPGAs), etc. Unless described otherwise, the construction and operation of the various blocks shown in FIG. 62 are of conventional design. As a result, such blocks need not be described in further detail herein, as they will be understood by those skilled in the relevant art.

The system bus 6210 can employ any known bus structures or architectures, including a memory bus with memory controller, a peripheral bus, and a local bus. The system memory 6208 includes read-only memory ("ROM") 1012 and random access memory ("RAM") 6214. A basic input/output system ("BIOS") 6216, which can form part of the ROM 6212, contains basic routines that help transfer information between elements within processor-based device 6204, such as during start-up. Some implementations may employ separate buses for data, instructions and power.

The processor-based device 6204 may also include one or more solid state memories, for instance Flash memory or solid state drive (SSD) 6218, which provides nonvolatile storage of computer-readable instructions, data structures, program modules and other data for the processor-based device 6204. Although not depicted, the processor-based device 6204 can employ other nontransitory computer- or processor-readable media, for example a hard disk drive, an optical disk drive, or memory card media drive.

Program modules can be stored in the system memory 6208, such as an operating system 6230, one or more application programs 6232, other programs or modules 6234, drivers 6236 and program data 6238.

The application programs 6232 may, for example, include panning/scrolling 6232a. Such panning/scrolling logic may include, but is not limited to logic that determines when and/or where a pointer (e.g., finger, stylus, cursor) enters a user interface element that includes a region having a central portion and at least one margin. Such panning/scrolling logic may include, but is not limited to logic that determines a direction and a rate at which at least one element of the user interface element should appear to move, and causes updating of a display to cause the at least one element to appear to move in the determined direction at the determined rate. The panning/scrolling logic 6232a may, for example, be stored as one or more executable instructions. The panning/scrolling logic 6232a may include processor and/or machine executable logic or instructions to generate user interface objects using data that characterizes movement of a pointer, for example data from a touch-sensitive display or from a computer mouse or trackball, or other user interface device.

The system memory 6208 may also include communications programs 6240, for example a server and/or a Web client or browser for permitting the processor-based device 6204 to access and exchange data with other systems such as user computing systems, Web sites on the Internet, corporate intranets, or other networks as described below. The communications programs 6240 in the depicted implementation is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 62 as being stored in the system memory 6208, the operating system 6230, application programs 6232, other programs/modules 6234, drivers 6236, program data 6238 and server and/or browser 6240 can be stored on any other of a large variety of nontransitory processor-readable media (e.g., hard disk drive, optical disk drive, SSD and/or flash memory).

A user can enter commands and information via a pointer, for example through input devices such as a touch screen 6248 via a finger 6244a, stylus 6244b, or via a computer mouse or trackball 6244c which controls a cursor. Other input devices can include a microphone, joystick, game pad, tablet, scanner, biometric scanning device, etc. These and other input devices (i.e., "I/O devices") are connected to the processor(s) 6206 through an interface 6246 such as touch-screen controller and/or a universal serial bus ("USB") interface that couples user input to the system bus 6210, although other interfaces such as a parallel port, a game port or a wireless interface or a serial port may be used. The touch screen 6248 can be coupled to the system bus 6210 via a video interface 6250, such as a video adapter to receive image data or image information for display via the touch screen 6248. Although not shown, the processor-based device 6204 can include other output devices, such as speakers, vibrator, haptic actuator, etc.

The processor-based device 6204 may operate in a networked environment using one or more of the logical connections to communicate with one or more remote computers, servers and/or devices via one or more communications channels, for example, one or more networks 6214a, 6214b. These logical connections may facilitate any known method of permitting computers to communicate, such as through one or more LANs and/or WANs, such as the Internet, and/or cellular communications networks. Such networking environments are well known in wired and wireless enterprise-wide computer networks, intranets, extranets, the Internet, and other types of communication networks including telecommunications networks, cellular networks, paging networks, and other mobile networks.

When used in a networking environment, the processor-based device 6204 may include one or more wired or wireless communications interfaces 6214a, 6214b (e.g., cellular radios, WI-FI radios, Bluetooth radios) for establishing communications over the network, for instance the Internet 6214a or cellular network.

In a networked environment, program modules, application programs, or data, or portions thereof, can be stored in a server computing system (not shown). Those skilled in the relevant art will recognize that the network connections shown in FIG. 62 are only some examples of ways of establishing communications between computers, and other connections may be used, including wirelessly.

For convenience, the processor(s) 6206, system memory 6208, network and communications interfaces 6214a, 624b are illustrated as communicably coupled to each other via the system bus 6210, thereby providing connectivity between the above-described components. In alternative implementations of the processor-based device 6204, the above-described components may be communicably coupled in a different manner than illustrated in FIG. 62. For example, one or more of the above-described components may be directly coupled to other components, or may be coupled to each other, via intermediary components (not shown). In some implementations, system bus 6210 is omitted and the components are coupled directly to each other using suitable connections.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Those of skill in the art will recognize that many of the methods or algorithms set out herein may employ additional acts, may omit some acts, and/or may execute acts in a different order than specified.

In addition, those skilled in the art will appreciate that the mechanisms taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/571,908 filed Jul. 7, 2011; U.S. Pat. No. 9,513,357 issued Dec. 6, 2016; U.S. patent application Ser. No. 15/363,683 filed Nov. 29, 2016; U.S. Provisional Patent Application No. 61/928,702 filed Jan. 17, 2014; U.S. patent application Ser. No. 15/112,130 filed Jul. 15, 2016; U.S. Provisional Patent Application No. 62/260,565 filed Nov. 20, 2015; 62/415,203 filed Oct. 31, 2016; U.S. patent application Ser. No. 15/779,445 filed May 25, 2018, U.S. patent application Ser. No. 15/779,447 filed May 25, 2018, U.S. Provisional Patent Application No. 62/415,666 filed Nov. 1, 2016; U.S. patent application Ser. No. 15/779,448, filed May 25, 2018, U.S. Provisional Patent Application No. 62/451,482 filed Jan. 27, 2017; International Patent Application No. PCT/US2018/015222 filed Jan. 25, 2018, U.S. Provisional Patent Application No. 62/501,613 filed May 4, 2017; International Patent Application No. PCT/US2018/030,963 filed May 3, 2018, U.S. Provisional Patent Application No. 62/512,610 filed May 30, 2017; U.S. patent application Ser. No. 15/879,732 filed Jan. 25, 2018; U.S. patent application Ser. No. 15/879,742 filed Jan. 25, 2018; U.S. Provisional Patent Application No. 62/589,825 filed Nov. 22, 2017; U.S. Provisional Patent Application No. 62/589,805 filed Nov. 22, 2017; U.S. Provisional Patent Application No. 62/589,772 filed Nov. 22, 2017; U.S. Provisional Patent Application No. 62/589,872 filed Nov. 22, 2017; U.S. Provisional Patent Application No. 62/589,876 filed Nov. 22, 2017; U.S. Provisional Patent Application No. 62/589,766 filed Nov. 22, 2017; U.S. Provisional Patent Application No. 62/589,833 filed Nov. 22, 2017 and U.S. Provisional Patent Application No. 62/589,838 filed Nov. 22, 2017 are incorporated herein by reference, in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

REFERENCES

[Chung 2017] Chung, Kaman, et al. "Malignancy estimation of Lung-RADS criteria for subsolid nodules on CT:

accuracy of low and high risk spectrum when using NLST nodules." European Radiology (2017): 1-8.

[ACR Lung-RADS] American College of Radiology Lung CT Screening Reporting and Data System (Lung-RADS™) https://www[dot]acr.org/Quality-Safety/Resources/LungRADS. Accessed Sep. 8, 2017.

[ACR LI-RADS] American College of Radiology Liver Imaging Reporting and Data System. https://www[dot]acr.org/Quality-Safety/Resources/LIRADS. Accessed Nov. 8, 2017.

[Gulshan 2016] Gulshan, Varun, et al. "Development and validation of a deep learning algorithm for detection of diabetic retinopathy in retinal fundus photographs." Jama 316.22 (2016): 2402-2410.

[van Riel 2015] van Riel, Sarah J., et al. "Observer variability for classification of pulmonary nodules on low-dose CT images and its effect on nodule management." Radiology 277.3 (2015): 863-871.

[Armato 2011] Armato, Samuel G., et al. "The lung image database consortium (LIDC) and image database resource initiative (IDRI): a completed reference database of lung nodules on CT scans." Medical physics 38.2 (2011): 915-931.

[Russakovsky 2015] Russakovsky, Olga, et al. "Imagenet large scale visual recognition challenge." International Journal of Computer Vision 115.3 (2015): 211-252.

[He 2016] He, Kaiming, et al. "Deep residual learning for image recognition." Proceedings of the IEEE conference on computer vision and pattern recognition. 2016.

[LeCun 1998] LeCun, Yann, et al. "Gradient-based learning applied to document recognition." Proceedings of the IEEE 86.11 (1998): 2278-2324.

[Muja 2009] Muja, Marius, and David G. Lowe. "Fast approximate nearest neighbors with automatic algorithm configuration." VISAPP (1) 2.331-340 (2009): 2.

[Ysung-Yi 2017] Lin, Ysung-Yi, et al. "Focal loss for dense object detection." arXiv preprint arXiv:1709:02002 (2017).

[Berens 2016] Berens Moira, van der Gugten Robbert, de Kaste Michael, Manders Jeroen, and Zuidhof Guido. 2016. ZNET—LUNG NODULE DETECTION. (2016). http://luna16[dot]grand-challenge.org/serve/public_html/pdfs/ZNET_NDET_160831.pdf/. Accessed Sep. 18, 2017.

[NLST 2011] National Lung Screening Trial Research Team. "Reduced lung-cancer mortality with low-dose computed tomographic screening." N Engl J Med 2011.365 (2011): 395-409.

The invention claimed is:

1. A machine learning system, comprising:
at least one nontransitory processor-readable storage medium that stores at least one of processor-executable instructions or data; and
at least one processor communicably coupled to the at least one nontransitory processor-readable storage medium, in operation the at least one processor:
loads a trained machine learning model that has been designed to predict patients' clinical outcomes, wherein the machine learning model is trained based at least partially on medical images that indicate longitudinal changes of suspected lesions over time;
calculates features for a query patient who has a known or suspected diagnosis, based at least partially on medical images of the query patient that indicate longitudinal changes of suspected lesions over time;
identifies a selection of treatment options for the query patient from a list of available treatment options; and
for each of one or more of the identified treatment options, uses the features and treatment options as inputs to the trained machine learning model to generate prediction results, the prediction results comprising a prediction of the clinical outcomes for the query patient.

2. The machine learning system of claim 1 wherein, in operation, the at least one processor presents the prediction results of the machine learning model to a user via a display.

3. The machine learning system of claim 2 wherein, in operation, the at least one processor presents the prediction results in tabular format.

4. The machine learning system of claim 3 wherein the treatment options form one axis of the table and at least some of the cells of the table indicate the likelihood of occurrence of a given clinical outcome.

5. The machine learning system of claim 3 wherein at least some of the cells of the table indicate lower and upper confidence interval boundaries of the likelihood of occurrence of a given clinical outcome.

6. The machine learning system of claim 2 wherein, in operation, the at least one processor presents the prediction results in the form of a chart.

7. The machine learning system of claim 6 wherein one axis of the chart shows different treatment options and the other axis of the chart indicates likelihood of occurrence of a given clinical outcome.

8. The machine learning system of claim 6 wherein the chart format is a bar chart.

9. The machine learning system of claim 6 wherein the chart indicates upper and lower confidence interval boundaries of the prediction results.

10. The machine learning system of claim 1 wherein at least one treatment option is a combination of different treatments.

11. The machine learning system of claim 1 wherein the at least one processor permits a user to select the selection of treatment options.

12. The machine learning system of claim 1 wherein at least some of the features calculated by the at least one processor are clinical features.

13. The machine learning system of claim 12 wherein the clinical features include one or more of patient demographic information, patient medical history, family medical history or diagnostic information related to a current lesion.

14. The machine learning system of claim 1 wherein at some of the features calculated by the at least one processor are calculated from medical images of the query patient.

15. The machine learning system of claim 14 wherein at least some of the calculated features are calculated using one or more pre-trained CNN models.

16. The machine learning system of claim 15 wherein the one or more pre-trained CNN models include at least one of a classification model, an object detection model or a semantic segmentation model.

17. The machine learning system of claim 1 wherein at least some of the clinical outcomes predicted by the at least one processor include one or more of cancer-related mortality, overall mortality, response to treatment, cancer recurrence, medical complications, adverse events, patient quality of life or optimal treatment.

18. The machine learning system of claim 1 wherein the trained machine learning model that is used by the at least one processor to predict the query patient's clinical outcomes is an ensemble of one or more of a random forest, gradient boosted decision trees or a multi-layer perceptron.

19. The machine learning system of claim 1 wherein the query patient has known or suspected lung cancer.

20. The machine learning system of claim 1 wherein the query patient has known or suspected liver cancer.

21. A computer-implemented method, comprising:
loading a trained machine learning model that has been designed to predict patients' clinical outcomes, wherein the machine learning model is trained based at least partially on medical images that indicate longitudinal changes of suspected lesions over time;
calculating features for a query patient who has a known or suspected diagnosis, based at least partially on medical images of the query patient that indicate longitudinal changes of suspected lesions over time;
identifying a selection of treatment options for the query patient from a list of available treatment options; and
for each of one or more of the identified treatment options, using the features and treatment options as inputs to the trained machine learning model to generate prediction results, the prediction results comprising a prediction of the clinical outcomes for the query patient.

22. The method of claim 21 wherein the prediction results further indicate at least one of a likelihood of occurrence of a given clinical outcome or different treatment options.

23. The method of claim 21 wherein at least some of the features calculated include one or more of patient demographic information, patient medical history, family medical history or diagnostic information related to a current lesion.

24. The method of claim 21 wherein at least some of the features are calculated based, at least in part, on medical images of the query patient.

25. The method of claim 24 wherein at least some of the features are calculated using one or more pre-trained convolutional neural network (CNN) models.

26. The method of claim 25 wherein the one or more pre-trained CNN models include at least one of a classification model, an object detection model or a semantic segmentation model.

27. The method of claim 21 wherein at least some of the clinical outcomes predicted include one or more of cancer-related mortality, overall mortality, response to treatment, cancer recurrence, medical complications, adverse events, patient quality of life or optimal treatment.

28. The method of claim 21 wherein the trained machine learning model includes an ensemble of one or more of a random forest, gradient boosted decision trees or a multi-layer perceptron.

* * * * *